United States Patent [19]

Spencer et al.

[11] Patent Number: 5,707,842

[45] Date of Patent: *Jan. 13, 1998

[54] METHOD FOR REGULATING ENZYME ACTIVITIES BY NOBLE GASES

[75] Inventors: Kevin C. Spencer, Riverside; Pascal Schvester; Christine E. Boisrobert, both of Chicago, all of Ill.

[73] Assignee: American Air Liquide, Chicago Research Center, Countryside, Ill.

[*] Notice: The term of this patent shall not extend beyond the expiration date of Pat. No. 5,364,777.

[21] Appl. No.: 445,525

[22] Filed: May 22, 1995

Related U.S. Application Data

[63] Continuation of Ser. No. 243,743, May 17, 1994, abandoned, which is a continuation of Ser. No. 46,756, Jun. 15, 1993, abandoned, which is a continuation of Ser. No. 706,587, May 28, 1991, abandoned.

[51] Int. Cl.$^6$ .............................. C12N 9/00; C12N 9/10; C12N 9/14; C01B 23/00

[52] U.S. Cl. .................. 435/183; 435/184; 435/189; 435/193; 435/195; 435/196; 435/219; 435/232; 435/233; 423/262

[58] Field of Search ..................... 435/183, 184, 435/189, 193, 195, 196, 232, 219, 233; 423/262

[56] References Cited

PUBLICATIONS

Doebbler et al. *Fed Proc* vol. 26, 1967, p. 650.

Sandhoff et al. *FEBS Letters* 62(3), 1976, pp. 284–287.

*Primary Examiner*—Blaine Lankford
*Attorney, Agent, or Firm*—Oblon, Spivak, McClelland, Maier & Neustadt, P. C.

[57] ABSTRACT

A method for regulating enzyme activity, which entails contacting one or more enzymes with a gas containing one or more noble gases or mixtures thereof.

13 Claims, 48 Drawing Sheets

METHOD FOR REGULATING ENZYME ACTIVITIES BY NOBLE GASES

This application is a Continuation of application Ser. No 08/243,743, filed May 17, 1994, which is a continuation of application Ser. No. 08/046,756, filed Jun. 15, 1993, which is a continuation of application Ser. No. 07/706,587, May 28, 1991, all now abandoned.

BACKGROUND OF THE INVENTION

2. Field of the Invention

The present invention relates to a method for regulating enzyme activities by noble gases.

2. Description of the Background

The ability of the noble gases helium (He), neon (Ne), argon (Ar), krypton (Kr), xenon (Xe) and radon (Ra) to enter into chemical combination with other atoms is extremely limited. Generally, only krypton, xenon and radon have been induced to react with other atoms, such as fluorine and oxygen, and the compounds thus formed are explosively unstable. See *Advanced Inorganic Chemistry*, by F. A. Cotton and G. Wilkinson (Wiley, Third Edition). However, while the noble gases are, in general, chemically inert, xenon is known to exhibit certain physiological effects, such as anesthesia. Other physiological effects have also been observed with other inert gases such as nitrogen, which, for example, is known to cause narcosis when used under great pressure in deep-sea diving.

It has been reported in U.S. Pat. No. 3,183,171 to Schreiner that argon and other inert gases can influence the growth rate of fungi and argon is known to improve the preservation of fish or seafood. U.S. Pat. No. 4,946,326 to Schvester, JP 52105232, JP 80002271 and JP 77027699. However, the fundamental lack of understanding of these observations clearly renders such results difficult, if not impossible, to interpret. Moreover, the meaning of such observations is further obscured by the fact that mixtures of many gases, including oxygen, were used in these studies. Further, some of these studies were conducted at hyperbaric pressures and at freezing temperatures. At such high pressures, it is likely that the observed results were caused by pressure damage to cellular components and to the enzymes themselves.

For example, from 1964 to 1966, Schreiner documented the physiological effects of inert gases particularly as related to anesthetic effects and in studies relating to the development of suitable containment atmospheres for deep-sea diving, submarines and spacecraft. The results of this study are summarized in three reports, each entitled: "Technical Report. The Physiological Effects of Argon, Helium and the Rare Gases," prepared for the Office of Naval Research, Department of the Navy. Contract Nonr 4115(00), NR: 102–597. Three later summaries and abstracts of this study were published.

One abstract, "Inert Gas Interactions and Effects on Enzymatically Active Proteins," Fed. Proc. 26:650 (1967), restates the observation that the noble and other inert gases produce physiological effects at elevated partial pressures in intact animals (narcosis) and in microbial and mammalian cell systems (growth inhibition).

A second abstract, "A Possible Molecular Mechanism for the Biological Activity of Chemically Inert Gases," In: Intern. Congr. Physiol. Sci., 23rd, Tokyo, restates the observation that the inert gases exhibit biological activity at various levels of cellular organization at high pressures.

Also, a summary of the general biological effects of the noble gases was published by Schreiner in which the principal results of his earlier research are restated. "General Biological Effects of the Helium-Xenon Series of Elements," Fed. Proc. 27:872–878 (1968).

However, in 1969, Behnke et al refuted the major conclusions of Schreiner. Behnke et al concluded that the effects reported earlier by Schreiner are irreproducible and result solely from hydrostatic pressure, i.e., that no effects of noble gases upon enzymes are demonstrable. "Enzyme-Catalyzed Reactions as Influenced by Inert Gases at High Pressures." J. Food Sci. 34:370–375.

In essence, the studies of Schreiner were based upon the hypothesis that chemically inert gases compete with oxygen molecules for cellular sites and that oxygen displacement depends upon the ratio of oxygen to inert gas concentrations. This hypothesis was never demonstrated as the greatest observed effects (only inhibitory effects were observed) were observed with nitrous oxide and found to be independent of oxygen partial pressure. Moreover, the inhibition observed was only 1.9% inhibition per atmosphere of added nitrous oxide.

In order to refute the earlier work of Schreiner, Behnke et al independently tested the effect of high hydrostatic pressures upon enzymes, and attempted to reproduce the results obtained by Schreiner. Behnke et al found that increasing gas pressure of nitrogen or argon beyond that necessary to observe a slight inhibition of chymotrypsin, invertase and tyrosinase caused no further increase in inhibition, in direct contrast to the finding of Schreiner.

The findings of Behnke et al can be explained by simple initial hydrostatic inhibition, which is released upon stabilization of pressure. Clearly, the findings cannot be explained by the chemical-$O_2$/inert gas interdependence as proposed by Schreiner. Behnke et al concluded that high pressure inert gases inhibit tyrosinase in non-fluid (i.e., gelatin) systems by decreasing oxygen availability, rather than by physically altering the enzyme. This conclusion is in direct contrast to the findings of Schreiner.

In addition to the refutation by Behnke et al, the results reported by Schreiner are difficult, if not impossible, to interpret for other reasons as well.

First, all analyses were performed at very high pressure, and were not controlled for hydrostatic pressure effects.

Second, in many instances, no significant differences were observed between the various noble gases, nor between the noble gases and nitrogen.

Third, knowledge of enzyme mode of action and inhibition was very poor at the time of these studies, as were the purities of enzymes used. It is impossible to be certain that confounding enzyme activities were not present or that measurements were made with a degree of resolution sufficient to rank different gases as to effectiveness. Further, any specific mode of action could only be set forth as an untestable hypothesis.

Fourth, solubility differences between the various gases were not controlled, nor considered in the result.

Fifth, all tests were conducted using high pressures of inert gases superimposed upon 1 atmosphere of air, thus providing inadequate control of oxygen tension.

Sixth, all gas effects reported are only inhibitions.

Seventh, not all of the procedures in the work have been fully described, and may not have been experimentally controlled. Further, long delays after initiation of the enzyme reaction precluded following the entire course of reaction, with resultant loss of the highest readable rates of change.

Eighth, the reported data ranges have high variability based upon a small number of observations, thus precluding significance.

Ninth, the levels of inhibition observed are very small even at high pressures.

Tenth, studies reporting a dependence upon enzyme concentration do not report significant usable figures.

Eleventh, all reports of inhibitory potential of inert gases at low pressures, i.e., <2 atm., are postulated based upon extrapolated lines from high pressure measurements, not actual data.

Finally, it is worthy of reiterating that the results of Behnke et al clearly contradict those reported by Schreiner in several crucial respects, mainly that high pressure effects are small and that hydrostatic effects, which were not controlled by Schreiner, are the primary cause of the incorrect conclusions made in those studies.

Additionally, although it was reported by Sandhoff et al, FEBS Letters, vol. 62, no. 3 (March, 1976) that xenon, nitrous oxide and halothane enhance the activity of particulate sialidase, these results are questionable due to the highly impure enzymes used in this study and are probably due to inhibitory oxidases in the particles.

To summarize the above patents and publications and to mention others related thereto, the following is noted.

Behnke et al (1969), disclose that enzyme-catalyzed reactions are influenced by inert gases at high pressures. J. Food Sci. 34: 370–375.

Schreiner et al (1967), describe inert gas interactions and effects on enzymatically active proteins. Abstract No. 2209. Fed. Proc. 26:650.

Schreiner, H. R. 1964, Technical Report, describes the physiological effects of argon, helium and the rare gases. Contract Nonr 4115 (00), NR: 102–597. Office of Naval Research, Washington, D.C.

Schreiner, H. R. 1965, Technical Report, describes the physiological effects of argon, helium and the rare gases. Contract Nonr 4115 (00), NR: 102–597. Office of Naval Research, Washington, D.C.

Schreiner, H. R. 1966, Technical Report, describes the physiological effects of argon, helium and the rare gases. Contract Nonr 4115 (00), NR: 102–597. Office of Naval Research, Washington, D.C.

Importantly, in none of the above studies was the empirical conclusion reached that the treating gases had interacted with the enzyme active sites.

Nevertheless, at present, it is known that enzyme activities can be inhibited in several ways. For example, many enzymes can be inhibited by specific poisons that may be structurally related to their normal substrates. Alternatively, many different reagents are known to be specific inactivators of target enzymes. These reagents generally cause chemical modification at the active site of the enzyme to induce loss of catalytic activity, active-site-directed irreversible inactivation or affinity labeling. See *Enzymatic Reaction Mechanism* by C. Walsh (W. H. Freeman & Co., 1979). Alternatively, certain multi-enzyme sequences are known to be regulated by particular enzymes known as regulatory or allosteric enzymes. See *Bioenergetics*, by A. L. Leninger (Benjamin/Cummings Publishing Co., 1973).

However, it would be extremely advantageous if a much simpler approach could be attained for regulating enzyme activities in a predictable and controllable manner. Moreover, it would be extremely advantageous if a means could be found for selectively inhibiting or enhancing enzyme activities in a predictable and controllable manner.

SUMMARY OF THE INVENTION

Accordingly, it is an object of the present invention to provide a method for regulating enzyme activities in a simple and straightforward manner.

It is also an object of the present invention to provide a method for regulating enzyme activities without using reagents which are structurally designed to inactivate target enzymes.

It is also an object of the present invention to provide a method for regulating enzyme activities without using enzyme poisons which are structurally related to normal enzyme substrates.

Furthermore, it is an object of the present invention to provide a method of shifting optimal relative enzyme-substrate concentrations and to modify optimal reaction conditions in relation to physical parameters.

The above objects and others which will become more apparent in view of the following disclosure are provided by a method for regulating enzyme activities which entails contacting one or more enzymes with a gas comprising one or more noble gases.

DETAILED DESCRIPTION OF THE PREFERRED EMBODIMENTS

Figure 1:
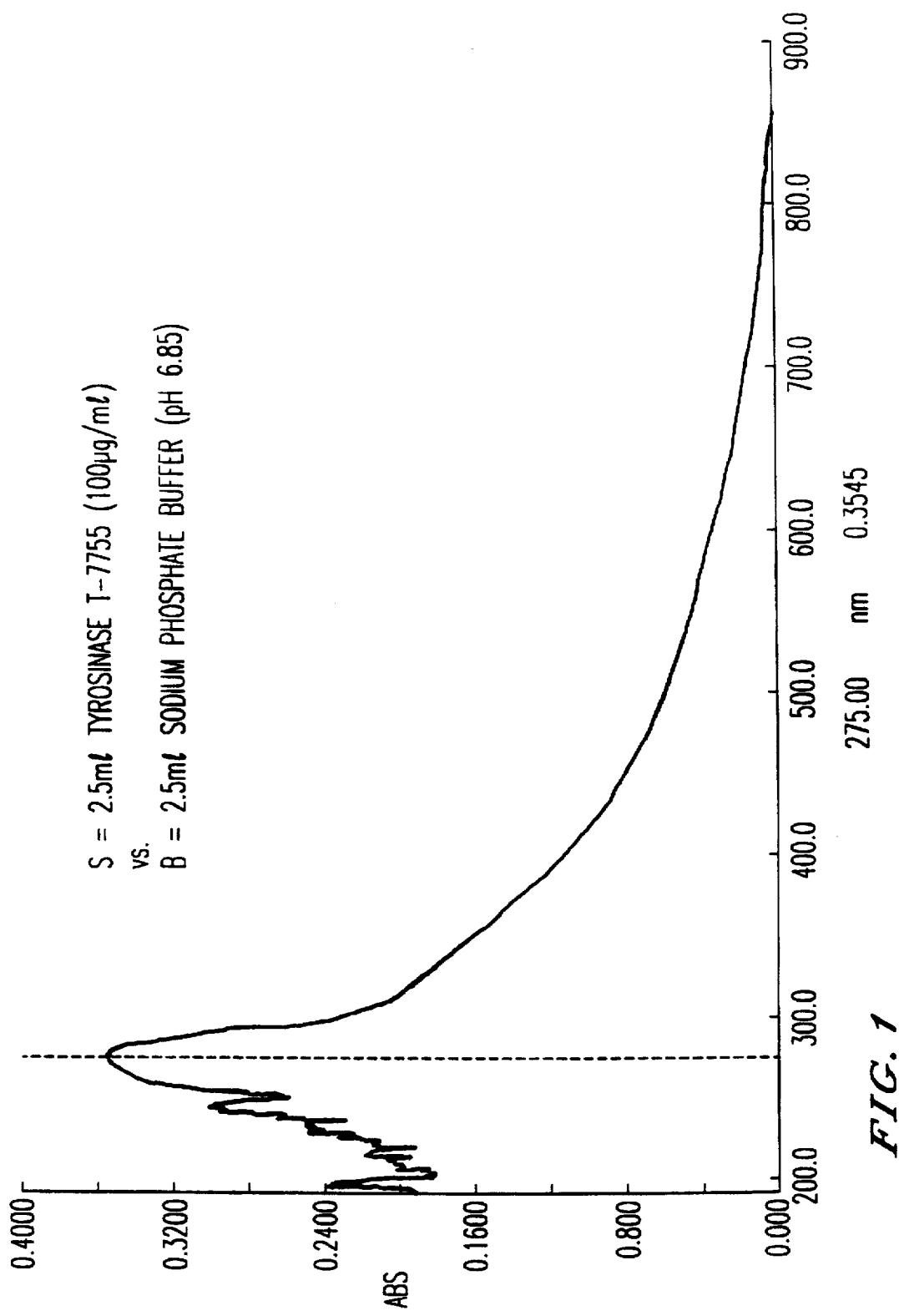
FIG. 1 illustrates the absorption spectrum of tyrosinase.

In accordance with the present invention, it has now been surprisingly discovered that enzyme activities can be regulated in a controlled and predictable manner by contacting of one or more enzymes with a gas containing one or more noble gases. Quite surprisingly, it has been discovered that noble gases have significant effects upon enzymes even at low pressure, and over a wide range of temperature.

The present invention is, indeed, quite surprising, for several reasons. First, in accordance with the present invention, the regulation of enzyme activities can be effected at low pressures. However, higher pressures may be used. Second, excellent results may also be obtained with mixtures of noble gases, including other gases such as nitrogen, oxygen carbon dioxide, carbon monoxide and nitrous oxide for example. Generally, any gas may be used in the gas mixtures in addition to the present noble gases. However, most typically such other gases include oxygen, nitrogen and carbon dioxide.

As used herein the term "noble gas" means any gas from the group of helium, neon, argon, krypton, xenon or radon. However, it is generally preferred that neon, argon, krypton or xenon be used simply because helium has a low solubility and high rate of departure from application systems and radon is dangerously radioactive.

In accordance with the present invention, single, pure noble gas may be used, or mixtures of noble gases may be used. For example, it is advantageous to use inexpensive production plant offstream gases having a composition of about 90% Kr and 10% Xe, in volume % based on the total gas volume. However, mixtures of one or more noble gases with other gases, such as nitrogen, sulfur hexafluoride, carbon oxygen or oxygen may be used, for example.

In accordance with the present invention, it has been discovered that the effects of one or more noble gases upon enzyme activity is observed in aqueous or organic solutions, dispersions, suspensions or in other types of matrices, such as gels. Further, the enzymes regulated may be bound or unbound to supports. The noble gases, themselves, may be in solution, in the atmosphere or in a bound form.

The present invention is predicated upon the fundamental discovery that enzymes representing all six enzyme classes, as classified by the Joint Commission on Biochemical Nomenclature of the International Union of Biochemistry and International Union of Pure and Applied Chemistry, are reproducibly enhanced or inhibited in their activity by contact even at low pressures with pure noble gases or in mixtures thereof or even in mixtures with other gases.

In accordance with the present invention, it has been discovered that the gases and gas mixtures of the present invention can effect both kinetic and thermodynamic control over enzymatic activity. That is, it is now possible to control both the rate and yield of an enzymatic reaction.

Although the solubility of the present gases and gas mixtures in reaction mixtures influences the measured effect of the gases and gas mixtures, the solubility does not wholly determine the effect. The effect is largely due to molecular effects such as polarizability, ionicity, Van der Waals forces and atomic radii. Generally, in accordance with the present invention, increasing temperature will limit the gas available due to decreasing solubility and decrease the effects. However, this decrease in effect offst by an increase in polarizability with increasing temperature. Thus, at temperatures of about 30° C. and higher, the increased polarizability of the gases and gas mixtures has a more pronounced influence as the effect of the gases and gas mixtures than the solubility characteristics.

Generally, by increasing the molar concentration of the noble gas or noble gas mixtures above standard temperature and pressure (STP), the observed effect on the enzyme is increased. Further, the effects appear to be based upon the interaction of gas molecules with enzymes, which is independent of, but can be ameliorated or potentiated by, the admixture of other gases. Notably, mixtures of noble gases behave in the same manner as pure noble gases, and mixtures of several gases are found to mimic, reverse or improve the effects observed with a single noble gas.

Additionally, in accordance with the present invention, it has been discovered that a particular noble gas or mixtures thereof may either inhibit or enhance enzymatic activity as a function of temperature.

Furthermore, in accordance with the present invention it has been discovered that, in general, under the appropriate conditions of pH, temperature, pressure, [E] and [S], all enzymes can be inhibited specifically by each of the noble gases of the present invention.

The present invention may be utilized to regulate enzyme activities in any application where enzymes are used. For example, the present invention may be used advantageously in the production of antibiotics, such as penicillin; in the production of ethanol and acetic acid; in the manufacture of diagnostic kits; in the manufacture of fermentation products, such as beer, wine and cheese; and in large scale enzymatic conversions generally.

As noted above, the present invention may be used advantageously in regulating the activities of enzymes from any of the six recognized enzyme categories. The examples provided hereinbelow are illustrative and are not intended to be limitative.

In particular, the present invention may be used advantageously in regulating oxidoreductases, which include, for example, dehydrogenases, oxidases, peroxidases, hydroxylases and oxygenases. Specific examples of oxidoreductases are tyrosinase, glucose oxidase, acetoin dehydrogenase, taurine dehydrogenase, octopine dehydrogenase, azobenzene reductase, acetoindoxyl oxidase, hypotaurine dehydrogenase, pseudomonas cytochrome oxidase, 3-hydroxyanthranilate oxidase, chloride peroxidase, cytochrome C3 hydrogenase, meliotate 3-monooxygenase, CDP-4-keto-6-deoxy-deglucose reductase and rubredoxin NaD$^+$ reductase and chlorate reductase, for example. However, any oxidoreductase enzyme may be used.

A second category of enzymes which can be regulated in accordance with the present invention are the transferases. Specific examples of transferases are carnosine N-methyl transferase, 3-oxoacyl acyl carrier protein synthase, laminaribose phosphorylase, galactose 6-sulfurylase, diiodo tyrosine aminotransferase, sedoheptylokinase and psychosine sulfurotransferase, 8-glutamyl transpeptidase and aspartate aminotransferase, for example. However, any transferase may be used.

A third category of enzymes which can be regulated in accordance with the present invention are hydrolases, which include esterases, phosphatases, glycosidases and peptidases, for example.

Specific examples of hydrolases are dihydrocoumarin hydrolase, β-D-glucosidase, α-glucosidase, ribosohomocysteinase, acylmuramylalanine carboxypeptidase, ureidosuccinase, phloretin hydrolase and 2-haloacid dehalogenase, for example. However, any hydrolase may be used.

A fourth category of enzymes which can be regulated in accordance with the present invention are lyases, including decarboxylases, aldolases and dehydratases, for example. Specific examples of lyases are phenylalamine ammonia lyase, citrate synthetase, methyl glyoxyl synthase, ureidoglycolate lyase, alliin lyase, chorismate synthase and alkyl mercury lyase, for example. However, any lyase may be used.

A fifth category of enzymes which can be regulated in accordance with the present invention are isomerases, including racemases, epimerases, cis-trans isomerases, intramolecular oxidoreductases and intramolecular transferases, for example. Specific examples which may be mentioned are glucose phosphate isomerase, UDP arabinose 4-epimerase, maleyl acetoacetate isomerase, chorismate mutase and muconate cycloisomerase, for example. However, any isomerase may be used.

A sixth category of enzymes which can be regulated in accordance with the present invention are ligases, which include amino acid-RNA ligases, acid-thiol ligases, amide synthetases, peptide synthetases and cyclo-ligases, for example. Specific mention may be made of acetyl choline synthase, seryl-2-RNA synthetase, carnosine synthetase and methyl crotonyl CoA carboxylase, for example. However, any ligase may be used.

Although the present invention generally provides a method for regulating enzyme activities, it also provides several additional specific methods.

First, the present invention also provides a method of enhancing enzyme activities by contacting one or more enzymes with a gas containing one or more noble gases or mixtures thereof.

Second, the present invention also provides a method of inhibiting enzyme activities by contacting one or more enzymes with a gas containing one or more noble gases or mixtures thereof.

Third, the present invention provides a method of shifting the optimal pH and/or temperature of one or more enzymes by contacting one or more enzymes with a gas containing one or more noble gases or mixtures thereof.

Fourth, the present invention provides a particular method for regulating oxidoreductase enzyme activities by contacting one or more oxidoreductase enzymes with a gas containing one or more noble gases or mixtures thereof.

Fifth, the present invention also provides a method for the specific regulation of hydrolase enzymatic activity by contacting one or more hydrolase enzymes with a gas containing one or more noble gases or mixtures thereof.

Sixth, the present invention also provides a method for the specific regulatgion of lyase enzymatic activity by contacting one or more lyase enzymes with a gas containing one or more noble gases or mixtures thereof.

Seventh, the present invention also provides a method for the specific regulation of isomerase enzymatic activity by contacting one or more isomerase enzymes with a gas containing one or more noble gases or mixtures thereof.

Eighth, the present invention also provides a method for the specific regulation of ligase enzymatic activity by contacting one or more lyase enzymes with a gas containing one or more noble gases or mixtures thereof.

Ninth, the present invention also provides a method for the specific regulation of transferase enzymatic activity by contacting one or more transferase enzymes with a gas containing one or more noble gases or mixtures thereof.

Tenth, the present invention also provides a method for changing optimal relative enzyme-substrate concentration by contacting one or more enzymes with a gas containing one or more noble gases or mixtures thereof.

Eleventh, the present invention also provides a method for selectively regulating one enzyme in a mixture of two or more enzymes.

Importantly, the examples of enzymes listed above from each of the six general categories of enzymes are merely illustrative and are not intended to be limitative. In accordance with the present invention, any enzyme may be regulated using the present gases and gas mixtures. For example, any of the enzymes described in *Enzymes* by M. Dixon and E. C. Webb, Third Edition (Academic Press) may be regulated in accordance with the present invention.

Generally, as noted above, the gas containing one or more noble gases may be a single, pure noble gas or a mixture of noble gases. The gas may also be a mixture of one or more noble gases with other gases as mentioned above.

The enzymes may be in any form. For example, the enzyme regulated may be in aqueous, aqueous-based or organic solutions. The enzyme may also be in other matrices, such as a gel. Also, the enzyme may be in unbound or bound form, and even in bound form in cells, or in living cells, such as vegetables and other tissue.

In using the present invention to regulate bound enzymes, for example, the present invention may be used in numerous types of applications. For example, the bound enzymes may be in use in batch reactors, continuous-flow-stirred-tank reactors, column reactors, such as a packed-bed reactor, or even fluidized bed reactors.

Further, the use of bound enzymes in cells is advantageous where the cost of enzyme extraction and purification is prohibitive, or where the enzyme is unstable when removed from its native environment. For example, L-citrulline may be prepared using immobilized cells of *Pseudomonas putida* and urocanic acid may be prepared using immobilized cells of *Achromobacter liquidium*.

Moreover, the present invention may also be used to regulate enzyme activity in conjunction with enzyme electrodes, such as an electrode used to measure glucose using glucose oxidase.

The present invention may be used advantageously whenever the regulation of enzyme activity in a controllable and predictable manner is desired.

In order to further describe the present invention, each of the six basic classes of enzymes will now be discussed in more detail.

I. Oxidoreductases

Generally, oxidoreductase enzymes are strongly inhibited by noble gases. However, the amount of inhibition varies from one noble gas to another, and from one noble gas mixture to another.

Xenon exhibits the largest effect on the rate of oxidoreductase reactions and depresses the final equilibrium of the reactions. The other noble gases all inhibit the reaction rate and depress the final equilibrium of the reaction to a lesser extent, depending both upon their solubility and molecular properties. Krypton has a somewhat lesser effect than xenon, and argon is very active at low temperatures. Thus, in accordance with the present invention, different gas mixtures may be used to optimize oxidoreductase activity depending upon whether ambient or refrigerated temperatures are used.

By using one or more noble gases or mixtures thereof, variable oxidoreductase inhibitions obtained depending on the precise gas or mixture, substrate, temperature and gas pressure used.

II. Transferases

Generally, transferase enzymes are generally inhibited. For example, aminotransferases are inhibited and transpeptidases are inhibited by the noble gases or mixtures thereof.

Generally, krypton exhibits the largest inhibitory or effect with some variation depending upon the subclass of transferase which is subjected thereto. Neon, by contrast, exhibits both the lowest inhibitory or enhancing effect depending upon the subclass of transferase used.

III. Hydrolases

Generally, all hydrolases are strongly enhanced by noble gases or mixtures thereof.

Notably, xenon exhibits the largest enhancing effect, whereas krypton exhibits the least such effect.

However, if desired, hydrolases may also be inhibited.

IV. Lyases

In general, lyase enzymes are strongly or moderately enhanced by noble gases or mixtures thereof. However, some gases inhibit lyase enzymatic activity under suboptimal conditions.

Xenon exhibits the largest enhancing effect, whereas argon exhibits the least such effect.

V. Isomerases

In general, isomerase enzymes are either strongly or moderately enhanced by noble gases or mixtures thereof.

However, argon and mixtures containing the same can be induced to inhibit enzyme activity at higher temperatures.

VI. Ligases (Synthetases)

In general, ligase enzymes are strongly enhanced by noble gases or mixtures thereof.

In order to clarify the protocol used in measuring the effect of one or more noble gases on enzymatic activity in accordance with the present invention, the following description of a typical and exemplary experimental protocol is provided:

General Protocol

Solution preparation: Optimized w/v solutions are prepared by diluting the enzyme (units/ml) and the substrate (µg/ml) in appropriate buffer (optimized pH and molarity for enzymes). The solutions are used for gas experiments at once to avoid loss of activity. Various enzyme and substrate concentrations and inhibitors may be employed. Physical parameters are varied as required.

Spectrophotometric equipment: The experimental runs are performed with a Perkin-Elmer Lambda 6 UV/VIS spectrophotometer, temperature controlled, connected to an IBM PS/2 30 personal computer. The IBM is loaded with two software packages (PECSS or UVDM to record and view spectra, modified ENZFITTER and Grafit to do kinetic studies).

Full range spectra: The taking of full range spectra of enzyme and substrate species as well as completed reaction mixes allows the determination of a suitable wavelength to follow the enzymatic reaction (wavelength corresponding to the main absorbance peak), on a real-time basis. Absorbent species are measured and blanked. Various chromogenic substrates may be used, and in certain circumstances, chromogenic reactions may be coupled to the enzyme reaction under study.

Dilution series: Dilution series are run to find the optimal enzyme/substrate ratio for proceeding with gas experiments. Reactions are run at optimal conditions, then with super- and suboptimal substrate ranges, then with various inhibitors.

Preparation of silicone sealed cuvets: 1-cm lightpath acrylic or quartz cuvets are stoppered with silicone rubber sealer. The silicone is allowed to cure for 48 hours in order to obtain gas-tight cuvets. Cuvets are purged with air to remove any chemical gas contaminants as measured by GC/MS, and tested for leaks.

Preparation of samples: Cuvets are filled with 2 ml of substrate solution by means of a gas-tight syringe. Gas-tight serum vials are filled with enzyme and solvent. Sufficient gas is consecutively bubbled in the cuvets and serum vials, with a 1-hr wait between injections to maximize equilibration of gas. All syringes and dead spaces are purged before filling with the appropriate gas. The amount of gas used has been measured sufficient to saturate the solution required.

Controls: All possible interfering parameters are controlled including T, P, other gases, air leaks, materials, variation in gas and reagent quality, pH. Repetitions to significance are conducted.

Spectrophotometric time-drive, reaction rate, and kinetic analyses: cuvets and serum vials are saturated with gas 40 minutes before the run. A gas-filled syringe is used to retrieve 0.5 ml of enzyme solution to avoid air contact. The 0.5 ml syringe injections of enzyme are made simultaneously to effect a common starting time to for the samples. 7 gases (air, $O_2$, $N_2$, Ne, Ar, Kr, Xe) are run at various temperatures each (from 0° to 60°). Changes in the rate or final equilibrium of the reaction versus ambient air are recorded. Comparison is also made with added oxygen, and with deoxygenation. Some samples are also prepared under pressure.

The Complete Experiment Protocol

In a complete experiment, an enzyme at optimal pH and buffering salt concentration is reacted with 5 substrate concentrations in solution with noble gas at 1 atm. (saturated solution), at 10% and 50% of saturation, and at 1.5 and 2 atm. and at least one much higher pressure, and with supplemental oxygen equivalent to 10%, 20%, and 50% of total gas at 1 and 2 atm. total pressure, at each temperature from 0°–65° C. in 5° increments, using $N_2$, $O_2$, Ar, Ne, Kr, Xe, Air, and occasionally other gases, and using decile mixtures of the above gases, plus the enzyme is exposed to very high pressures in a hydrostatic control. Controls are also run after evacuation of solution by vacuum. The reaction is monitored colorimetrically in a scanning spectrophotometer in real-time, and the signals are treated mathematically to obtain rate and yield differences. Sample numbers are constant and sufficient to ensure significance of results. All parameters are independently controlled and measured, and more complex experiments are occasionally carried out.

Data are obtained in the form of real-time product formation plots (standard rate curves), one for each sample cuvette, which are overlaid under standard procedure to yield one overlay for each 6–12 cuvette experiment. Such an overlay is appended. The x-y data point tables which make up these curves plus all machine parameters are also produced. These data may be further transformed to calculate differences between curves, differences between yields, differences between rates, or other logical comparisons. These are calculated using several separate software programs which utilize simple or complex ordinary mathematical expressions, linear and nonlinear regression curve fitting, log normal transformations, enzymatic rate calculations (Michaelis-Menten, Eadie-Hofstee, Lineweaver-Burk), and time-dependent multivariate analyses.

In order to more completely describe the present invention, reference will now be made to certain examples which are provided solely for purposes of illustration and are not intended to be limitative.

Class I. Oxidoreductases (EC1)

EXAMPLE 1

Tyrosinase; at 25° C. and optimal reaction conditions, simple saturation of solution with gas:

| noble gas or mixture | effect |
| --- | --- |
| Xe | −73% (Inhibition) |
| Kr | −73% |
| Ar | −60% |
| Ne | −46.7% |
| 90:10 Xe:Kr mix | −50% |
| Ar:Xe 99:1 | −70% |

EXAMPLE 2

Glucose oxidase:

| noble gas or mixture | effect |
| --- | --- |
| Xe | −91.6% (Inhibition) |
| Kr | −92.7% |
| Ar | −85.8% |
| Ne | −61.7% |
| Maxima for class: | |
| Xe | −95% (Inhibition) |
| Kr | −91% |
| Ar | −91% |
| Ne | −85% |

Notably, the above results are dependent upon the temperature and substrate concentration.

Class II. Transferases (EC2)

EXAMPLE 3

Gamma-glutamyl transpeptidase:

| noble gas or mixture | effect |
| --- | --- |
| Xe | −7% (Inhibition) |
| Kr | −8% |
| Ar | −5% |
| Ne | −3% |

EXAMPLE 4

Aspartate aminotransferase:

| noble gas or mixture | effect |
|---|---|
| Xe | −17% (Inhibition) |
| Kr | −82% |
| Ar | −17% |
| Ne | −12% |

Class III. Hydrolases (EC3)

EXAMPLE 5

Beta-D-glucosidase:

| noble gas or mixture | effect |
|---|---|
| Xe | +40% (Enhancement) |
| Kr | +14% |
| Ar | +16% |
| 90:10 Xe:Kr mix | +18% |

The above results are dependent upon temperature, substrate concentration, and type of substrate. With the addition of different competing substrates, enhancements of up to 200% were obtained using xenon.

Class IV. Lyases (EC4)

EXAMPLE 6

Results are variable with temperature and [E/S]. For the citrate synthetase complex reaction:

|  | 35° C. | 25° C. | 10° C. |
|---|---|---|---|
| Xe | +32 | 0 | +18 |
| Kr | +32 | +6 | +37 |
| 90:10 | 0 | +16 | −32 |
| Ar | −15 | −10 | +25 |
| Ne | −14 | +9 | +11 |
| N₂ | −17 | −25 | −6 |

EXAMPLE 7

For phenylalanine ammonia lyase with optimized enzyme concentration:

| Xe | +18 | +3 | +5 |
|---|---|---|---|
| Kr | +7 | +4 | +4 |
| 90:10 | +5 | +2 | +1 |
| Ar | +6 | +1 | +3 |
| Ne | −2 | +6 | −6 |
| N₂ | +19 | 0 | +6 |

EXAMPLE 8

For phenylalanine ammonia lyase with suboptimal enzyme concen.:

| Xe | +14 | +8 | +11 |
|---|---|---|---|
| Kr | +3 | +18 | +14 |
| 90:10 | +5 | +8 | +6 |
| Ar | −1 | +1 | +6.5 |
| Ne | +15 | 0 | +6 |
| N₂ | 0 | 0 | +12 |

Class V. Isomerases (EC5)

EXAMPLE 9

Triosephosphate isomerase, 10° C.:

| noble gas or mixture | effect |
|---|---|
| Xe | +24% (Enhancement) |
| Kr | +12 |
| Ar | +8% (but −37% inhibition at 25° C. |
| Ne | +4% |
| 90:10 Xe:Kr | +6.3% |

EXAMPLE 10

Phosphoglucose isomerase

| noble gas or mixture | effect |
|---|---|
| Xe | +186% (−61% stressed) |
| Kr | +206.4% |
| Ar | +232.5% |
| Ne | +107% (−45% stressed) |

Stressed refers to conditions of nonoptimal substrate concentration or temperature.

Class VI. Ligases (Synthetases) (EC6)

These enzymes are enhanced but quite variable; extremely active site specific.

Maximum observed enhancement vs maximum observed inhibition (depending upon temperature):

EXAMPLE 11

Acetyl S-CoA synthetase

In a coupled complex reaction sequence including hydrolytic enzymes:

| Xe | +18.3%/−25.0% |
|---|---|
| Kr | +16.1%/−34.6% |
| Ar | +67.7%/+34.6% |
| Ne | +2.3%/−21.9% |
| 90/10 | +16.1%/−38.5% |
| N₂ | +31.2%/−39.5% |

EXAMPLE 12

As an isolated reaction:

| Xe | +15.4%/−39.5% |
|---|---|
| Kr | +5.0%/−52.6% |
| Ar | +75.4%/−27.6% |
| 90/10 | +5.0%/−57.9% |
| N₂ | +35.7%/−118.7% |

In general, at higher temperatures, inhibition occurs. At low temperatures, enhancement occurs. Nitrogen usually has a much lesser effect than noble gases except at superoptimal temperatures. We are seeing noble gases enhancing this reaction towards optimal yields and rates under conditions which were otherwise suboptimal for the reaction. We are seeing mixed results under optimal conditions which depends upon the gas used.

The present invention will now be further described by reference to further examples which are provided for purposes of illustration and are not intended to be limitative.

Tyrosinase Catalyzed Reaction

Tyrosinase (Monophenol, dihydroxyphenylalanine: oxygen oxidoreductase; EC 1.14.18.1) is a monophenol monooxygenase which catalyzes the reaction of ortho-diphenols to ortho-quinones.

Tyrosinase is important in fruit browning and food product spoilage.

Experimental Protocol

1. Solution preparation: 10% w/v solutions are prepared by diluting the enzyme (units/ml) and the substrate (µg/ml) in Sodium Phosphate buffer (pH 6.85, optimized pH for enzymes). The solutions are stored in refrigerator (0°–5° C.) and used for gas experiments within 2 or 3 days to avoid loss of activity.

2. Spectrophotometric equipment: The experimental runs are performed with a Perkin-Elmer Lambda 6 UV/VIS spectrophotometer connected to an IBM PS/2 30 personal computer. The IBM is loaded with two software packages (PECSS to record and view spectra, ENZFITTER to do kinetic studies).

3. Full range spectra: The taking of full range spectra of E, S, and E+S allows the determination of a suitable wavelength to follow the enzymatic reaction (wavelength corresponding to the main absorbance peak).

4. Dilution series: Dilution series E vs S, and S vs E are run to find the optimal [E]/[S] ratio for proceeding with gas experiments. According to absorbance readings, the best of the two blanks (buffer +E or buffer +S) is chosen.

5. Preparation of silicone sealed cuvets: 1-cm lightpath acrylic disposable cuvets are stoppered with clear silicone rubber sealer. The silicone is allowed to cure for 48 hrs in order to obtain gas tight cuvets.

6. Preparation of run samples: Acrylic cuvets are filled with 2 ml of substrate solution by means of a gas tight syringe. Gastight serum vials are filled with enzyme. 3×10 cc of gas are consecutively bubbled in the cuvets and serum vials, with a 1-hr wait between injections. This represents a 10× displacement of dead volume while maximizing equilibration of gas. All syringes and dead spaces are purged before filling with the appropriate gas. After the third 10 cc injection, the cuvets and serum vials are left overnight under two 10 cc syringes filled with the appropriate gas in refrigerator at 0°–5° C.

7. Controls: All possible interfering parameters are controlled, including T, P, other gas, air leaks, materials, variation in gas and reagent quality, pH. Repetitions to significance are conducted.

8. Spectrophotometric runs: The cuvets and serum vials are filled with 10 cc of gas 40 min before the run. A gas-filled syringe is used to retrieve 0.5 ml of enzyme solution to avoid air contact. The 0.5 ml syringe injections of enzyme are made simultaneously to effect a common starting time $t_0$ for the samples. Seven gases (air, $O_2$, $N_2$, Ne, Ar, Kr, Xe) are run at five temperatures each (15° C., 20° C., 25° C., 30° C., 35° C.). Changes in the rate or final equilibrium of the reaction versus ambient air are recorded.

2. REAGENTS

Tyrosinase (Sigma Chemical Co., St Louis, Mo.):
Catalog No. T-7755 (Lot 48F-9610)
Monophenol monooxygenase; Polyphenol oxidase; Catechol oxidase; Monophenol, dihydroxyphenylalanine: oxygen oxidoreductase;
EC 1.14.18.1)
from Mushroom
25,000 units
12 mg solid
2,200 units/mg solid (Tyrosinase activity)
Tyrosinase unit definition: one unit will cause an increase in $A_{280}$ of 0.001 per min at pH 6.5 at 25° C., using L-tyrosine as substrate. Reaction volume of 3 ml (1 cm light path)
Stored desiccated below 0° C.

L-Tyrosine (Sigma Chemical Co., St Louis, Mo.):
Catalog No. T-3754 (Lot 48F-0833)
L-3-[4-Hydroxyphenyl]alanine
Free Base (pfs) Crystalline
Anhydrous Mol. Wt. 181.2
Stored at room temperature (25° C.)

Sodium Phosphate Monobasic (E K Industries, Addison, Ill.)
Catalog No. 8680
$NaH_2PO_4.H_2O$
Reagent Crystals
FW 137.99

Sodium Phosphate Dibasic (E K Industries, Addison, Ill.)
Catalog No. 8720
$Na_2HPO_4$
Anhydrous
FW 141.96

Deionized water $H_2O$ (Barnstead NANOpure II)

3. SOLUTION PREPARATION

Sodium Phosphate Buffer pH 6.85 (25° C.):
138 g $NaH_2PO_4.H_2O$
142 g $Na_2$ $HPO_4$
in 20 l D.I. $H_2O$
Stored at room temperature (25° C.) in a plastic carboy Tyrosinase solution (100 µg/ml; 208 units/ml; 2.08 units/µg):
10% w/v in Na Phosphate buffer
Mix several times by inversion to dissolve content
Stored in refrigerator [0°–5° C.] in 125 ml HDPE bottle wrapped in aluminum foil (to avoid light degradation)

L-Tyrosine solution (100 µg/ml):
10% w/v in Na Phosphate buffer
Magnetic stirring (25° C., 30 min)
Stored in refrigerator [0°–5° C.) in 250 ml amber glass bottle

4. GAS ATMOSPHERES

Air (ambient)
Argon (Alphagaz, research grade)
Krypton (Alphagaz, research grade, minimum purity 99.995% [ppm])
Neon (Alphagaz, research grade, minimum purity 99.999% [ppm])
Nitrogen (Alphagaz, research grade, minimum purity 99.9995% [ppm]).
Oxygen (Alphagaz, research grade, minimum purity 99.997% (ppm]).
Xenon (Alphagaz, research grade, minimum purity 99.995% [ppm])

5. INSTRUMENTS AND MATERIALS 5.1. Instruments
Perkin-Elmer Lambda 6 UV/VIS Spectrophotometer (narrow-bandwidth spectrophotometer) equipped with automatic transport thermoelectric five-cell holders (5×5 Sample and Reference Cell Holder, Model C 005-0515)

Perkin-Elmer Lambda Accessory Interface (Model C691-0000)

Perkin-Elmer Digital Controller (Model C 570-0701)

Perkin-Elmer Temperature Programmer (Model C 570-0710)

IBM PS/2 30 personal computer

Epson EX800 printer

Software

IBM DOS (Disk Operating System Version 3.30, Boca Raton, Fla.)

PECSS (Perkin-Elmer Computerized Spectroscopy Software, Norwalk, Conn.)

ENZFITTER (A Non-linear Regression Data Analysis Program, Elsevier-BIOSOFT, Cambridge, UK)

PIZAZZ PLUS (Print Enhancement Software, APTEC, Pepperell, Mass.)

Mettler AE100 Balance

Weighing range: 0 . . . 109 g

Readability: 0.1 mg

Barnstead NANOpure II cartridge deionization system
Tokyo Rikakikai Co. Micro Tubing Pump MP-3 (for the Perkin-Elmer water cooled cells)

5.2. Materials 100, 200 ml volumetric flasks FISHERbrand Acrylic Cuvets (Standard Type/Methacrylate/UV Grade/ Disposable): 1-cm lightpath, square cuvets capable of holding 3 ml of solution 100% Silicone Rubber Sealer (Clear)

3 ml Rubber Capped Serum Vials 1 ml in 1/100 ml Disposable Serological Pipets 1 cc in 1/100 cc Disposable Tuberculin Syringes 10 cc in 1/5 cc Disposable Syringes 20G1½" Disposable Needles

6. DEVELOPMENT OF TECHNIQUE 6.1. Initial observations

Full range scans (900–190 nm) were run with tyrosinase, L-tyrosine, and the final products of the enzymatic reaction.

6.1.1. Experimental set up

PARAM:
Absorbance
Slit 1 nm
Scan speed 1,500 nm/min
Response time 1 s
Autosave Yes AZERO: Background correction (900–190 nm)

SCAN: Data interval 1.0 nm

Temperature: ambient (26° C.), temperature programmer off 6.1.2. Full range scans

[900–190 nm] scan of tyrosinase (FIG. 1):
Sample=2.5 ml tyrosinase (100 µg/ml)
Blank=2.5 ml Sodium Phosphate buffer
Filename: T775501.SP (900–190 nm] scan of L-tyrosine (FIG. 2):
Sample=2.5 ml L-tyrosine (100 µg/ml)
Blank=2.5 ml Sodium Phosphate buffer
Filename: T375401.SP

[900–190 nm] scan of the final products (FIG. 3–):
Sample=2 ml L-tyrosine (100 µg/ml)+0.5 ml tyrosinase (100 µg/ml) after a time reaction of 20 minutes Blank=2 ml L-tyrosine (100 µg/ml)+0.5 ml Na Phosphate buffer
Filename: TCEB0081.SP 6.1.3. Determination of the main absorbance peaks For this purpose, the graphics cursor (Home key) was used.

Tyrosinase: peak absorbance at 275 nm (protein)

L-Tyrosine: peak absorbance at 275 nm

The reaction final products: peak absorbance at 480 nm and 305 nm 6.1.4. Determination of a suitable wavelength to follow the reaction The overlay of the three full range spectra (FIG. 5) suggests optimal observation of enzymatic oxidoreduction of L-tyrosine at either 480 or 305 nm.

6.1.5. Determination of an appropriate [E]/[S] ratio:

|  | T-3754 (100 µg/ml) (ml) | T-7755 (100 µg/ml) (ml) | Na Phos. buffer (ml) | Final [E] (100 µg/ml) |
| --- | --- | --- | --- | --- |
| Sample 5 | 2 | 0.1 | 0.4 | 20 |
| Sample 4 | 2 | 0.2 | 0.3 | 40 |
| Sample 3 | 2 | 0.3 | 0.2 | 60 |
| Sample 2 | 2 | 0.4 | 0.1 | 80 |
| Sample 1 | 2 | 0.5 | 0.0 | 100 |

Timedrives were run using the cell programmer (CPRG) command, which records time drive data of up to 5 cells simultaneously.

| Wavelength 480 nm: overlay (FIG. 6) 45 points, 60 s intervals ===> 45 min run | | |
| --- | --- | --- |
| TCEB0091.SP | [enz.] = 100 µg/ml | Cell 1 |
| TCEB0092.SP | [enz.] = 80 µg/ml | Cell 2 |
| TCEB0093.SP | [enz.] = 60 µg/ml | Cell 3 |
| TCEB0094.SP | [enz.] = 40 µg/ml | Cell 4 |
| Wavelength 305 nm: overlay (FIG. 7). 60 points, 60 s intervals ===> 1 hr run | | |
| TCEB0101.SP | [enz.] = 100 µg/ml | Cell 1 |
| TCEB0102.SP | [enz.] = 80 µg/ml | Cell 2 |
| TCED0103.SP | [enz.] = 60 µg/ml | Cell 3 |
| TCEB0104.SP | [enz.] = 40 µg/ml | Cell 4 |
| TCEB0105.SP | [enz.] = 20 µg/ml | Cell 5 |

Conclusion

The optimal conditions are [E]/[S] (100 µg/ml)/(100 µg/ml), the changes in absorbance being observed at 305 nm.

6.2.1. Preliminary experiments 6.2.1. Preparation of samples and references

Xenon saturated samples (see sampling procedure)

Air samples: acrylic cuvets filled with 2 ml of substrate T-3754 with a i ml pipet, and capped with plastic cap. This procedure was later changed from the use of plastic caps to using silicone-sealed cuvets. No significant differences were found.

References (blanks): acrylic cuvets capped with plastic cap.

B1: 2 ml T-3754 (100 µg/ml)+0.5 ml Na Phos. buffer

B2: 2 ml Na Phos. buffer+0.5 ml T-7755 (100 µg/ml)

6.2.2 Timedrives at 305 nm

Blank B1:
AIR sample: filename=TCEB0114.SP
XENON sample: filename=TCEB0115.SP

Blank B2:
AIR sample: filename=TCEB0116.SP
XENON sample: filename=TCEB0117.SP

The L-tyrosine blank (B1) is found to depress absorbance readings, so the tyrosinase blanked experiment (B2) is used in preference.

These 4 timedrives show an optimal inhibition curve for xenon. With the later runs (6.3.7. and 7.2.) the L-tyrosine solution has decayed with time, which induces a depletion in absorbance reading.

6.3. Development of technique

6.3.1. Step 1: preparation of silicone-sealed cuvets

Acrylic disposable cuvets are stoppered with clear silicone rubber sealer. The silicone is allowed to dry for 24 hrs. After 24 hrs, we have gas-tight acrylic cuvets. These were tested for bubbling under water.

6.3.2. Step 2: substrate sampling procedure

Silicone-sealed acrylic cuvets are filled with 2 ml of substrate by means of a 1 cc syringe (in 1/100 cc).

To obtain accurate sampling, the syringe is tapped and vacated of air (which interferes with the substrate solution volume).

The filled cuvets are stored in refrigerator (0°–5° C.).

The blank B1 (2 ml T-3754+0.5 ml Na Phosphate buffer) is prepared in a plastic capped cuvet. This was changed later to the use of silicone-sealed cuvets.

6.3.3. Step 3: enzyme sampling procedure

Serum vials are filled with 2 ml of enzyme by means of a 1 ml pipet (in 1/100 ml), capped with a rubber septum and crimp-sealed with an aluminum cap. Serum vials are gas-tight.

The filled serum vials are stored in refrigerator (0°–5° C.).

6.3.4. Step 4: gas saturation procedure (ARGON, KRYPTON, NEON, OXYGEN, XENON)

3×10 cc of gas are consecutively bubbled in the silicone-sealed cuvets and serum vials (T-3754, T-7755), with a 1-hr wait between injections. This represents a 10× displacement of dead volume while maximizing equilibration of gas.

All syringes and deadspaces are purged before filling with the appropriate gas. After the third 10 cc injection, the silicone-sealed cuvets and serum vials are left overnight under two 10 cc syringes filled with the appropriate gas in refrigerator at 0°–5° C.

6.3.5. Note

The air samples (both enzyme and substrate) do not undergo any bubbling. The acrylic cuvet is stoppered with a regular vinyl cap (non gas-tight). This procedure was later changed to the use of silicone-sealed cuvettes. Multiple comparisons with sealed air-bubbled treatments show no difference between the two methods.

6.3.6. Step 5: spectrophotometric runs a. The silicone-sealed cuvets, serum vials and plastic capped cuvets are removed from the refrigerator. This procedure is later changed (see 7.1.5.)

b. The silicone-sealed cuvets and serum vials are filled with 10 cc of gas and left at room temperature (26° C.) under two 10 cc syringes.

c. The cuvets are placed in the cell holder and allowed to equilibrate in temperature with the cell holder for 10 min.

d. A 1 cc syringe is filled with the appropriate gas and used to retrieve 0.5 ml of enzyme solution from a serum vial, this to avoid introduction of air in the vial while sampling the enzyme.

e. Run:

The sequential 0.5 ml syringe injections of enzyme into the cuvets are performed as quickly as possible from cell 5 to cell 1 (delay x=2 sec). This procedure is later changed to concurrent injection.

6.3.7. Spectrophotometric runs: Timedrives at 305 nm

| 60 points, 60 s intervals ===> 1 hr run | | |
|---|---|---|
| Filename | Gas | Cell no. |
| Run 1: T1 = 15° C. ($T_S = T_R$ = 15.1° C.) | | |
| B1T1G2.SP | Neon | Cell 2 |
| B1T1G3.SP | Argon | Cell 3 |
| B1T1G4.SP | Krypton | Cell 4 |
| B1T1G5.SP | Xenon | Cell 5 |
| Run 2: T1 = 15° C. ($T_S = T_R$ = 15.1° C.) | | |
| B1T1G6.SP | Air | Cell 1 |
| B1T1G7.SP | Oxygen | Cell 2 |
| Run 3: T2 = 20° C. ($T_S = T_R$ = 20° C.) | | |
| B1T2G1.SP | Air | Cell 1 |
| B1T2G2.SP | Neon | Cell 2 |
| B1T2G3.SP | Argon | Cell 3 |
| B1T2G4.SP | Krypton | Cell 4 |
| B1T2G5.SP | Xenon | Cell 5 |
| Run 4: T2 = 20° C. ($T_S = T_R$ = 20° C.) | | |
| B2T2G6.SP | Oxygen | Cell 1 |
| Run 5: T3 = 25° C. ($T_S = T_R$ = 24.9° C.) | | |
| B1T3G1.SP | Air | Cell 1 |
| B1T3G2.SP | Neon | Cell 2 |
| B1T3G3.SP | Argon | Cell 3 |
| B1T3G4.SP | Krypton | Cell 4 |
| B1T3G5.SP | Xenon | Cell 5 |
| Run 6: T3 = 25° C. ($T_S = T_R$ = 24.9° C.) | | |
| B1T3G6.SP | Oxygen | Cell 1 |
| Run 7: T4 = 30° C. ($T_S = T_R$ = 29.9° C.) | | |
| B1T4G1.SP | Air | Cell 1 |
| B1T4G2.SP | Neon | Cell 2 |
| B1T4G3.SP | Argon | Cell 3 |
| B1T4G4.SP | Krypton | Cell 4 |
| B1T4G5.SP | Xenon | Cell 5 |
| Run 8: T4 = 30° C. ($T_S = T_R$ = 29.9° C.) | | |
| B1T4G6.SP | Oxygen | Cell 1 |
| Run 9: T5 = 35° C. ($T_S = T_R$ = 34.9° C.) | | |
| B1T5G1.SP | Air | Cell 1 |
| B1T5G2.SP | Neon | Cell 2 |
| B1T5G3.SP | Argon | Cell 3 |
| B1T5G4.SP | Krypton | Cell 4 |
| B1T5G5.SP | Xenon | Cell 5 |
| Run 10: T5 = 35° C. ($T_S = T_R$ = 34.9° C.) | | |
| B1T5G6.SP | Oxygen | Cell 1 |

7.3. Graphic results
Timedrives overlay/Temperature—appended pages
Timedrives overlay/Gas—appended pages

7. FINAL PROCEDURE

7.1. Final experimental protocol

7.1.1 Step 1 preparation of silicone-sealed cuvets

Same as 6.3.1. but the silicone is allowed to cure for 48 hrs in order to get rid of acetic acid vapors, which could interfere with the enzyme inhibition. This is confirmed by assay.

7.1.2. Step 2: substrate sampling procedure

Same as 6.3.2.

The blank B2 (2 ml Na Phosphate buffer +0.5 ml T-7755) is prepared according to the same procedure (in a silicone-sealed cuvet) but does not undergo the gas saturation step (7.1.4.).

Control checks show no absorbance by any of the gases within working absorbance range.

7.1.3. Step 3: enzyme sampling procedure

Same as 6.3.3.

7.1.4. Step 4: gas saturation procedure (AIR, ARGON, KRYPTON, NEON, NITROGEN, OXYGEN, XENON)

3×10 cc of gas are bubbled in the silicone-sealed cuvets and serum vials (T-3754, T-7755), with an interval of 20 min (at 0°–5° C.) between each gas injection.

After the third 10 cc injection, the cuvets and serum via are left overnight under two 10 cc syringes filled with the appropriate gas in refrigerator at 0°–5° C.

7.1.5 Step 5: spectrophotometric runs a. The silicone-sealed cuvets are removed from the refrigerator 40 min before the experimental run, filled with 10 cc of gas and left at room temperature (26° C.) under two 10 cc syringes.

b. The serum vials are removed from the refrigerator 25 min before the experimental run, filled with 10 cc of gas and put back in the refrigerator under two 10 cc syringes.

c. 15 min before the run, the 10 cc syringes (and needles) are removed from the silicone-sealed cuvets. The cuvets are placed in the cell holder and allowed to equilibrate in temperature with the cell holder for 10 min.

d. 5 min before the run, a 1 cc syringe is filled with the gas and used to retrieve 0.5 ml of enzyme solution in the serum vials, this to avoid introduction of air in the vial while sampling the enzyme.

e. Run:

The silicone-sealed cuvets are briefly removed from the cell holder and tapped to suppress gas bubbles that may form while the cuvets are warming up (this is especially true at 30° and 35° C.), and replaced in the cell holder.

The 0.5 ml syringe injections of enzyme are made simultaneously to effect a common starting time $t_0$ for the samples.

7.2. Spectrophotometric runs: Timedrives at 305 nm

| 200 points, 18 s intervals ===> 1 hr run | | |
|---|---|---|
| Filename | Gas | Cell no. |
| 7.2.1. Run 1: T1 = 15° C. ($T_S = T_R = 15.1°$ C.) | | |
| B2T1G1.SP | Air | Cell 1 |
| B2T1G2.SP | Neon | Cell 2 |
| B2T1G3.SP | Argon | Cell 3 |
| B2T1G4.SP | Krypton | Cell 4 |
| B2T1G5.SP | Xenon | Cell 5 |
| 7.2.2. Run 2: T1 = 15° C. ($T_S = T_R = 15.1°$ C.) | | |
| B2T1G6.SP | Air | Cell 1 |
| B2T1G7.SP | Oxygen | Cell 2 |
| B2T1G8.SP | Nitrogen | Cell 3 |
| 7.2.3. Run 3: T2 = 20° C. ($T_S = T_R = 19.9°$ C.) | | |
| B2T2G1.SP | Air | Cell 1 |
| B2T2G2.SP | Neon | Cell 2 |
| B2T2G3.SP | Argon | Cell 3 |
| B2T2G4.SP | Krypton | Cell 4 |
| B2T2G5.SP | Xenon | Cell 5 |
| 7.2.4. Run 4: T2 = 20° C. ($T_S = T_R = 19.9°$ C.) | | |
| B2T2G6.SP | Air | Cell 1 |
| B2T2G7.SP | Oxygen | Cell 2 |
| B2T2G8.SP | Nitrogen | Cell 3 |
| 7.2.5. Run 5: T3 = 25° C. ($T_S = T_R = 24.9°$ C.) | | |
| B2T3G1.SP | Air | Cell 1 |
| B2T3G2.SP | Neon | Cell 2 |
| B2T3G3.SP | Argon | Cell 3 |
| B2T3G4.SP | Krypton | Cell 4 |
| B2T3G5.SP | Xenon | Cell 5 |
| 7.2.6. Run 6: T3 = 25° C. ($T_S = T_R = 24.9°$ C.) | | |
| B2T3G6.SP | Air | Cell 1 |
| B2T3G7.SP | Oxygen | Cell 2 |
| B2T3G8.SP | Nitrogen | Cell 3 |
| 7.2.7. Run 7: T4 = 30° C. ($T_S = T_R = 29.9°$ C.) | | |
| B2T4G1.SP | Air | Cell 1 |
| B2T4G2.SP | Neon | Cell 2 |
| B2T4G3.SP | Argon | Cell 3 |
| B2T4G4.SP | Krypton | Cell 4 |
| B2T4G5.SP | Xenon | Cell 5 |
| 7.2.8. Run 8: T4 = 30° C. ($T_S = T_R = 29.9°$ C.) | | |
| B2T4G7.SP | Air | Cell 2 |
| B2T4G8.SP | Oxygen | Cell 3 |
| B2T4G9.SP | Nitrogen | Cell 4 |
| 7.2.9. Run 9: T5 = 35° C. ($T_S = T_R = 34.9°$ C.) | | |
| B2T5G1.SP | Air | Cell 1 |
| B2T5G2.SP | Neon | Cell 2 |
| B2T5G3.SP | Argon | Cell 3 |
| B2T5G4.SP | Krypton | Cell 4 |
| B2T5G5.SP | Xenon | Cell 5 |
| 7.2.9. Run 10: T5 = 35° C. ($T_S = T_R = 34.9°$ C.) | | |
| B2T5G6.SP | Air | Cell 1 |
| B2T5G7.SP | Oxygen | Cell 2 |
| B2T5G8.SP | Nitrogen | Cell 3 |

7.3. Graphic results

Timedrives overlay/Temperature—appended pages
Timedrives overlay/Gas—appended pages

7.4. Enzyme kinetics: ENZFITTER

From the above results obtained from the tyrosinase-L-tyrosine reaction, the following conclusions may be drawn.

Xenon significantly inhibits the rate and depresses the final equilibrium of the tyrosinase-L-tyrosine reaction. Moreover, the other noble gases all inhibit the rate and depress the final equilibrium of the reaction to a lesser extent, depending both on their solubility and molecular properties. Krypton generally has a similar but smaller effect as xenon, while argon is surprisingly active at low temperatures.

Further, the effects of oxygen depletion can be controlled through the use of nitrogen. When compared with argon, nitrogen is found to lack the physical ability for active site interaction. It appears that argon is more active relative to nitrogen. This also appears to be true for other enzyme classes.

As differences in solubility can explain only a portion of the observed inhibitions, active site interactions or induced protein conformational changes must occur.

Kinetic experiments are included hereinbelow.

High Pressure Experiments

Experiments were conducted in pressure cells pressurized with additional test gas after solution was already saturated, at 2 atmospheres or at 3 atmospheres in real-time, or after pressurizing in a 1-liter cylinder for 1 hour or ~24 hours at 30.6 atmospheres and at 100 atmospheres.

The following experimental procedures were used.

Protocol

Effects of High Pressure on Enzymes.

Theory

We will introduce enzymes to high pressures and determine their activity. High pressures should inhibit the activity of the enzymes.

Enzyme

Tyrosinase (SIGMA No. T-7755) (Monophenol monooxygenase; Polyphenol oxidase;
  Catechol oxidase; Monophenol, dihydroxyphenylalanine: oxygen oxidoreductase;
  EC 1.14.18.1)
From Mushroom
Tyrosinase Unit Definition
  One unit will cause an increase in $A_{280}$ of 0.001 per min at pH 6.5 at 25° C. in 3 mL reaction mix containing L-tyrosine.
  Tyrosinase activity: 3870 U/mg solid
  7.1 mg solid→27,440 Units
  Stored desiccated below 0° C.
Substrate
  L-Tyrosine (SIGMA No. T-3754)
  L-3-[4-Hydroxyphenyl]alanine
  Free Base (pfs) Crystalline
  Anhydrous Mol. Wt. 181.2
  Stored at room temperature (25° C.)
Enzyme
  β-D-Glucosidase (SIGMA No. G-4511)
  (Emulsin; β-D-Glucoside glucohydrolase EC 3.2.1.21)
  From Almonds
Unit Definition
  One unit will liberate 1.0 μmole of glucose from salicin per min at pH 5.0 at 37° C.
  Activity: 22 U/mg solid
  12 mg solid→264 Units
  Stored desiccated at 0°–5° C.
  Lot#49F-4021
Substrate
  p-Nitrophenyl-β-D-Glucopyranoside (SIGMA No. N-7006)
  Crystalline
  Contains 2.4% solvent
  Anhydrous Mol. Wt. 301.3
  Stored desiccated below 0° C.
  Lot#129F-5057
Trial 1: Apr. 10, 1991–Apr. 11, 1991
Gasses
  1. Air
  2. $N_2$
Pressures
  1. 30.6 atm (450 psi)
  2. 100.0 atm (1470 psi)
Controls
  Control A: enzyme not pressurized and not placed in the gas cylinder.
  Control B: enzyme not pressurized but placed in gas cylinder 1. Control for gas 1 (Air).
  Control C: enzyme not pressurized but placed in gas cylinder 2. Control for gas 2 ($N_2$).
Solution Preparation: Apr. 10, 1991
  Soln A: Sodium phosphate buffer pH 6.6 at 25° C. 1 L Deionized water $141.96 \times 0.2 \times 187.5 \times 1/1000 = 5.3$ g $Na_2HPO_4$ $119.96 \times 0.2 \times 312.5 \times 1/1000 = 7.5$ g $NaH_2PO_4$ pH tested: 6.502

Soln B: Tyrosinase solution in Na Phos. buffer (228 U/ml)
  14.2 mg T-7755 diluted to 240 mL Na Phos. buffer pH 6.6 at 25° C.
  Soln C: 50 μg/ml L-Tyrosine solution in Na Phos. buffer
  10 mg T-3754 diluted to 200 ml Na Phos. buffer pH 6.6 at 25° C.
  Soln D: Sodium phosphate buffer pH 6.8 at 25° C.: 2 L Deionized water $2 \times 141.96 \times 0.2 \times 245 \times 1/1000 = 13.91$ g $Na_2HPO_4$ $2 \times 119.96 \times 0.2 \times 255 \times 1/1000 = 12.20$ g $NaH_2PO_4$ pH tested: 6.719
  Soln E: 100 μg/mL β-D-Glucopyranoside solution in Na Phos. buffer
  25 mg N-7006 diluted to 250 ml Na Phos. buffer pH 6.8 at 25° C.
  Soln F: β-D-Glucosidase solution in Na Phos. buffer pH 6.8 (25° C.) (2.18 Units/ml)
  24 mg G-4511 diluted to 242 mL Na Phos. buffer pH 6.8 at 25° C.
Method
  Tyrosinase: Apr. 11, 1991
  Place a 100 ml aliquot of enzyme solution into each of 2 disposable gas cylinders. Shake the enzyme in each cylinder for several minutes and then remove a 5 ml sample for Control B and Control C.
  Remove cylinders to the dock, gassing with the appropriate gas; bring pressure slowly up to 30.6 atm. Let sit at the required pressure for 60 minutes. Slowly depressurize to 2 psi before bringing into the lab.
  Transfer approximately 10 ml of the enzyme from each cylinder while keeping it under gas into separate beakers and run a TDrive/CPRG on the enzyme/substrate mixture immediately.

Enzyme 1, Gas 1, Pressure 1, Repetition 1

Enzyme 1, Gas 2, Pressure 1, Repetition 1

Bring the cylinders back to the dock and repressurize to 100 atm with the appropriate gas. Let sit at the required pressure for 60 minutes. Slowly depressurize to 2 psi before bringing into the lab.
  Transfer approximately 10 ml of the enzyme from each cylinder while keeping it under gas into separate beakers and run a TDrive/CPRG on the enzyme/substrate mixture immediately.

Enzyme 1, Gas 1, Pressure 2, Repetition 1

Enzyme 1, Gas 2, Pressure 2, Repetition 1

β-Glucosidase
  Rinse the cylinders with copious quantities of D.I. $H_2O$. Then rinse the cylinders with the second enzyme solution (glucosidase). Place a 25 ml aliquot of enzyme solution into each of 2 disposable gas cylinders. Shake the enzyme in each cylinder for several minutes and then remove a 5 ml sample for Control B and Control C.
  Remove cylinders to the dock, gassing with the appropriate gas; bring pressure slowly up to 30.6 atm. Let sit at the required pressure for 60 minutes. Slowly depressurize to 2 psi before bringing into the lab.
  Transfer approximately 10 ml of the enzyme from each cylinder while keeping it under gas into separate beakers and run a TDrive/CPRG on the enzyme/substrate mixture immediately.

Enzyme 2, Gas 1, Pressure 1, Repetition 1

Enzyme 2, Gas 2, Pressure 1, Repetition 1

Bring the cylinders back to the dock and repressurize to 100 atm with the appropriate gas.

Let sit at the required pressure for 60 minutes. Slowly depressurize to 2 psi before bringing into the lab.

Transfer approximately 10 ml of the enzyme from each cylinder while keeping it under gas into separate beakers and run a TDrive/CPRG on the enzyme/substrate mixture immediately.

Enzyme 2, Gas 1, Pressure 2, Repetition 1

Enzyme 2, Gas 2, Pressure 2, Repetition 1

Spectro Study: 25° C.
Cuvettes: 34 minimum
PARAM:
  slit 1
  speed 1500
  Asave Y
  Aprint N
CPRG:
  Tyrosinase:
    305 nm
    80 Pts→20 min RUN
    16 s int
    $y_{min}=0.0$
    $y_{max}=2.0$
  β-Glucosidase:
    400 nm
    40 Pts→10 min RUN
    16 s int
    $y_{min}=0.0$
    $y_{max}=1.5$
Blanks:
  Tyrosinase: 2 mL Soln A+0.5 mL Soln B
  β-Glucosidase: 2 ml Soln E+0.5 mL Soln D
Sample:
  Tyrosinase 2 ml Soln C+0.5 ml Soln B
  β-Glucosidase: 2 ml Soln E+0.5 ml Soln F
Cell Transporter:
  Cell 1: Control A
  Cell 2: Control B
  Cell 3: Control C
  Cell 4: Gas 1 (air)
  Cell 5: Gas 2 ($N_2$)
Files:
  Tyrosinase:
    X1P1G1C1 ... 5.SP→X1P1G1C1 ... 5. SP were renamed X1P1E1C1 ... 5.SP thru DOS.
    X1P2E1C1 ... 5.SP→... 5.SP began with a higher abs so we tapped out the gas bubbles and did a full range scan of all 5 cells:
      Full Range Scan 900–190 nm:
      Files: X1SCAN1 ... 5.SP
  10 FILES:
  β-Glucosidase:
    X2P1E2C1 ... 5.SP
    X2P2E2C1 ... 5.SP
  10 FILES:
Trial 2: Apr. 15, 1991
In this trial we will only do pressure tests of Tyrosinase.
Gasses
  1. Air
  2. $N_2$
Pressures
  1. 30.6 atm (450 psi)
  2. 100.0 atm (1470 psi)
Controls
  Control A: enzyme not pressurized and not placed in the gas cylinder.
  Control B: enzyme not pressurized but placed in gas cylinder 1. Control for gas 1 (Air).
  Control C: enzyme not pressurized but placed in gas cylinder 2. Control for gas 2 ($N_2$).
Solution preparation: Apr. 10, 1991
  Soln A: Sodium phosphate buffer pH 6.6 at 25° C. 1 L Deionized water $$141.96 \times 0.2 \times 187.5 \times 1/1000 = 5.3 \text{ g } Na_2HPO_4$$

$$119.96 \times 0.2 \times 312.5 \times 1/1000 = 7.5 \text{ g } NaH_2PO_4$$

pH tested: 6.502

Soln B: Tyrosinase solution in Na Phos. buffer (228 u/ml)
  14.2 mg T-7755 diluted to 240 mL Na Phos. buffer pH 6.6 at 25° C.

Soln C: 50 µg/mL L-Tyrosine solution in Na Phos. buffer
  10 mg T-3754 diluted to 200 ml Na Phos. buffer pH 6.6 at 25° C.

Method
  Tyrosinase:
  Place a 25 ml aliquot of enzyme solution into each of 2 disposable gas cylinders. Shake the enzyme in each cylinder for several minutes and then remove a 5 ml sample for Control B and Control C. Remove cylinders to the dock, gassing with the appropriate gas. Remove headspace/residual gas by pressurizing and depressurizing the gas cylinder several times. Bring pressure slowly up to 30.6 atm. Let sit at the required pressure for 60 minutes. Slowly depressurize to 40 psi before bringing into the lab.

Transfer approximately 5 ml of the enzyme from each cylinder while keeping it under gas into separate beakers and run a TDrive/CPRG on the enzyme/substrate mixture immediately. Enzyme 1, Gas 1, Pressure 1, Repetition 2 Enzyme 1, Gas 2, Pressure 1, Repetition 2 Enzyme 1, Gas 2, Pressure 2, Repetition 2

Spectro Study: 25° C.
Cuvettes: 10 minimum
PARAM:
  slit 1
  speed 1500
  Asave Y
  Aprint N
CPRG
  Tyrosinase:
    305 nm
    80 Pts→20 min RUN
    16 s int
    $y_{min}=0.0$
    $y_{max}=2.0$
Blanks:
  Tyrosinase: 2 mL Soln A+0.5 mL Soln B
Sample:
  Tyrosinase: 2 ml Soln C+0.5 ml Soln B
Trial to see if Soln C is still usable:
  TDrive: 305 nm, 80 pts, 16 s int.
  S=2.0 ml C+0.5 ml B
  R=2.0 ml A+0.5 ml D Files: TYTRL1.SP
Cell Transporter:
  Run 1: 100 atm
    Cell 1: Control A
    Cell 2: Control B
    Cell 3: Control C
    Cell 4: Gas 1 (air)
    Cell 5: Gas 2 ($N_2$)
  Run 2: 30 atm
    Cell 1: Control A
    Cell 2: Control B
    Cell 3: Control C
    Cell 4: Gas 1 (air)
    Cell 5: Gas 2 ($N_2$)
Files:
  Tyrosinase:
    X7P2E1C1 ... 5.SP
    X7P1E1C1 ... 5.SP
10 FILES:

Trial 3: Apr. 24, 1991 (Soln prep and initial pressurization), Apr. 25, 1991, Apr. 26, 1991

In this trial we will only do pressure tests of Tyrosinase.
Gases:
  1. Air
  2. $N_2$
  3. Xe: 1 atm/$N_2$ to pressure
Pressures:
  1. 30.6 atm (450 psi)
  2. 100.0 atm (1470 psi)
Controls:
  Control A: enzyme not pressurized and not placed in the gas cylinder.
Solution Preparation: Apr. 24, 1991
  Soln A: Sodium phosphate buffer pH 6.8 at 25° C.
  2 L Deionized water 2×141.96×0.2×245×1/1000=13.91 g $Na_2HPO_4$ 2×119.96×0.2×255×1/1000=12.20 g $NaH_2PO_4$ pH tested: 6.740
Soln B: Tyrosinase solution in Na Phos. buffer (228 U/ml)
  14.2 mg T-7755 diluted to 240 mL Na Phos. buffer pH 6.8 at 25° C.
Soln C: 50 µg/mL L-Tyrosine solution in Na Phos. buffer
  10 mg T-3754 diluted to 200 ml Na Phos. buffer pH 6.8 at 25° C.
Method
  Tyrosinase
Apr. 24, 1991 Cylinder preparation: The cylinders (3) were put under vacuum then injected with 50 cc of D.I. $H_2O$ and put under pressure: Cylinder 1 with air Cylinder 2 with $N_2$ Cylinder 3 with $N_2$ to 60 psi, shaken, turned upside down and the pressure released to blow the liquid out of the cylinders. This process was repeated with 50 cc of sodium phosphate buffer. The cylinders were pressurized as described above 3 times to remove all the liquid from the cylinders.

Enzyme injection: The cylinders were again placed under vacuum and injected with 60 cc of Tyrosinase solution using the vacuum to suck the enzyme into the cylinder. The cylinders were pressurized as described above. The cylinder pressure was released and the cylinders repressurized 10 times to remove $O_2$ from the cylinders.

Final Pressurization: Cylinders 1 (air) and 2 ($N_2$) were pressurized with the corresponding gas to 30.6 atm. Cylinder 3 was pressurized to 1 atm with Xe then pressurized to 30.6 atm with $N_2$ to conserve Xe.

Time Tables: Cylinders were pressurized to 30 atm by 1:00pm on Apr. 24, 1991. Due to the fact that on Apr. 25, 1991 the spectrophotometers were being used at 5° C. for a different experiment the decision was made to sample the cylinders at the end of the day when the spectrophotometer was available to be put at 25° C. Sampling took place 28 hours after pressurization. A spectro/gas run was immediately preformed on these samples.

Apr. 25, 1991. Repressurization: Cylinders were repressurized at 6:00pm on Apr. 25, 1991 to 100 atm. These cylinders will be sampled at 2:00pm Apr. 26, 1991 (20 hrs after pressurization).

Spectro Study: Apr. 25, 1991 25° C.
Cuvettes: 10 minimum
PARAM:
  slit 1
  speed 1500
  Asave Y
  Aprint N
CPRG:
  Tyrosinase:
    305 nm
    80 Pts→20 min RUN
    16 s int
    $y_{min}$=0.0
    $y_{max}$=2.0
Blanks:
  Tyrosinase: 2 mL Soln A+0.5 mL Soln B
Sample:
  Tyrosinase: 2 ml Soln C+0.5 ml Soln B
Cell Transporter:
  Run 1: 30 atm
    Cell 1: Control A
    Cell 2: Gas 1 (air)
    Cell 3: Gas 2 ($N_2$)
    Cell 4: Gas 3 (Xe:1 atm/$N_2$:29 atm)
Files:
  Tyrosinase:
    Y30G1 ... 4.SP
4 FILES:
Spectro Study: Apr. 26, 1991 25° C.
Cuvettes: 10 minimum
PARAM:
  slit 1
  speed 1500
  Asave Y
  Aprint N
CPRG:
  Tyrosinase:
    5 nm
    80 Pts→20 min RUN
    16 s int
    $y_{min}$=0.0
    $y_{max}$=2.0
Blanks:
  Tyrosinase: 2 mL Soln A+0.5 mL Soln B
Sample:
  Tyrosinase: 2 ml Soln C+0.5 ml Soln B
Cell Transporter:

Run 1: 100 atm
 Cell 1: Control A
 Cell 2: Gas 1 (air)
 Cell 3: Gas 2 ($N_2$)
 Cell 4: Gas 3 (Xe:1 atm/$N_2$:29 atm)
Files:
 Tyrosinase:
  Y100G1 . . . 4.SP
4 FILES:
Protocol
Effects of Pressure on Enzymes.
Enzyme
 Tyrosinase (SIGMA No. T-7755) (Monophenol monooxygenase; Polyphenol oxidase;
  Catechol oxidase; Monophenol, dihydroxyphenylalanine: oxygen oxidoreductase;
  EC 1.14.18.1)
 From Mushroom
Tyrosinase Unit Definition
 One unit will cause an increase in $A_{280}$ of 0.001 per min at pH 6.5 at 25° C. in 3 mL reaction mix containing L-tyrosine.
 Tyrosinase activity: 3870 U/mg solid
 7.1 mg solid→27,440 Units
 Stored desiccated below 0° C.
Substrate
 L-Tyrosine (SIGMA No. T-3754)
 L-3-[4-Hydroxyphenyl]alanine
 Free Base (pfs) Crystalline
 Anhydrous Mol. Wt. 181.2
 Stored at room temperature (25° C.)
Enzyme
 β-D-Glucosidase (SIGMA No. G-4511)
 (Emulsin; β-D-Glucoside glucohydrolase EC 3.2.1.21)
 From Almonds
Unit Definition
 One unit will liberate 1.0 μmole of glucose from salicin per min at pH 5.0 at 37° C.
 Activity: 22 U/mg solid
 12 mg solid→264 Units
 Stored desiccated at 0°–5° C.
Substrate
 p-Nitrophenyl-β-D-Glucopyranoside (SIGMA No. N-7006)
 Crystalline
 Contains 2.4% solvent
 Anhydrous Mol. Wt. 301.3
 Stored desiccated below 0° C.
Trial 1
Gases
 1. Air
 2. $N_2$
 3. Ar
 4. $O_2$
Pressures
 1. 2 atm (30 psi)
Solution Preparation Apr. 29, 1991
prep: Apr. 26, 1991
 Soln A: Sodium phosphate buffer pH 6.8 at 25° C.
 2 L Deionized water 2×141.96×0.2×245×1/1000=13.91 g $Na_2HPO_4$ 2×119.96×0.2×255×1/1000=12.20 g $NaH_2PO_4$ pH tested:
 Soln B: Tyrosinase solution in Na Phos. buffer (228 U/ml)
 14.2 mg T-7755 diluted to 240 mL Na Phos. buffer pH 6.8 at 25° C.
 Soln C: 50 μg/mL L-Tyrosine solution in Na Phos. buffer
 10 mg T-3754 diluted to 200 ml Na Phos. buffer pH 6.8 at 25° C.
 Soln E: 100 μg/mL β-D-Glucopyranoside solution in Na Phos. buffer
 25 mg N-7006 diluted to 250 ml Na Phos. buffer pH 6.8 at 25° C.
 Soln F: β-D-Glucosidase solution in Na Phos. buffer pH 6.8 (25° C.) (2.18 Units/ml)
 24 mg G-4511 diluted to 242 mL Na Phos. buffer pH 6.8 at 25° C.
Method
 The cell transporters were removed from the spectrophotometers and the fixed cells were installed.
 Acrylic cuvettes were prepared by first installing a blue silicone plug, needles and then siliconing the tops and sides of the cuvettes with general all purpose silicone. These were left to cure for 48 hours before use. When the silicone was cured the cuvettes were tapped vertically and then around the plug with strapping tape.
 Sample prep: Apr. 29, 1991 Cuvettes were filled for the 2 atm experiments for both enzymes. Each cuvette was gassed 10×10 cc with the appropriate gas and refrigerated for 15 minutes prior to running.
 Serum vials were filled with 5 cc of the corresponding enzyme and gassed with 10×10 cc of the appropriate gas prior to running.
 The spectrophotometers were set up such that a continuous flow of each gas could be delivered to each spectro at all times. A 100 $psi_{max}$ gauge was installed to read the cuvette pressure and 2 on/off valves were installed so that the reference cell could be pressurized during the second replicate. A ball valve was installed between the cylinder/house line and the gauge so that gas flow could be controlled directly at the spectrophotometers. A check valve was placed in each line to ensure that a back pressure would not cause contamination of the house lines or the gas cylinders. The cuvettes retained the 2 needles during the entire run. One of the needles was attached to the gas line while the second was used for enzyme introduction and then plugged. Due to the bulky nature of the assembly it was impossible to use the installed doors of the spectrophotometers therefore they were removed. A 4-layer thick black felt cover was prepared for each spectro to minimize the amount of light entering the system.
 While the cuvette was equilibrating to temperature in the spectrophotometer both needles remained in the cuvette with 10 cc syringes still attached. Prior to enzyme introduction one of the syringes was removed while the gas line was attached to the needle. A small flow of gas run through the line while this was done to ensure that there was no oxygen contamination. The needles remained above the liquid level. The second syringe was removed to allow constant flow through the cuvette. The enzyme was injected through the second needle using a 1 cc syringe. The needle was then plugged, the cuvette pressurized and the run begun.
Apr. 29, 1991
 2 atm
 reference not pressurized Tyrosinase:
1. Air nonpressurized reference or sample.
2. replicate 1 (reference cell not pressurized) 4 gases Glucosidase:
1. Air nonpressurized reference or sample.
2. replicate 1 (reference cell not pressurized) 4 gases Spectro Study: room temp
Cuvettes: 10
PARAM:
  slit 1
  speed 1500
  Asave Y
  Aprint N
TDrive:
  Tyrosinase: New spectrophotometer (B)
  305 nm
  60 Pts→15 min RUN
  16 s int
  $y_{min}=0.0$
  $y_{max}=1.6$
  β-Glucosidase: old spectrophotometer (A)
  400 nm
  60 Pts→15 min RUN
  16 s int
  $y_{min}=0.0$
  $y_{max}=2.0$
Blanks:
  Tyrosinase: 2 mL Soln A+0.5 mL Soln B
  β-Glucosidase: 2 ml Soln E+0.5 mL Soln A
Sample:
  Tyrosinase: 2 ml Soln C+0.5 ml Soln B
  β-Glucosidase: 2 ml Soln E+0.5 ml Soln F
Files:
  Apr. 29, 1991
  Tyrosinase:
    Air reference (nonpressurized): 429TYTRL.SP
    2 atm (unpressurized reference):
    Y4E1P1G1 ... 7.SP
  Glucosidase:
    Air reference (nonpressurized): 429GLUTR.SP
    2 atm (unpressurized reference):
    Y4E1P1G1 ... 7.SP
Note The temperature inside the fixed sample cell did not remain constant which directly effects the results we obtain. We will remove the fixed cell holders on both spectrophotometers and replace them with the cell transporters.

Trial 2: Apr. 30, 1991
Gases:
1. Air
2. $N_2$
3. Ar
4. $O_2$
Pressures:
1. 2 atm (30 psi)
Sample Preparation The solutions prepared on Apr. 29, 1991 will be reused.
Method The spectrophotometers were assembled for continuous gas flow as described in Trial 1. Fixed cell holders were replaced with the cell transporters so that a constant temperature could be maintained using the Fisher Circulators and Digital Controllers. We continued to use the black felt covers as they seem to provide suitable light protection.

A nonpressurized gas run using all four gases was done for each enzyme. Each cuvette was gassed with 10×10 cc of the corresponding gas and refrigerated for 15 minutes. The 2 needles used for gassing the cuvettes were removed when the cuvettes were placed into the spectrophotometer. Enzyme was introduced into the cuvettes using a 1 cc syringe with a 20G11/2 needle attached. The needle was placed into the cuvette through the silicone plug but not immersed into the liquid. This was to ensure that enzyme introduction into the cuvette was the same as for the pressurized gas run.

Serum vials were filled with 5 cc of the corresponding enzyme and gassed with 10×10 cc of the appropriate gas prior to running.
Cuvettes Tyrosinase: The cuvettes with blue silicone, general all purpose silicone and strapping tape were used for this enzyme.

Glucosidase: The cuvettes with blue silicone only were used for this enzyme.

All cuvettes were pressure tested to 32 psi before use.
Spectro Study:
Cuvettes: 26
PARAM:
  slit 1
  speed 1500
  Asave Y
  Aprint N
TDrive:
  Tyrosinase: New spectrophotometer (B) 25° C.
  305 nm
  60 Pts→15 min RUN
  16 s int
  $Y_{min}=0.0$
  $Y_{max}=1.6$
  β-Glucosidase: Old spectrophotometer (A) 35° C.
  400 nm
  60 Pts→15 min RUN
  16 s int
  $y_{min}=0.0$
  $y_{max}=2.0$
Blanks:
  Tyrosinase: 2 mL Soln A+0.5 mL Soln B
  β-Glucosidase: 2 ml Soln E+0.5 mL Soln A
Sample:
  Tyrosinase: 2 ml Soln C+0.5 ml Soln B
  β-Glucosidase: 2 ml Soln E+0.5 ml Soln F
Files:
  Apr. 30, 1991
  Tyrosinase:
    Gas run (nonpressurized): Y6E1RSG1 ... 4.SP
    2 atm (reference nonpressurized):
    Y6E1P1G1 ... 4.SP
    2 atm (reference pressurized):
    Y7E1P1G1 ... 4.SP
  Glucosidase:
    Gas run (nonpressurized): Y6E2RSG1 ... 4.SP
    2 atm (reference nonpressurized):
    Y6E2P1G1 ... 4.SP
    2 atm (reference pressurized): Y7E2P1G1 ... 4.SP
Note We have decided to use the cuvettes with the blue silicone plug for future pressure testing. The additional general all purpose silicone and strapping tape seems to diminish the integrity of the gas tight seal that the blue silicone has with the cuvette.

Trial 3: May 1, 1991

Gases:
 1. Air
 2. $N_2$
 3. Ar
 4. $O_2$

Pressures:
 1. 3 atm (45 psi)

Sample Preparation

The solutions prepared on Apr. 29, 1991 will be reused.

Method

The same method as used in Trial 2 on Apr. 30, 1991 was used for this trial.

Spectro Study:
 Cuvettes: 31
 PARAM:
  slit 1
  speed 1500
  Asave Y
  Aprint N
 TDrive: Tyrosinase: New spectrophotometer (B) 25° C.
  305 nm
  60 Pts→15 min RUN
  16 s int
  $Y_{min}=0.0$
  $Y_{max}=1.6$
 β-Glucosidase: Old spectrophotometer (A) 35° C.
  400 nm
  60 Pts→15 min RUN
  16 s int
  $y_{min}=0.0$
  $y_{max}=2.0$ Blanks:
 Tyrosinase: 2 mL Soln A+0.5 mL Soln B
 62 -Glucosidase: 2 ml Soln E+0.5 mL Soln A Sample:
 Tyrosinase: 2 ml Soln C+0.5 ml Soln B
 β-Glucosidase: 2 ml Soln E+0.5 ml Soln F Files:
 May 5, 1991
  Tyrosinase:
   Gas run (nonpressurized): Y6E1SRG1 . . . 4.SP
   Gas run (nonpressurized): Y7E1SRG1 . . . 4.SP
   3 atm (reference nonpressurized): Y6E1P2G1 . . . 4.SP
   3 atm (reference pressurized): Y7E1P2G1 . . . 4.SP
  Glucosidase:
   Gas run (nonpressurized): Y6E2SRG1 . . . 4.SP
   3 atm (reference nonpressurized): Y6E2P2G1 . . . 4.SP
    (NEW BLANK USED)
   3 atm (reference pressurized): Y7E2P2G1 . . . 4.SP Trial 4: May 3, 1991

Gases:
 5. Air
 6. Ne
 7. Kr
 8. Xe

Pressures: 1.2 atm (30 psi)

Solution Preparation: May 2, 1991 prep: Apr. 26, 1991 Soln A: Sodium phosphate buffer pH 6.8 at 25° C.

2 L Deionized water

2×141.96×0.2×245×1/1000=13.91 g $Na_2HPO_4$

2×119.96×0.2×255×1/1000=12.20 g $NaH_2PO_4$ pH tested:

Soln B: Tyrosinase solution in Na Phos. buffer (228 U/ml)

7.1 mg T-7755 diluted to 120 mL Na Phos. buffer pH 6.8 at 25° C.

Soln C: 50 pg/mL L-Tyrosine solution in Na Phos. buffer 10 mg T-3754 diluted to 200 ml Na Phos. buffer pH 6.8 at 25° C.

Soln E: 100 μg/mL β-D-Glucopyranoside solution in Na Phos. buffer 2.5 mg N-7006 diluted to 125 ml Na Phos. buffer pH 6.8 at 25° C.

Soln F: β-D-Glucosidase solution in Na Phos. buffer pH 6.8 (25° C.) (2.18 Units/ml)

12 mg G-4511 diluted to 121 mL Na Phos. buffer pH 6.8 at 25° C.

Method

The same method as used in Trial 2 and Trial 3 was used for this trial with 2 exceptions. The needles were immersed into the liquid in the cuvette after the enzyme was injected into the cuvette and a quantity of general all purpose silicone was placed around the needles to prevent gas from leaking out of the cuvette.

Spectro Study:
 Cuvettes: 20
 PARAM:
  slit 1
  speed 1500
  Asave Y
  Aprint N
 TDrive:
  Tyrosinase: New spectrophotometer (B) 25° C.
  305 nm
  40 Pts→10 min RUN
  16 s int
  $Y_{min}=0.0$
  $Y_{max}=1.6$
 β-Glucosidase: Old spectrophotometer (A) 35° C.
  400 nm
  40 Pts→10 min RUN
  16 s int
  $y_{min}=0.0$
  $y_{max}=2.0$ Blanks:
 Tyrosinase: 2 mL Soln A+0.5 mL Soln B
 β-Glucosidase: 2 ml Soln E+0.5 mL Soln A Sample:
 Tyrosinase: 2 ml Soln C+0.5 ml Soln B
 β-Glucosidase: 2 ml Soln E+0.5 ml Soln F Files:
 May 1, 1991

TDrive to check that the submerged needles do not pose a problem with absorbance.

TDrive: 40 pts, 16 s int., 305 nm: TYRONEE1.SP
TDrive: 40 pts, 16 s int., 400 nm: GLUCNEE1.SP
 Tyrosinase:
  Gas run (nonpressurized): Y6E1SRG5 . . . 8.SP
  2 atm (reference nonpressurized): Y6E1P1G5 . . . 8.SP
 Glucosidase:
  Gas run (nonpressurized): Y6E2SRG5 . . . 8.SP
  2 atm (reference nonpressurized): Y6E2P1G5 . . . 8.SP Note If the needles entered the light path they were removed to above the liquid level. This was done by turning off the room lights and while keeping the felt cover in place working in the spectrophotometer.

Results

Results are given as % inhibition of gases relative to 1 atmosphere of air/inhibition relative to 1 atmosphere after pressurization.

For tyrosinase:

|  | 2 atm | 3 atm | 30.6 atm | | 100 atm | |
|---|---|---|---|---|---|---|
|  |  |  | (24 hr) | (1 hr) | (~24 hr) | (1 hr) |
| Air | −7.0 & −15.4 | −11.6 | −37.0 | −4.9 | −65.8 | −11.1 |
| Xe | −76.0/−86.2 |  | −87.0 |  | −85.7 |  |
| Kr | −84.5/−93.1 |  |  |  |  |  |
| Ar | −76.9/−90.4 | −55.8/−72.1 |  |  |  |  |
| Ne | −69.0/−84.5 |  |  |  |  |  |
| $N_2$ | −71.2/−88.5 | −72.1/−82.6 | −78.8 | −15.4 | −84.7 | −20.0 |

The change in relative effect is very great. For example, for Xenon it is 75%. This clearly evidences that pressure alone significantly inhibits tyrosinase.

For betaglucosidase

At 3 atmospheres pressure, the degree of enhancement observed was changed as follows:

| Air | 0 (enhancement) > −12.5 (inhibition) |
|---|---|
| Xe | +3.1 > 0 −15.7 |
| Kr | +2.0 > 0 −6.2 |
| Ar | +1.0 > −13.2 |
| Ne | +1.0 > −12.5 |
| $N_2$ | 0 > −5.0 |

The above clearly indicates that reported inhibitions of hydrolases and other enzymes in prior art by noble gases are due to hydrostatic effects.

Oxygen addition experiment

Adding oxygen to tyrosinase lessened the effect of nitrogen completely. Adding oxygen lessened the effects of noble gases less well, clearly because the noble gases are affecting the enzyme through molecular properties above and beyond simple competitive displacement of oxygen from solution. This evidence distinguishes noble gas effects from those of nitrogen. Also, addition of a small amount oxygen enhanced tyrosinase activity slightly (as expected for an oxygen-requiring reaction), but further addition of oxygen had no additional effect. Thus, reports of strict linear relationships between oxygen tension and enzyme activity are flawed, as they can describe only conditions of oxygen limitation.

Addition of oxygen to air gave a maximum of 6% increase in activity of tyrosinase.

Addition of oxygen up to a saturating amount to a xenon-saturated solution changed the effect of xenon from inhibition to 50% inhibition.

Addition of oxygen as above-to an argon-saturated solution changed the effect of argon from an 82% to a 12% inhibition.

Addition of oxygen as above to a nitrogen-saturated solution completely eliminated the effect of nitrogen from an 84% inhibition, yielding zero inhibition.

There was no observed effect in adding oxygen to glucosidase reactions as would be expected for an oxygen-independent reaction. The addition of oxygen had no effect upon the action of any of the noble gases upon the enzyme, showing again that the effect of the noble gases upon the enzyme is dependent upon their molecular properties.

Gas Mixture Experiment

In addition to mixes of noble gases with nitrogen and oxygen, and of mixes of Kr and Xe, serial mixes of Ar and either Xe or Kr were tested.

Results for tyrosinase expressed as inhibition vs. air control:

| Mix = % Xe in AR | % inhibited | = % Kr in Ar | % inhibited |
|---|---|---|---|
| 0 | −75 | 0 | −75 |
| 0.1 | −72 |  |  |
| 1.0 | −73 |  |  |
| 5.0 | −83 |  |  |
| 10.0 | −81 | 10.0 | −80 |
| 50.0 | −78 | 50.0 | −78 |
| 100.0 | −86 | 100.0 | −77 |

Similar results were obtained with betaglucosidase, wherein enhancements were observed for all mixes, and these were of the same magnitude as those for Xe, Kr or Ar depending upon the closeness of the mix to the pure gases.

Protocol: Gas Mixes

Theory: Enzyme activity will change with gas mix

Gas Mixes:
1. Ar/Xe
2. Ar/Kr
  1. 0.1%
  2. 1.0%
  3. 5.0%
  4. 10.0%
  5. 50.0%

Enzyme

Tyrosinase (SIGMA No. T-7755) (Monophenol monooxygenase; Polyphenol oxidase;

Catechol oxidase; Monophenol, dihydroxyphenylalanine: oxygen oxidoreductase;

EC 1.14.18.1)

From Mushroom

Tyrosinase Unit Definition

One unit will cause-an increase in $A_{280}$ of 0-001 per min at pH 6.5 at 25° C. in 3 mL reaction mix containing L-tyrosine.

Tyrosinase activity: 3870 U/mg solid 7.1 mg solid→27,440 Units

Stored dessicated below 0° C.

Lot#8OH$_{9615}$

Substrate

L-Tyrosine (SIGMA No. T-3754)

L-3-[4-Hydroxyphenyl]alanine

Free Base (pfs) Crystalline

Anhydrous Mol. Wt. 181.2

Stored at room temperature (25° C.)

Lot#59F-0478

Enzyme

β-D-Glucosidase (SIGMA No. G-4511)

(Emulsin; β-D-Glucoside glucohydrolase EC 3.2.1.21)

From Almonds

Unit Definition

One unit will liberate 1.0 μmole of glucose from salicin per min at pH 5.0 at 37° C.

Activity: 22 U/mg solid 12 mg solid→264 Units

Stored dessicated at 0°–5° C.

Lot#49F-4021

Substrate
p-Nitrophenyl-β-D-Glucopyranoside (SIGMA No. N-7006)
Crystalline
Contains 2.4% solvent
Anhydrous Mol. Wt. 301.3
Stored dessicated below 0° C.
Lot#129F-5057

Solution Preparation
prep: Apr. 15, 1991 Soln A
Sodium phosphate buffer pH 6.6 at 25° C.
1 L Deionized water $$141.96 \times 0.2 \times 187.5 \times 1/1000 = 5.3 \text{ g Na}_2\text{HPO}_4$$

$$119.96 \times 0.2 \times 312.5 \times 1/1000 = 7.5 \text{ g NaH}_2\text{PO}_4$$

prep: Apr. 17, 1991 Soln B
Tyrosinase solution in Na Phos. buffer (228 U/ml)
14.2 mg T-7755 diluted to 240 mL Na Phos. buffer pH 6.6 at 25° C.

prep: Apr. 17, 1991 Soln C
50 μg/ml L-Tyrosine solution in Na Phos. buffer
10 mg T-3754 diluted to 200 ml Na Phos. buffer pH 6.6 at 25° C.

prep: Apr. 10, 1991 Soln D
Sodium phosphate buffer pH 6.8 at 25° C.:
2 L Deionized water $$2 \times 141.96 \times 0.2 \times 245 \times 1/1000 = 13.91 \text{ g Na}_2\text{HPO}_4$$

$$2 \times 119.96 \times 0.2 \times 255 \times 1/1000 = 12.20 \text{ g NaH}_2\text{PO}_4$$

prep: Apr. 15, 1991 Soln E
100 μg/ml β-D-Glucopyranoside solution in Na Phos. buffer
25 mg N-7006 diluted to 250 ml Na Phos. buffer pH 6.8 at 25° C.

prep: Apr. 17, 1991 Soln F: β-D-Glucosidase solution in Na Phos. buffer pH 68 (25° C.) (2.18 Units/ml)
24 mg G-4511 diluted to 242 mL Na Phos. buffer pH 6.8 at 25° C.

Method
Apr. 17, 1991: Prep Solutions, purge cuvettes with air after making sure they are gas tight, fill cuvettes and refrigerate, prep enzyme serum vials and prep gas vials.

Apr. 18, 1991: Gas mix prep: 120 cc serum vials were used to mix the gassed in. These vials were purged using vacuum while 1 atm of argon was maintained in the vial. The vials were purged for 20 seconds in this manner. The vials were under slight pressure which was released through a needle. This is considered 120 cc of Argon. The necessary volumes of Argon and the gas to be mixed with (Xe or Kr) were then introduced into the vials using a 30 cc syringe and needle.

| %    | Argon  | Xe/Kr  |
|------|--------|--------|
| 0.1% | 120 cc | 0.2 cc |
| 1.0% | 118 cc | 2.4 cc |
| 5.0% | 108 cc | 12 cc  |
| 10%  | 96 cc  | 24 cc  |
| 50%  | 0 cc   | 120 cc |

Trial 1
We gassed the enzyme using 1 vial of gas mix using 8×10 cc of gas out of the vial. We gassed the cuvette/substrate using a second vial of gas mix using 8×10 cc of gas out of the vial. Argon and Xenon were retrieved from the gas cylinders.

We filled the enzyme sampling syringes as follows:

| enzyme     | gas |
|------------|-----|
| Ar         | Ar  |
| Xe         | Xe  |
| 0.1% Ar/Xe | Ar  |
| 1.0% Ar/Xe | Ar  |
| 5.0% Ar/Xe | Ar  |

Cell Transporter
Gas Mix: Ar/Xe, 1 repetition
Run 1:
 Cell 1: Ar
 Cell 2: Xe
 Cell 3: Ar/Xe 0.1%
 Cell 4: Ar/Xe 1.0%
 Cell 5: Ar/Xe 5.0%
 (Replicate 1: R1)
PARAM:
 slit 1
 speed 1500
 Asave Y
 Aprint N
CPRG:
 Tyrosinase: 25° C.
 405 nm
 80 Pts→20 min RUN
 16 s int
 $y_{min}=0.0$
 $y_{max}=2.0$
 β-Glucosidase: 35° C.
 400 nm
 60 Pts→15 min RUN
 16 s int
 $y_{min}=0.0$
 $y_{max}=1.5$
Blanks:
 Tyrosinase: 2 mL Soln A+0.5 mL Soln B
 β-Glucosidase: 2 ml Soln E+0.5 mL Soln D
Sample:
 Tyrosinase: 2 ml Soln C+0.5 ml Soln B
 β-Glucosidase: 2 ml Soln E+0.5 ml Soln F
Files:
 Tyrosinase:
  X9R1G1M1 . . . 5.SP
 Glucosidase:
  X0R1G1M1 . . . 5.SP Results of Trial 1
We found that we has air contamination in the Tyrosinase run and assumed that the same was true for the glucosidase run. We determined that we would be unable to retrieve 8×10 cc of gas mix from 1 vial. Therefore we determined that we would prepare 2 vials of gas mix per cuvette for gassing and 2 vials of gas mix per enzyme which would enable us to do 10×10 cc per cuvette/vial.

Trial 2
We gassed the second run using 2 vials of gas mix per cuvette and 2 vials of gas mix per enzyme. We then proceeded to do the last 2 gas mixes (10% and 50%).

Gas Mix: Ar/Xe, 1 repetition
Cell Transporter

Run 2:
    Cell 1: Ar
    Cell 2: Xe
    Cell 3: Ar/Xe 10.0%
    Cell 4: Ar/Xe 50.0%
    Cell 5: Air
    (Replicate 1: R1)
PARAM
    slit 1
    speed 1500
    Asave Y
    Aprint N
CPRG:
    Tyrosinase: 25° C.
    305 nm
    80 Pts→20 min RUN
    16 s int
    $y_{min}=0.0$
    $y_{max}=2.0$
    β-Glucosidase: 35° C.
    400 nm
    60 Pts→15 min RUN
    16 s int
    $y_{min}=0.0$
    $y_{max}=1.5$
Blanks:
    Tyrosinase: 2 mL Soln A+0.5 mL Soln B
    β-Glucosidase: 2 ml Soln E+0.5 mL Soln D
Sample:
    Tyrosinase: 2 ml Soln C+0.5 ml Soln B
    β-Glucosidase: 2 ml Soln E+0.5 ml Soln F
Files:
    Tyrosinase:
        X9R1G1M6 ... 0.SP
    Glucosidase:
        XOR1G1M6 ... 0.SP Results of Trial 2

Tyrosinase gave a separation such that we would expect therefore we will assume that our new method of gassing is appropriate and will continue to gas in this fashion. Glucosidase does not show a large separation therefore due to time constraints we will focus on Tyrosinase specifically the 10% and 50% gas mixtures.

Run 3:
    Cell 1: Ar
    Cell 2: Xe
    Cell 3: Ar/Xe 10.0%
    Cell 4: Ar/Xe 50.0%
    Cell 5: Air (Replicate 2: R2)
Files
    Tyrosinase:
        X9R2G1M6 ... 0.SP
    We prepared the Ar/Kr mixes as described above and did 2 replicates of the 10% and 50% mixes.
Run 4/5:
    Cell 1: Ar
    Cell 2: Kr
    Cell 3: Ar/Kr 10.0%
    Cell 4: Ar/Kr 50.0%
    Cell 5: Air
    (Replicate 1, 2: R1, R2)
Files
    Tyrosinase:
        X9R1G2M6 ... 0.SP
        X9R2G2M6 ... 0.SP Results Results with Ar/Xe look much better than the results we got with Ar/Kr. We will continue to do replicates of both mixes using 10% and 50%. Time permitting we will so replicates of 0.1%, 1% and 5% of both gas mixes with Tyrosinase only.

Apr. 19, 1991

Tyrosinase 2 replicates Ar/Xe on one spectrophotometer and Ar/Kr on the other spectro.

New Spectro:
Run 1:
    Cell 1: Ar
    Cell 2: Xe
    Cell 3: Ar/Xe 10.0%
    Cell 4: Ar/Xe 50.0%
    Cell 5: Air
    (Replicate 3: R3)
Run 2:
    Cell 1: Ar
    Cell 2: Xe
    Cell 3: Ar/Xe 10.0%
    Cell 4: Ar/Xe 50.0%
    Cell 5: Air
    (Replicate 4: R4)
Old Spectra:
Run 1:
    Cell 1: Ar
    Cell 2: Kr
    Cell 3: Ar/Kr 10.0%
    Cell 4: Ar/Kr 50.0%
    Cell 5: Air
    (Replicate 3: R3)
Run 2:
    Cell 1: Ar
    Cell 2: Kr
    Cell 3: Ar/Kr 10.0%
    Cell 4: Ar/Kr 50.0%
    Cell 5: Air
    (Replicate 4: R4)
PARAM:
    slit 1
    speed 1500
    Asave Y
    Aprint N
CPRG:
    Tyrosinase: 25° C.
    305 nm
    80 Pts→20 min RUN
    16 s int
    $y_{min}=0.0$
    $y_{max}=2.0$
Blanks:
    Tyrosinase: 2 mL Soln A+0.5 mL Soln B
Sample:
    Tyrosinase: 2 ml Soln C+0.5 ml Soln B
Files:
    Ar/Xe:
        X9R3G1M6 ... 0.Sp
        X9R4G1M6 ... 0.Sp
    10 FILES
    Ar/Kr:
        X9R3G2M6 ... 0.SP
        X9R4G2M6 ... 0.SP
    10 FILES
    Time permitting
        We were only able to run the following:

New Spectro:
Run 3:
  Cell 1: Ar
  Cell 2: Xe
  Cell 3: Ar/Xe 0.1%
  Cell 4: Ar/Xe 1.0%
  Cell 5: Ar/Xe 5.0%
  (Replicate 2: R2)
Run 4:
  Cell 1: Ar
  Cell 2: Xe
  Cell 3: Ar/Xe 0.1%
  Cell 4: Ar/Xe 1.0%
  Cell 5: Ar/Xe 5.0%
  (Replicate 3: R3)
Files
  Ar/Xe:
    X9R2G1M1 ... 5.SP
    X9R3G1M1 ... 5.SP
  10 FILES Thus, the present invention generally provides a method of regulating enzymatic activity by contacting one or more enzymes with a gas containing one or more noble gases or mixtures thereof.

In accordance with the present invention, the enzyme regulated may be a single, isolated enzyme or one or more enzymes which comprise a mixture. For example, in accordance with the present invention, a mixture of enzymes may be regulated by selectively inhibiting the activities of one or more enzymes and selectively enhancing the activities of one or more enzymes.

Furthermore, enzymatic activity may be regulated in accordance with the present invention over a temperature range of from the boiling point of liquid nitrogen (about −200° C.) to about 120° C.

In accordance with the present invention, any enzyme can be regulated using the present noble gases. However, by selecting the appropriate conditions of pH, temperature, pressure, [E] and [S], all enzymes can be inhibited specifically by all of the noble gases of the present invention. Furthermore, it is within the skill of the artisan to utilize the present disclosure and guidelines set forth hereinabove to determine the optimal levels of pH, temperature, pressure, [E] and [S] for any particular enzyme system or mixed enzyme system of interest.

The figures of the present specification will now be discussed in more detail.

FIG. 1 illustrates the absorption spectrum of 2.5 ml tyrosinase (100 µg/ml) vs. 2.5 ml sodium phosphase buffer at pH 6.85.

Figure 2:
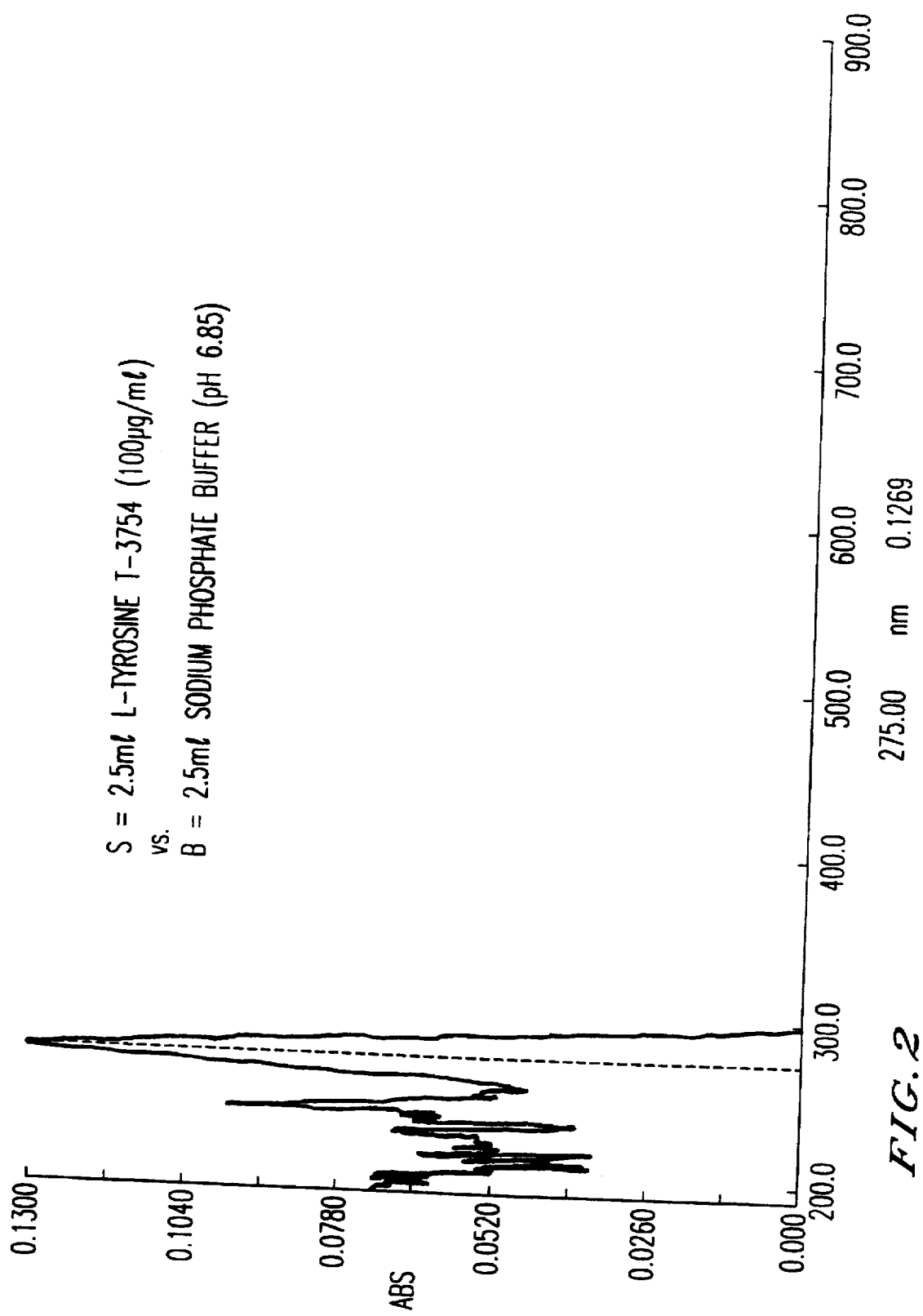
FIG. 2 illustrates the absorption spectrum of L-tyrosine.

FIG. 2 illustrates the absorption spectrum of 2.5 ml L-tyrosine (100 µg/ml) vs. 2.5 ml sodium phosphase buffer at pH 6.85.

Figure 3:
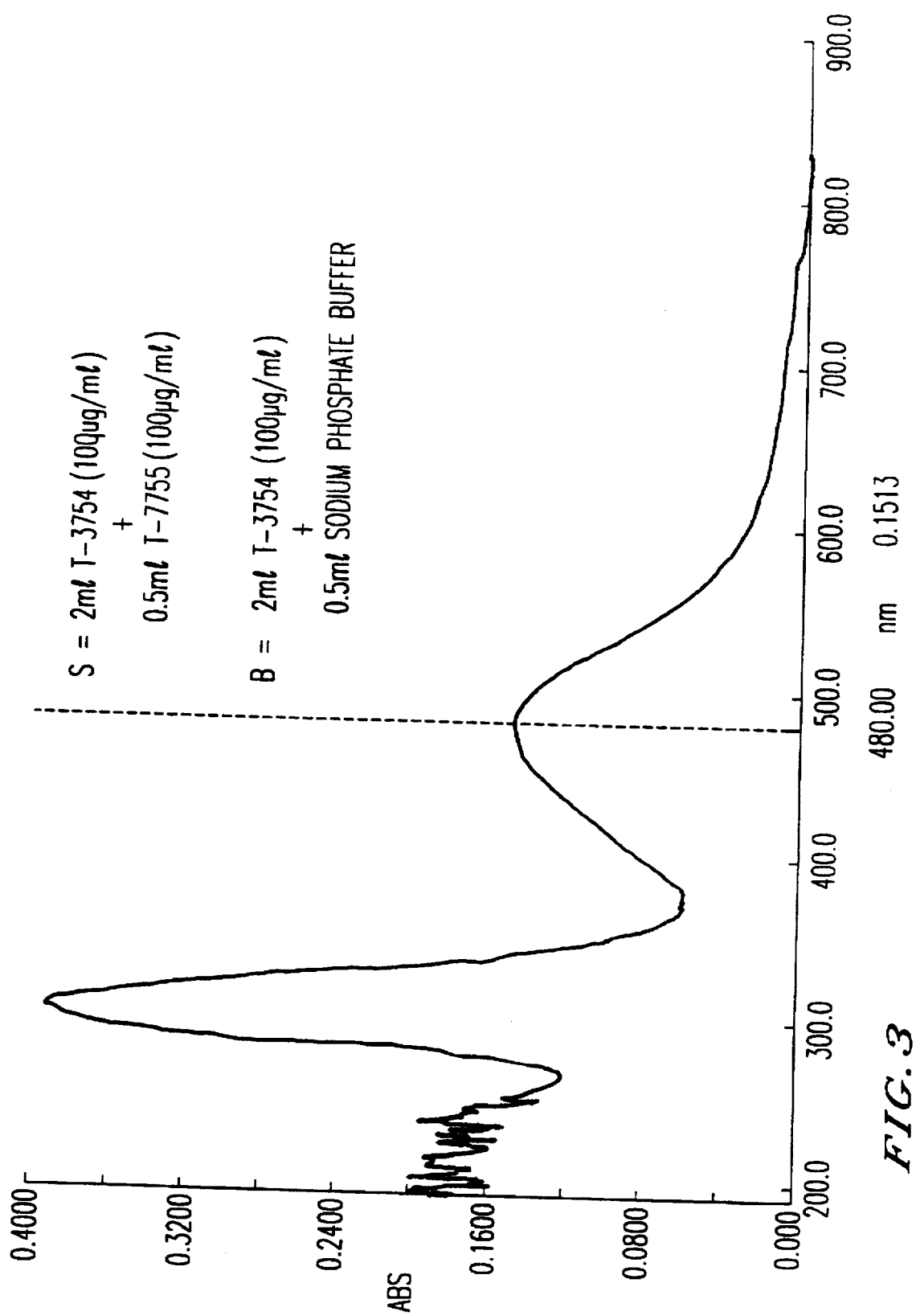
FIG. 3 illustrates the absorption spectrum of tyrosinase and L-tyrosine blanked with L-tyrosine.

FIG. 3 illustrates the absorption spectrum of tyrosinase and L-tyrosine blanked with L-tyrosine at the concentrations and pH indicated.

Figure 4:
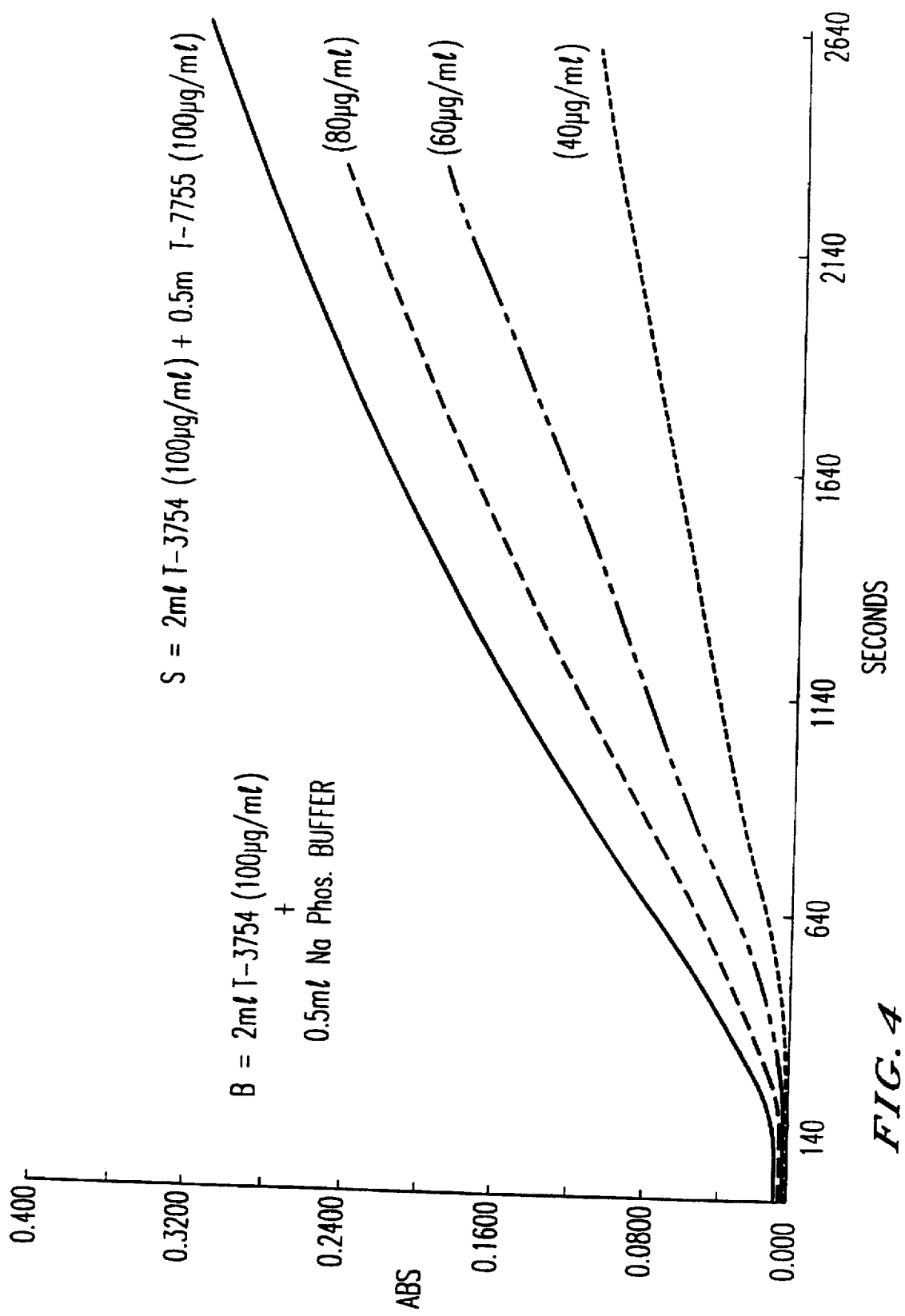
FIG. 4 illustrates an overlay of results of reactions run with varying concentrations of tyrosinase, showing direct linear first-order tyrosinase concentration dependence.

FIG. 4 illustrates an overlay of results of reactions run with varying concentrations of tyrosinase (40, 60, 80 and 100 µg/ml), showing direct linear first-order tyrosinase concentration dependence.

Figure 5:
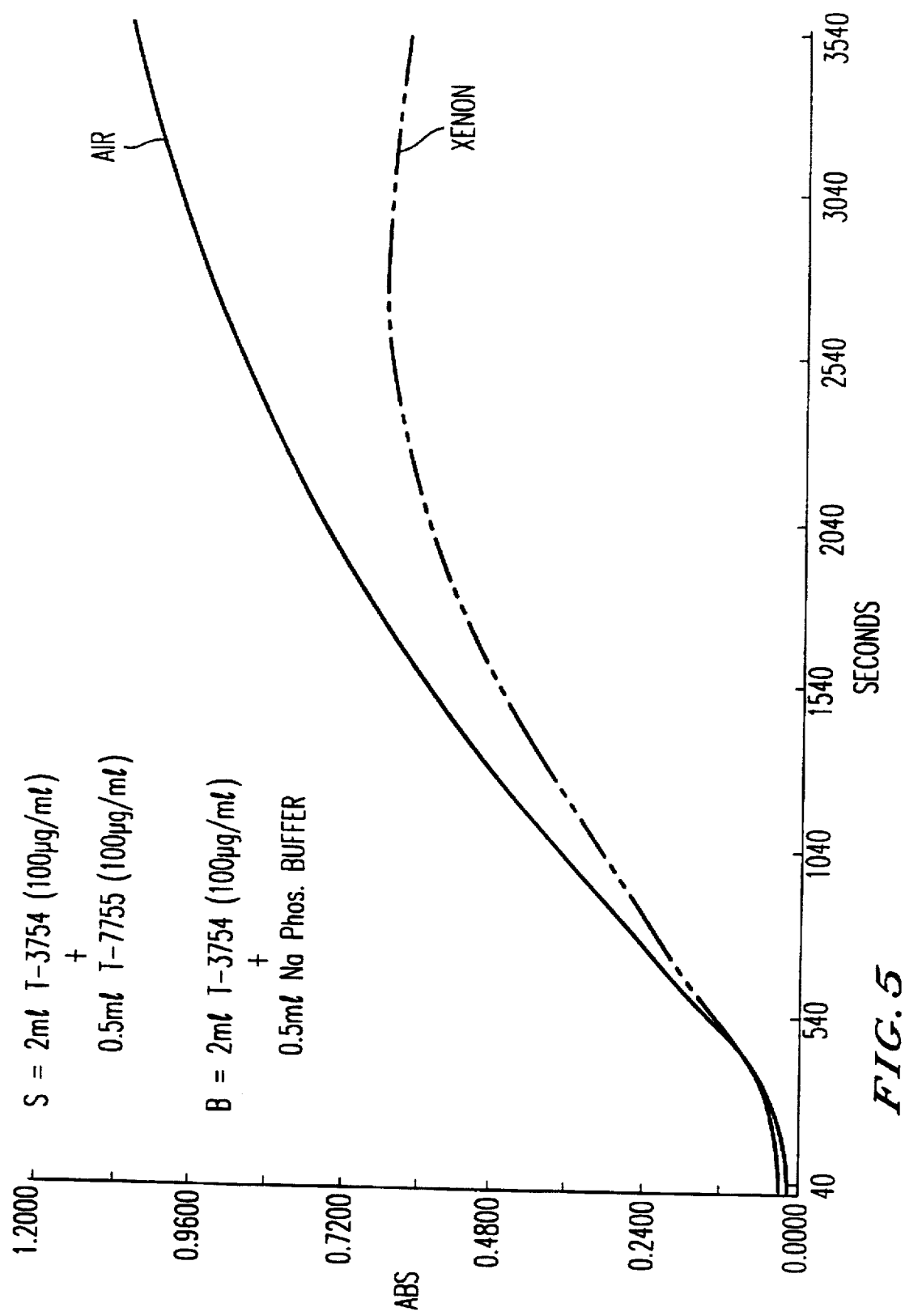
FIG. 5 demonstrates the inhibition of tyrosinase by xenon at equal w/w.

FIG. 5 illustrates the inhibition of tyrosinase by xenon at equal (w/w), using the concentrations and pH indicated.

Figure 6:
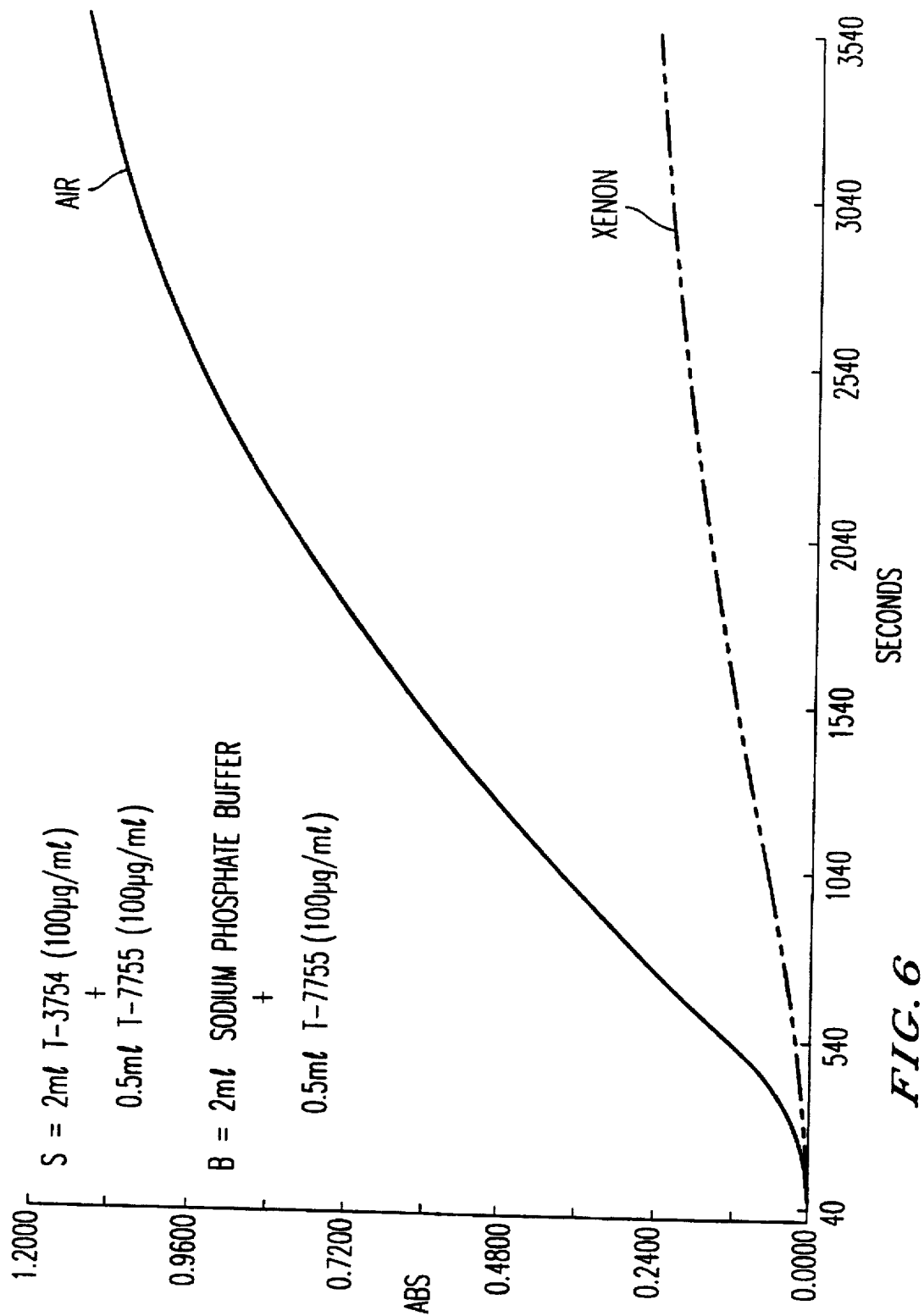
FIG. 6 demonstrates a very large inhibition of tyrosinase by xenon at 26° C.

FIG. 6 illustrates a very large inhibition of tyrosinase by xenon at 26° C. and is estimated to be approximately (area air run curve=11217µ, xenon=3037µ, total=14254µ, % total area air=78.69%, xenon=21.31, xenon total area=27.08% of air area, inhibition of air rate by xenon=72.92%. This rate of inhibition is extremely large relative to other conventional enzyme inhibitors.

Figure 7:
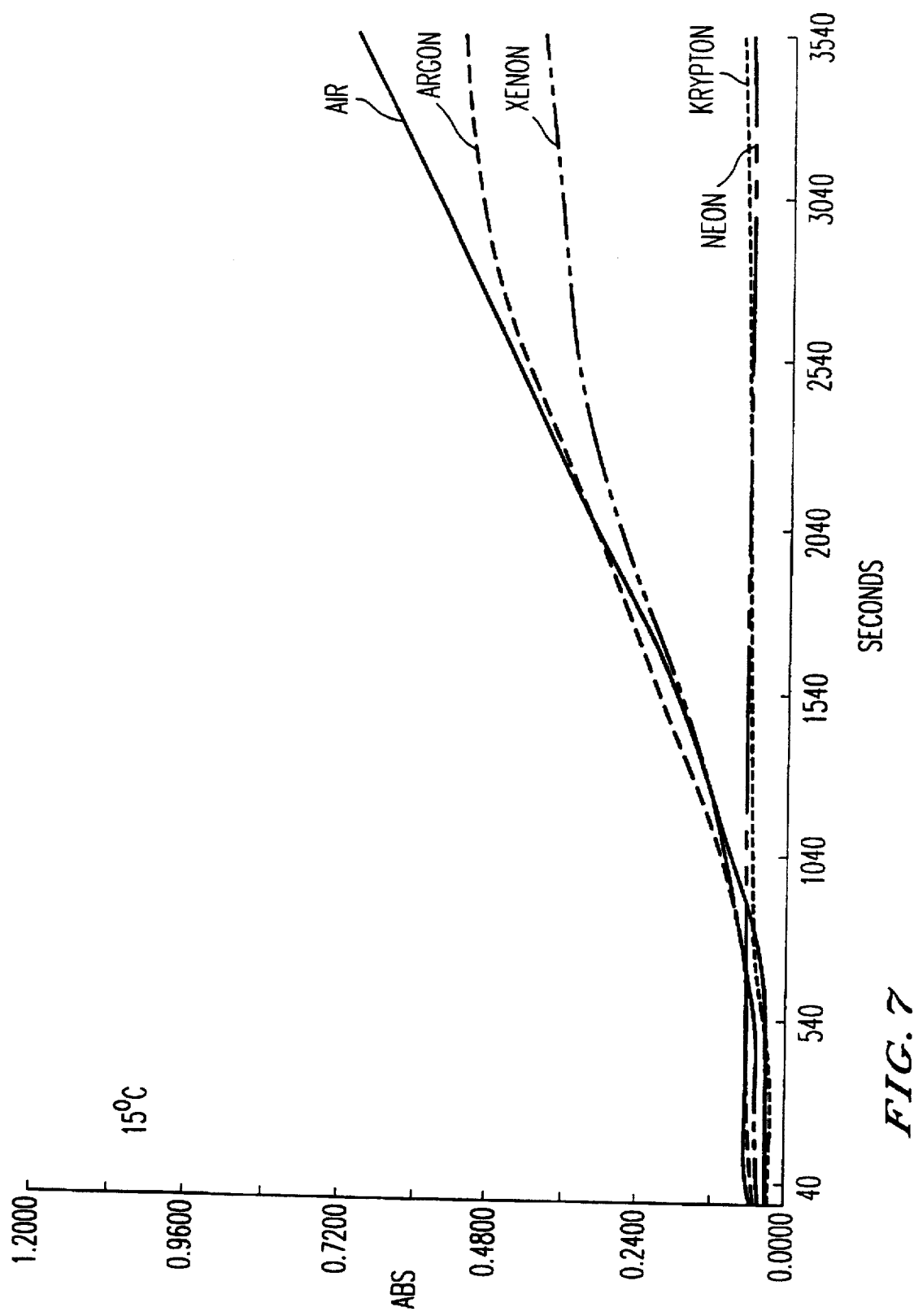
FIG. 7 illustrates that at 15° C., argon slightly inhibits equilibrium of the tyrosinase-L-tyrosine reaction; xenon has a small but significant inhibitory effect and neon and krypton exhibit a large inhibitory effect.

FIG. 7 illustrates that 15° C., argon slightly inhibits equilibrium of the tyrosinase-L-tyrosine reaction, xenon exhibits a small, but significant inhibitory effect, and neon and krypton exhibit strong effects. Oxygen and air exhibit approximately the same effect.

Figure 8:
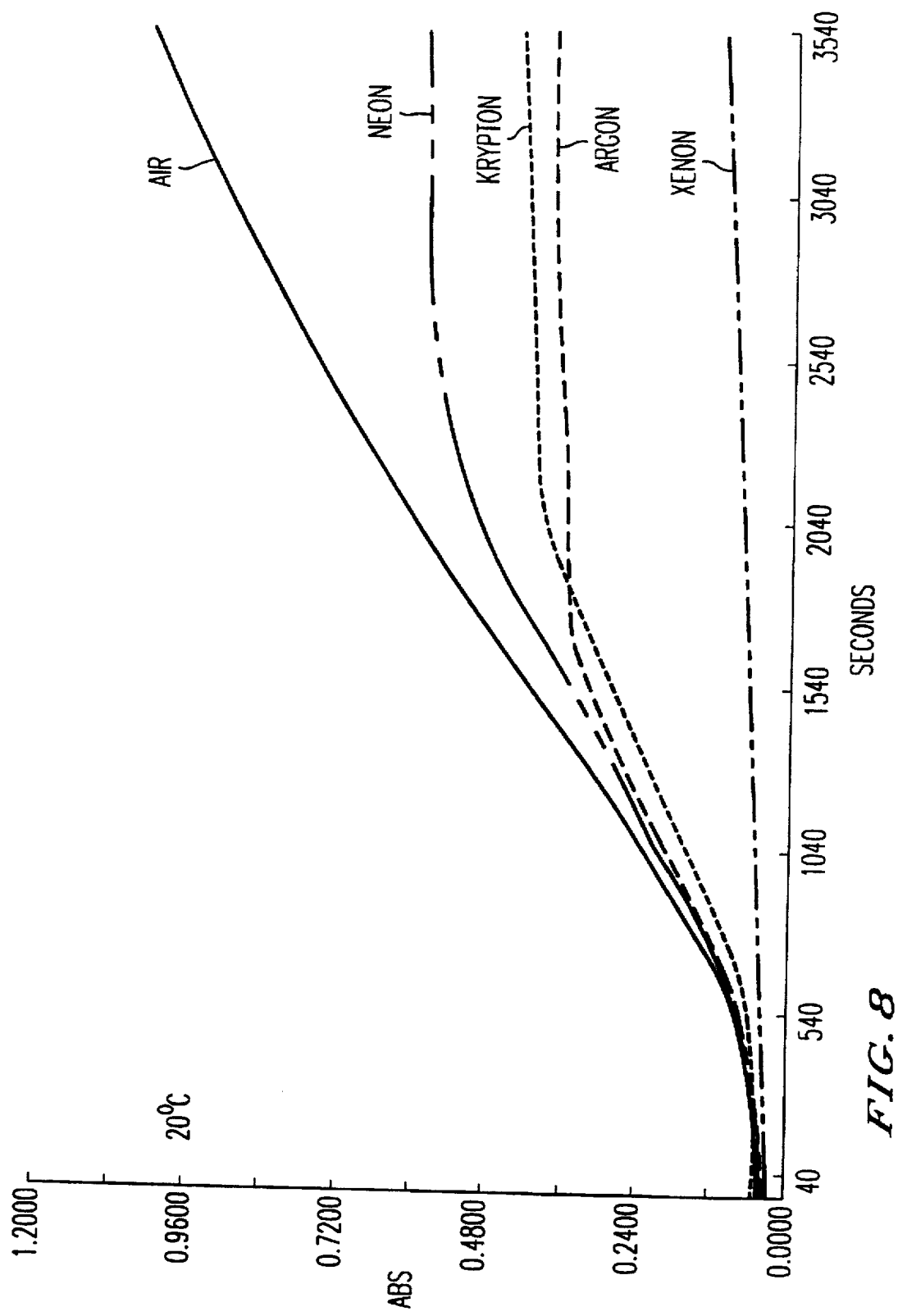
FIG. 8 illustrates the inhibiting effects of xenon, krypton, neon and argon on the tyrosinase-L-tyrosine reaction at 20° C.

FIG. 8 illustrates that at 20° C., xenon inhibits the tyrosinase-L-tyrosine reaction quite strongly, whereas the other gases neon, krypton and argon are all effective inhibitors.

Figure 9:
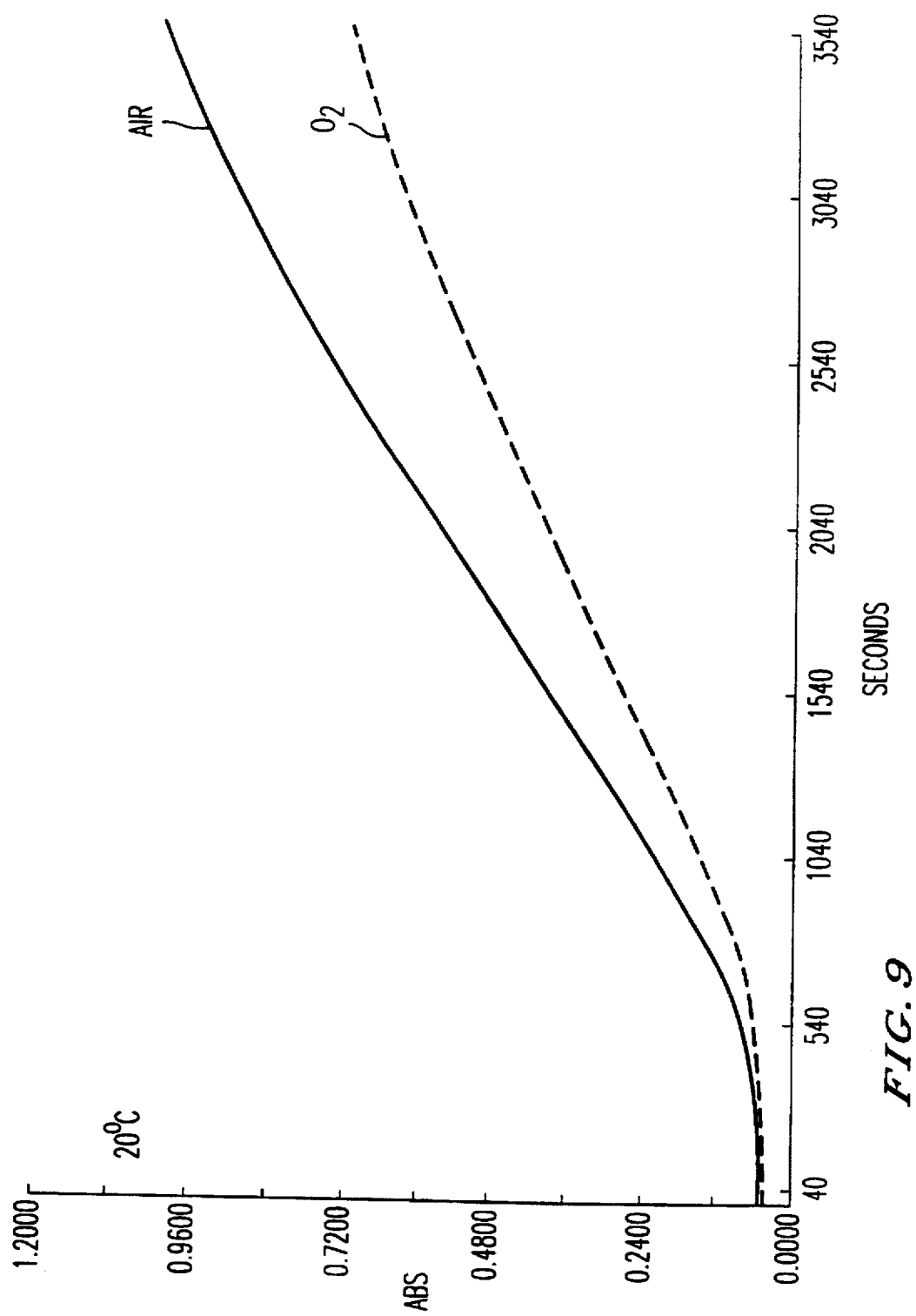
FIG. 9 illustrates that oxygen has no enhancing effect on the tyrosinase-L-tyrosine reaction at 20° C.

FIG. 9 illustrates that oxygen has only a moderate inhibitory effect on the tyrosinase-L-tyrosine reaction.

Figure 10:
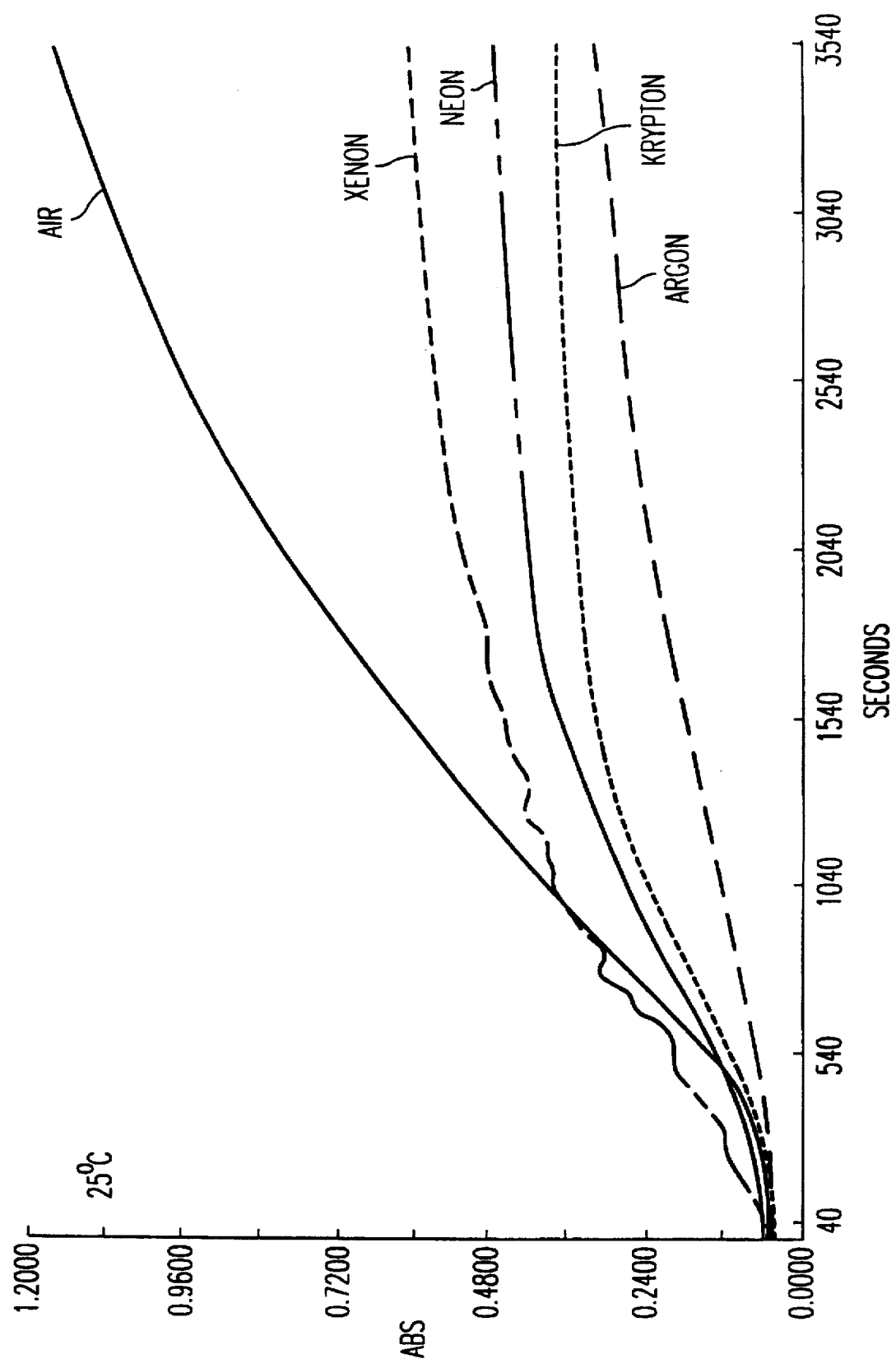
FIG. 10 illustrates the inhibitory effect of neon, argon, krypton and xenon on the tyrosinase-L-tyrosine reaction at 25° C.

FIG. 10 illustrates the strong inhibition at 20° C. of the tyrosinase-L-tyrosine reaction by argon, with krypton being almost of equal effect. However, the other gases indicated are also effective inhibitors.

Figure 11:
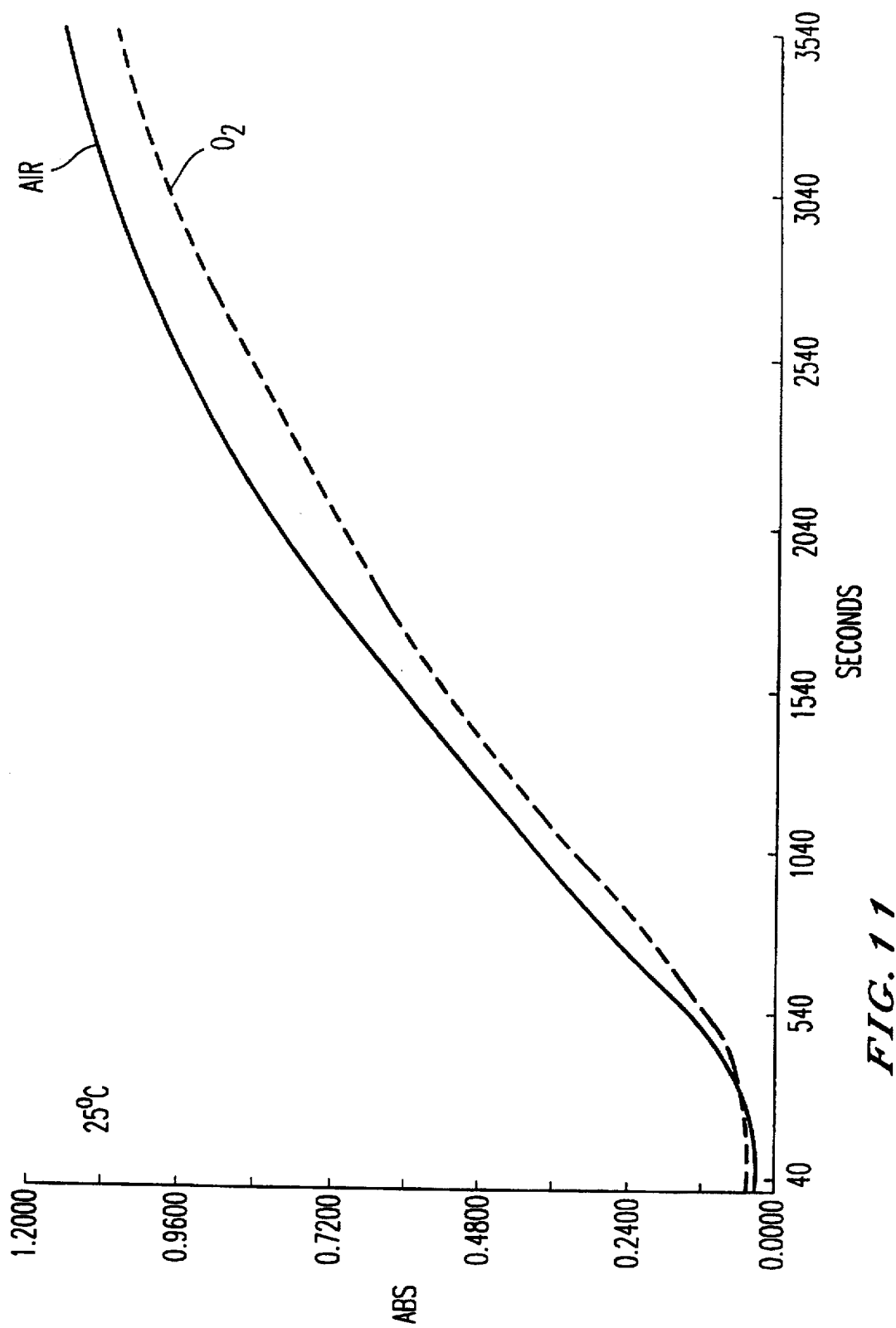
FIG. 11 illustrates that oxygen has no enhancing effect on the tyrosinase-L-tyrosine reaction at 25° C.

FIG. 11 illustrates that oxygen has only a slight inhibitory effect on the tyrosinase-L-tyrosine reaction of 25° C.

Figure 12:
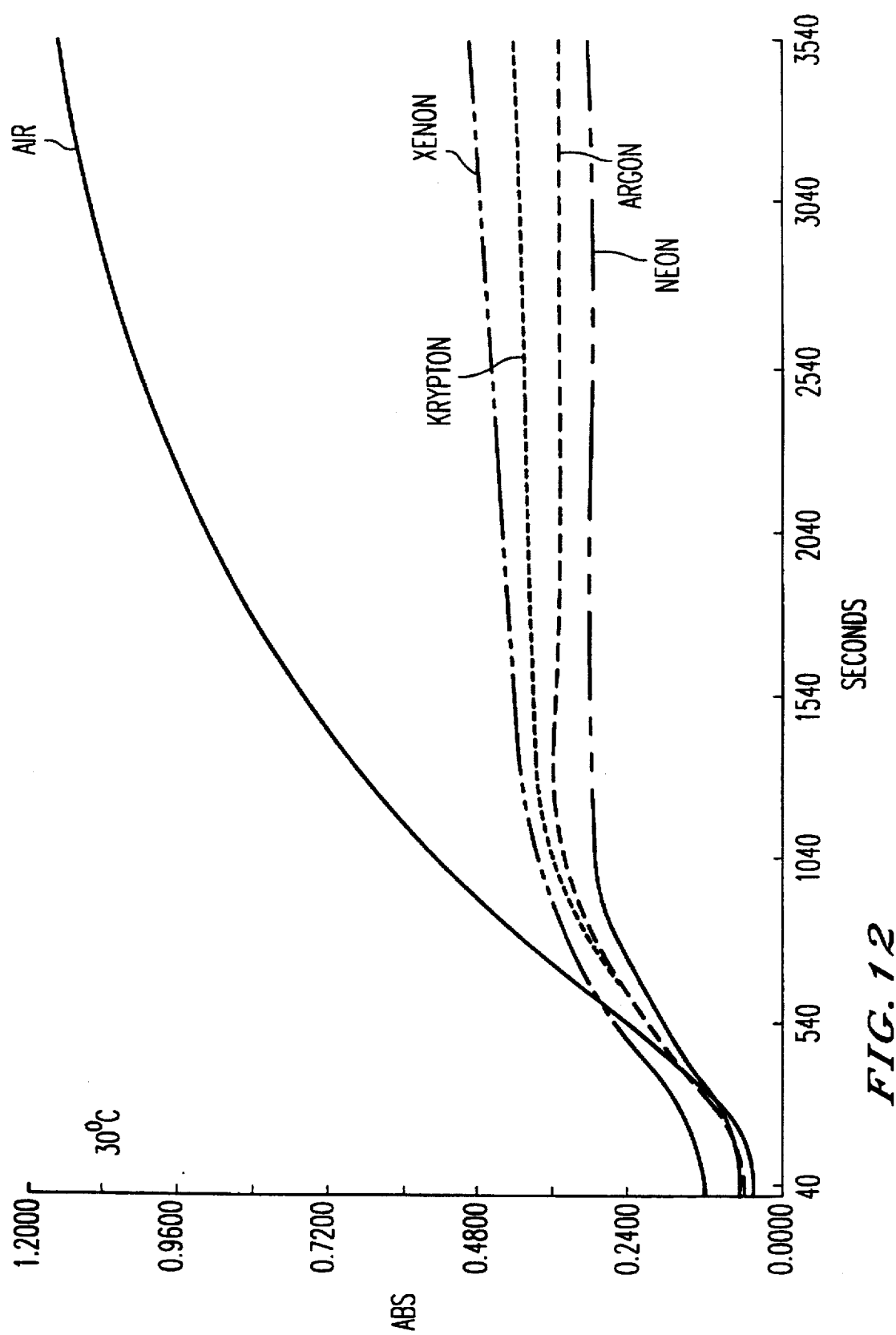
FIG. 12 illustrates the inhibitory effect of neon, argon, krypton and xenon on the tyrosinase-L-tyrosine reaction at 30° C.

FIG. 12 illustrates the inhibitory effect of neon, argon, krypton and xenon on tyrosinase activity at 30° C.

Figure 13:
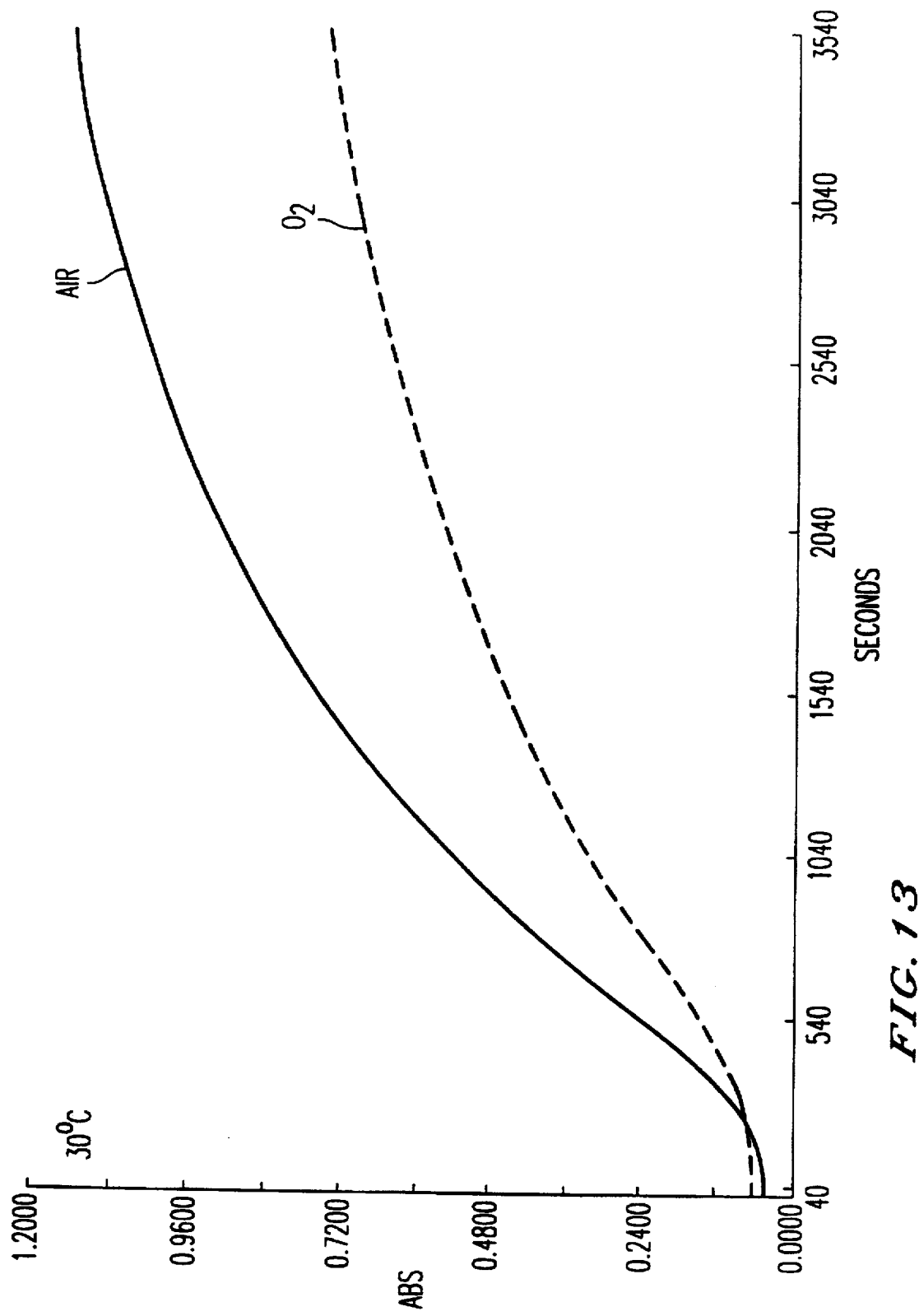
FIG. 13 illustrates that oxygen has no enhancing effect on the tyrosinase-L-tyrosine reaction at 30° C.

FIG. 13 illustrates the inhibitory effect of oxygen on tyrosinase-L-tyrosine activity at 30° C.

Figure 14:
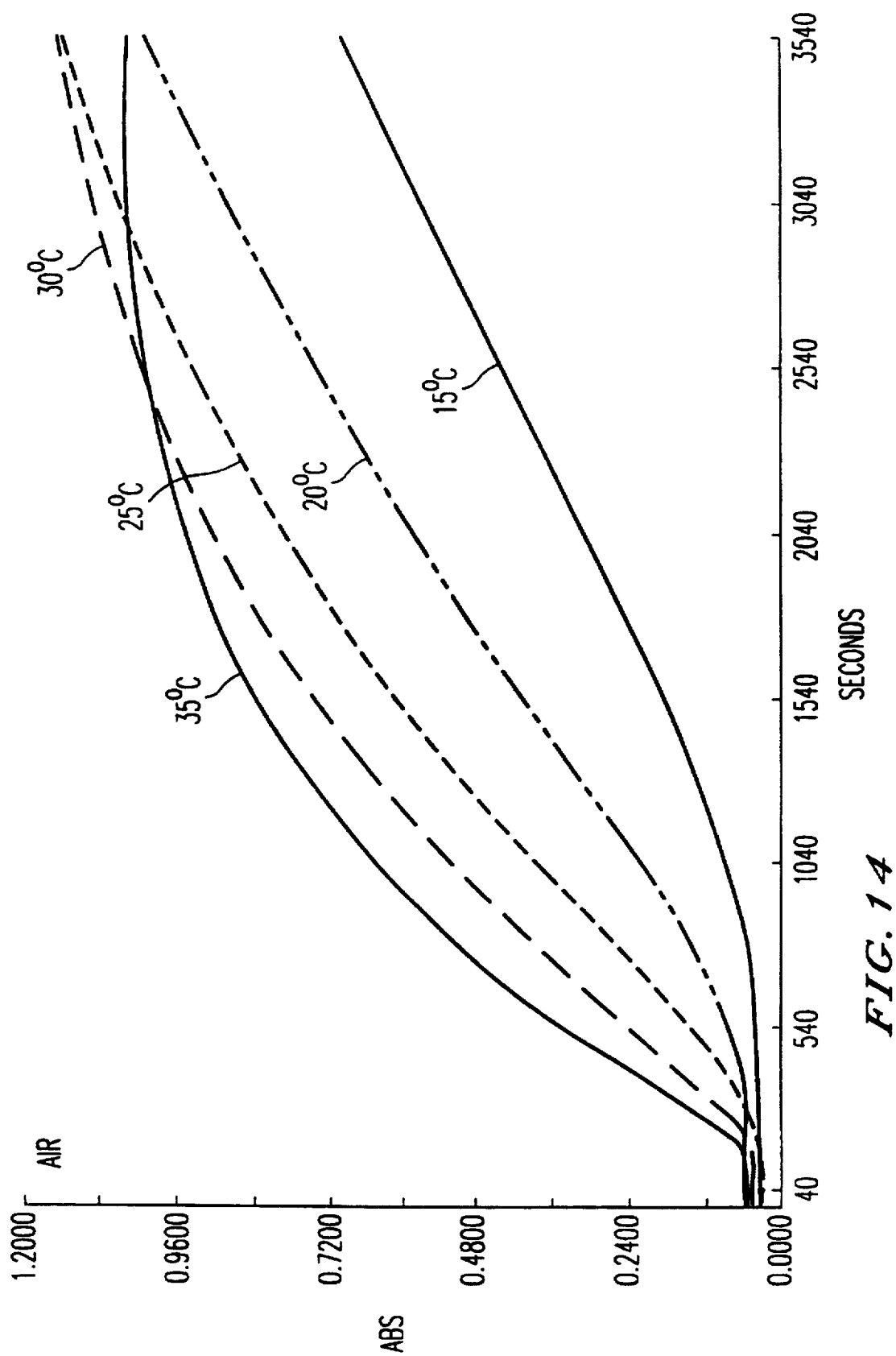
FIG. 14 illustrates a standard run in air at various temperatures, and demonstrates that rate changes are directly attributable to oxygen solubility differences.

FIG. 14 illustrates a standard tyrosinase-L-tyrosine reaction run in air showing rate changes directly attributable to oxygen solubility differences. The curves obtained with oxygen instead of air are identical.

Figure 15:
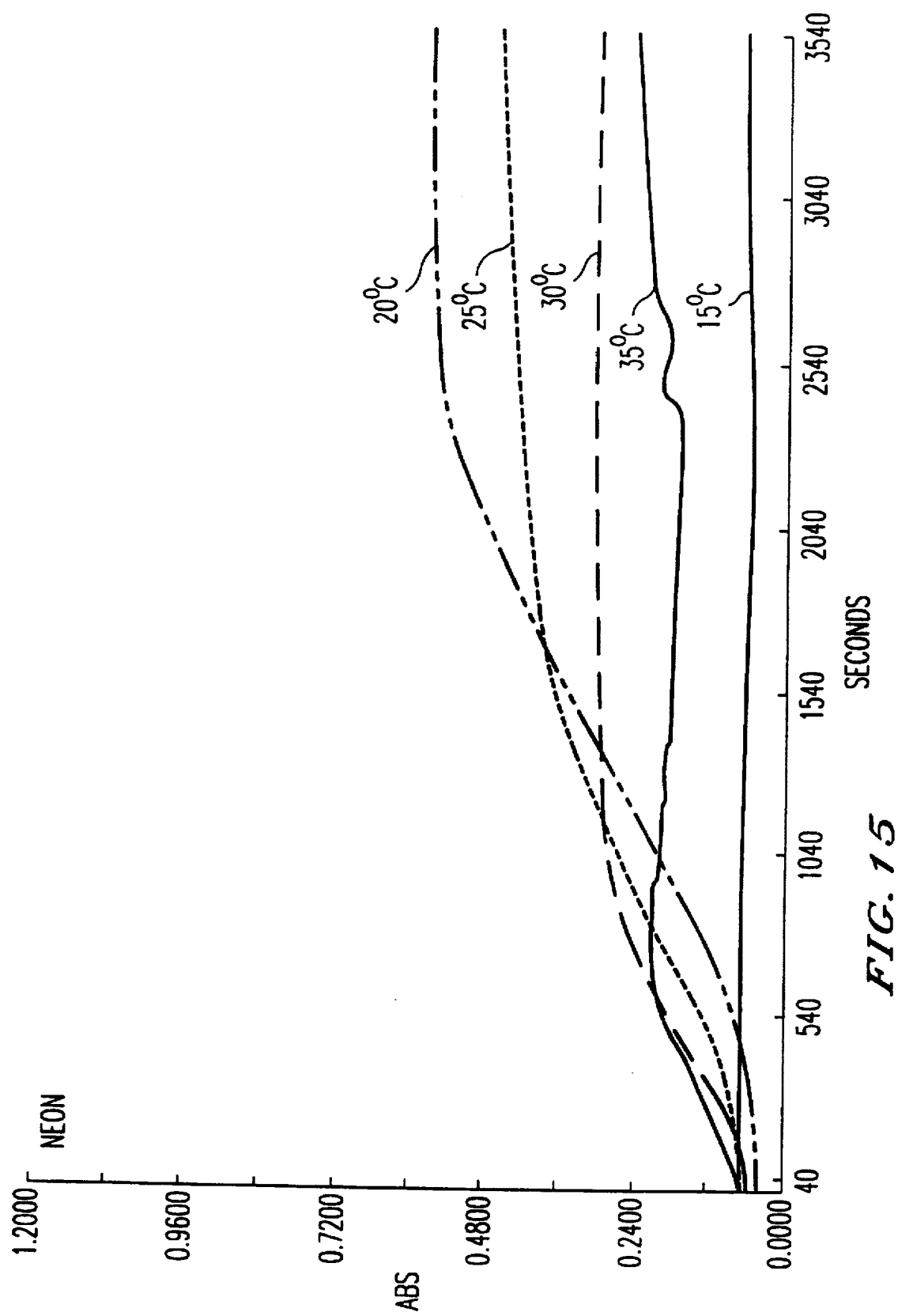
FIG. 15 illustrates the inhibitory effect of neon on the tyrosinase-L-tyrosine reaction which is positively temperature dependent.

FIG. 15 illustrates an inhibitory effect with neon which is temperature dependent.

Figure 16:
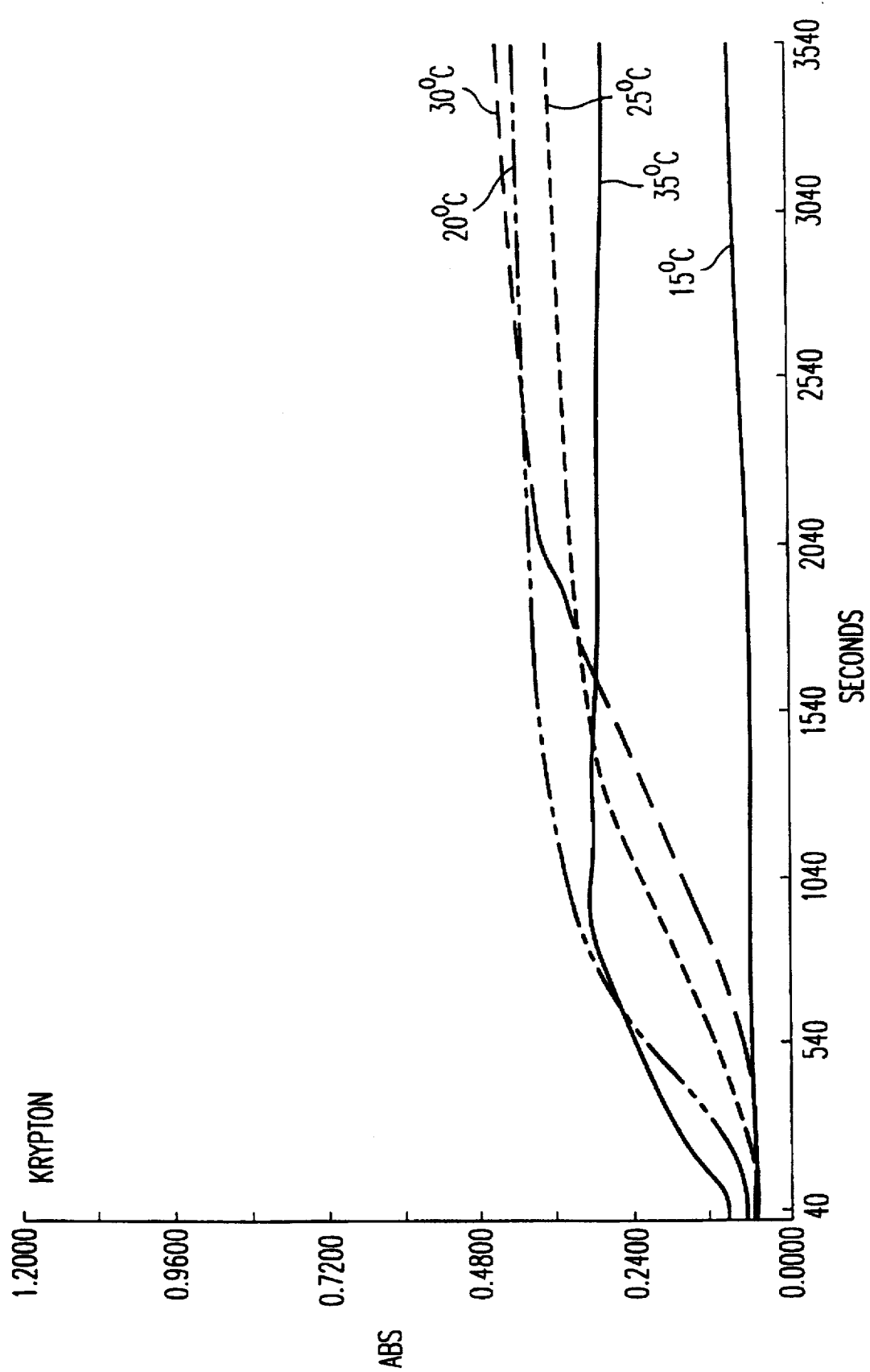
FIG. 16 illustrates the direct inverse (negative) relationship between the ability of krypton to inhibit tyrosinase and temperature.

FIG. 16 illustrates a direct inverse (negative) relationship between the ability of krypton to inhibit tyrosinase and temperature.

Figure 17:
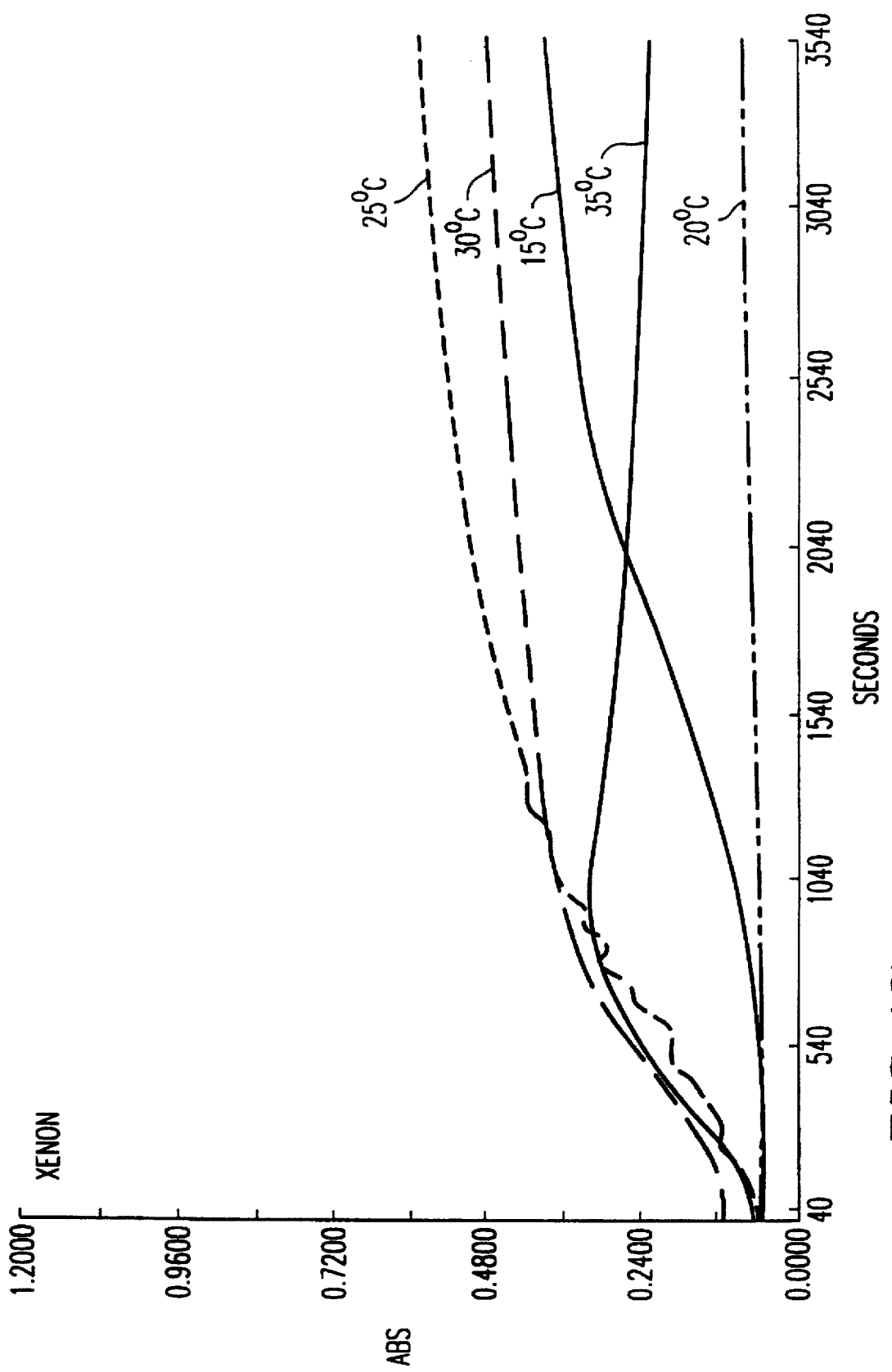
FIG. 17 illustrates the inhibition of tyrosinase-L-tyrosine equilibrium with xenon, which interacts inversely with temperature.

FIG. 17 illustrates that xenon inhibits the equilibrium of the tyrosinase-L-tyrosine reaction better than other gases, byt depresses the rate only as well as krypton and argon for this reaction. Further, the variability in curve shape is high, which strangely suggests a direct active site interaction with tyrosinate. Xenon interacts inversely with temperature and shares a dynamic transition of effect between 20° C. and 25° C.

Figure 18:
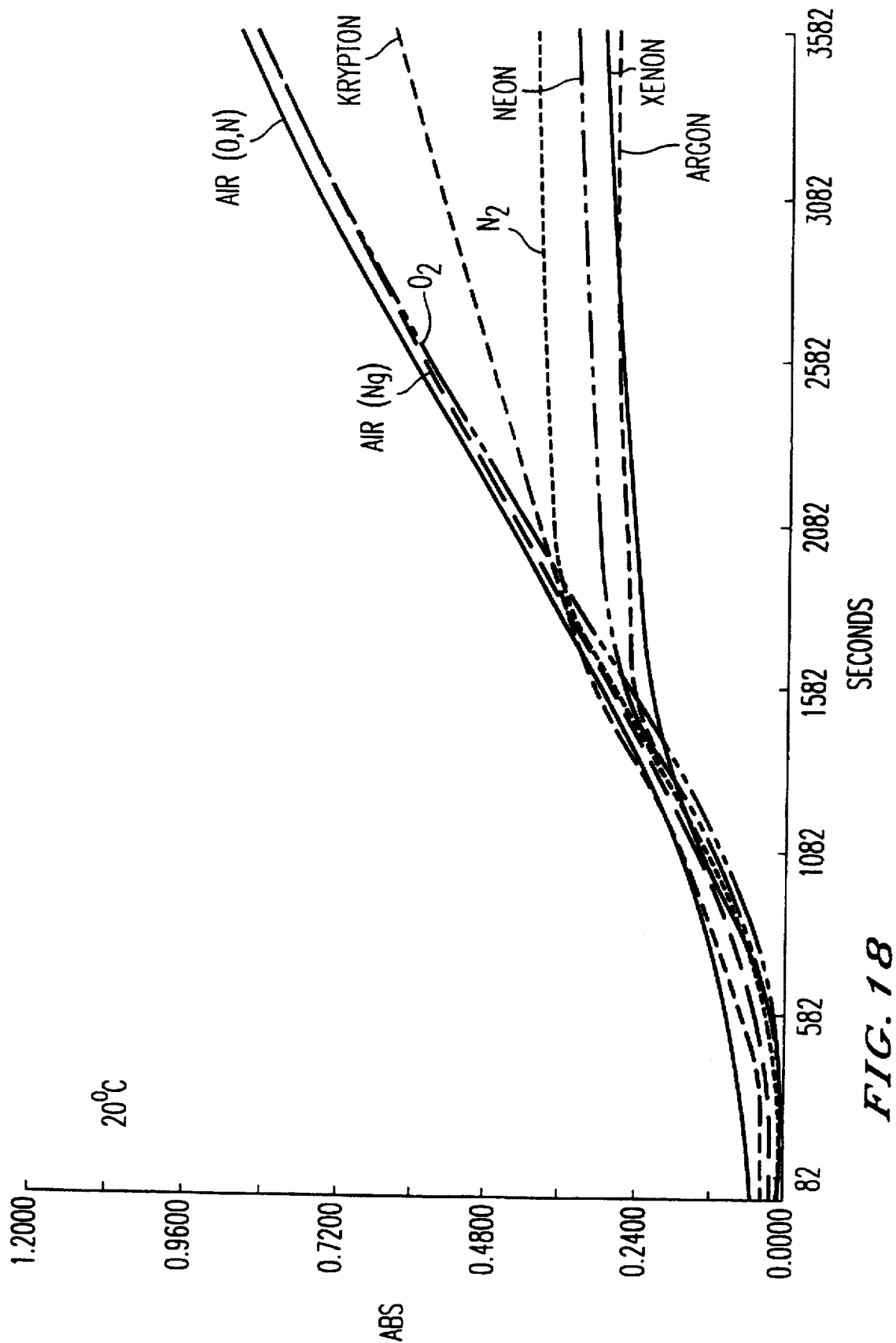
FIG. 18 illustrates that at 20° C., oxygen does not enhance the tyrosinase-L-tyrosine reaction, whereas argon, xenon and neon each dramatically inhibit the reaction. Krypton has a lesser inhibitory effect as does nitrogen.

FIG. 18 illustrates that at 20° C. argon, xenon and neon all dramatically inhibit tyrosinase activity, whereas krypton has a lesser effect. Nitrogen also inhibits the reaction fairly well, however, oxygen exhibits little effect.

Figure 19:
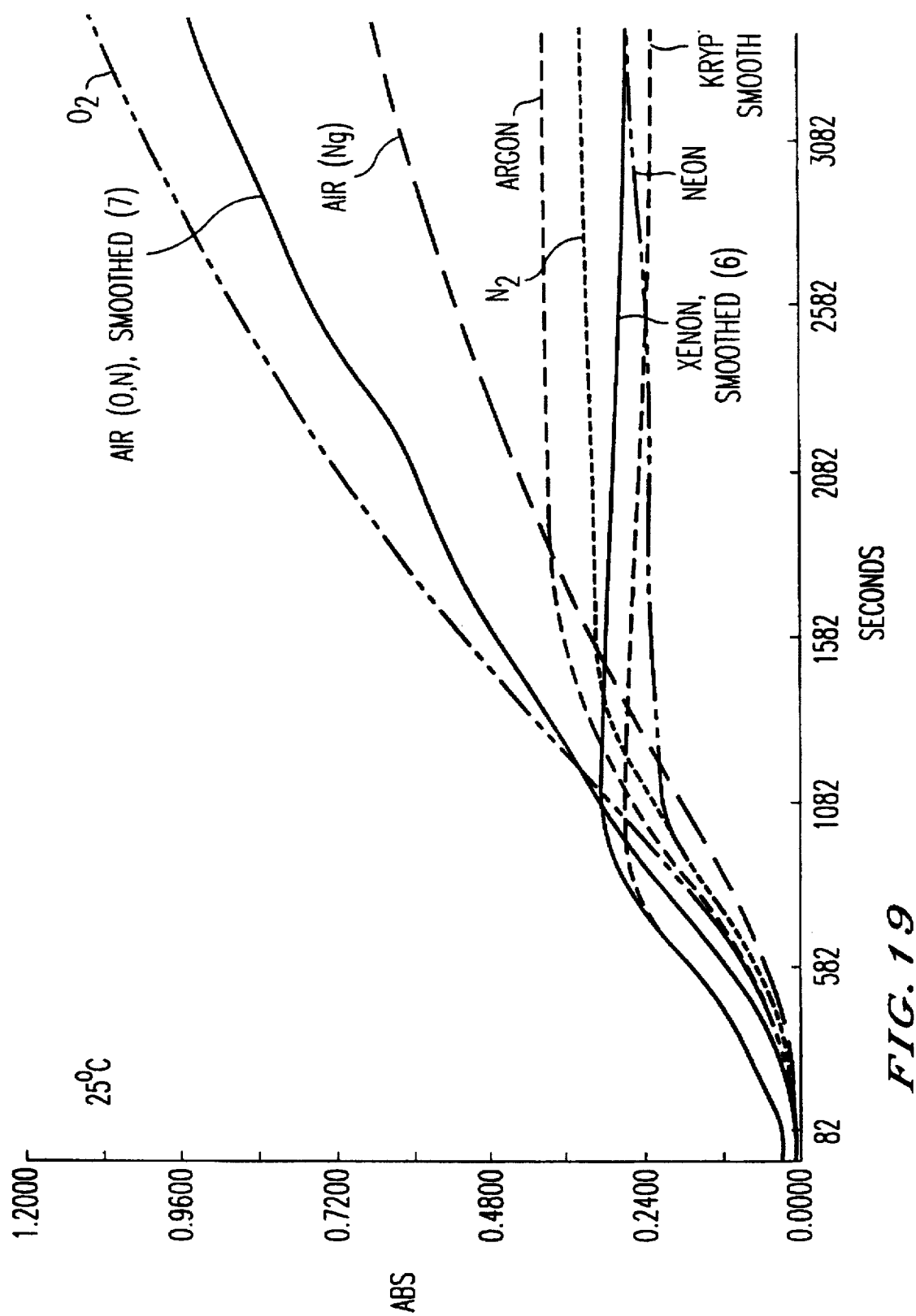
FIG. 19 illustrates that at 25° C., argon and nitrogen inhibit the tyrosinase-L-tyrosine to a lesser extent than the noble gases, and oxygen enhances the reaction.

FIG. 19 illustrates that at 25° C., argon and nitrogen inhibit at a lesser level than the other noble gases, whereas oxygen enhances the reaction. The small difference in curve shape between the krypton-xenon and neon-argon curve pairs is highly significant due to the likely relative effects of Van der Waals exclusion and oxygen dilution.

Figure 20:
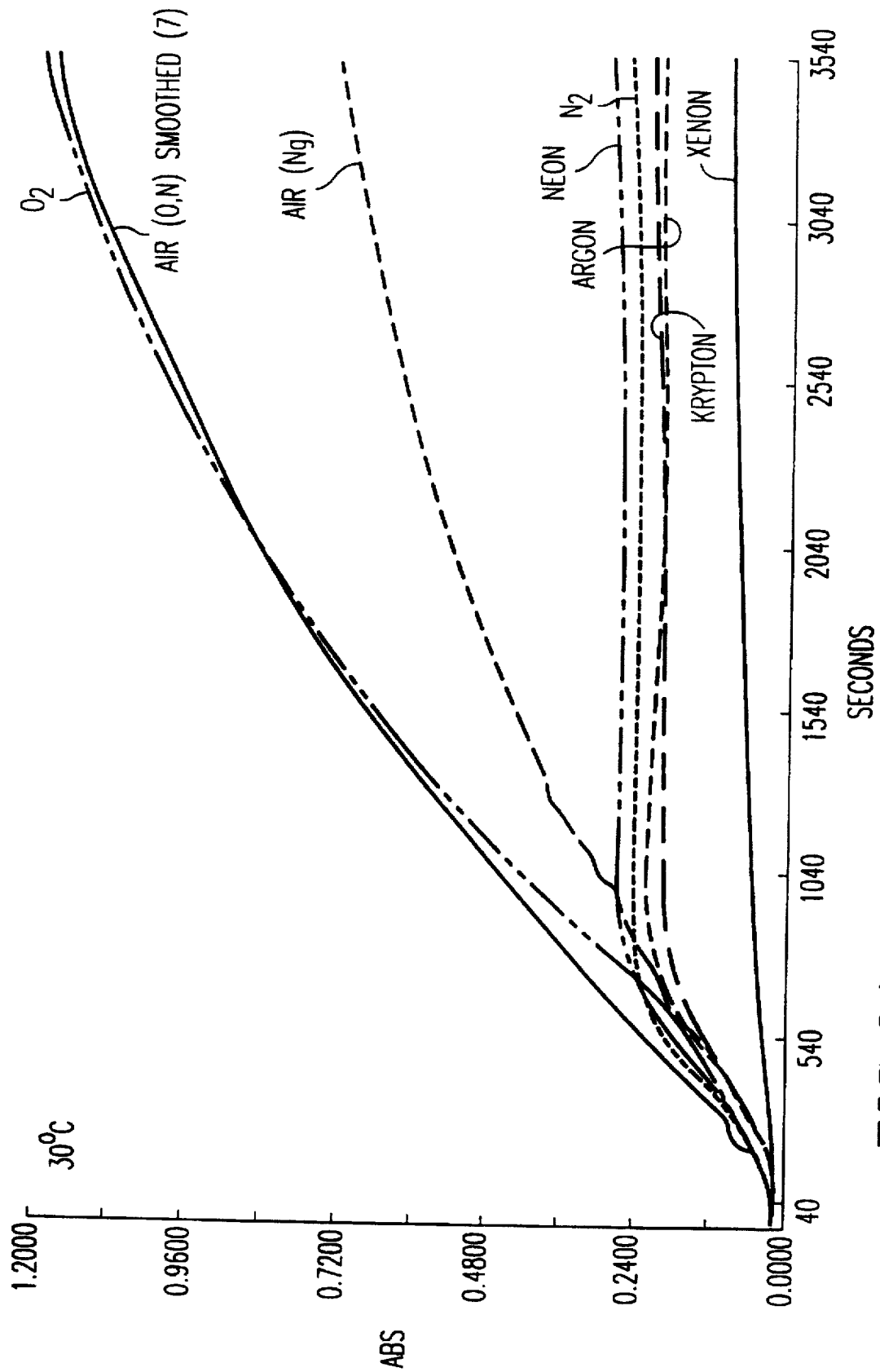
FIG. 20 illustrates that at 30° C., oxygen no longer enhances the tyrosinase-L-tyrosine reaction due to lessened solubility.

FIG. 20 illustrates that at 30° C., oxygen no longer enhances tyrosinase activity due to lessened solubility. Xenon inhibits the reaction much better than other gases, although all are effective.

Figure 21:
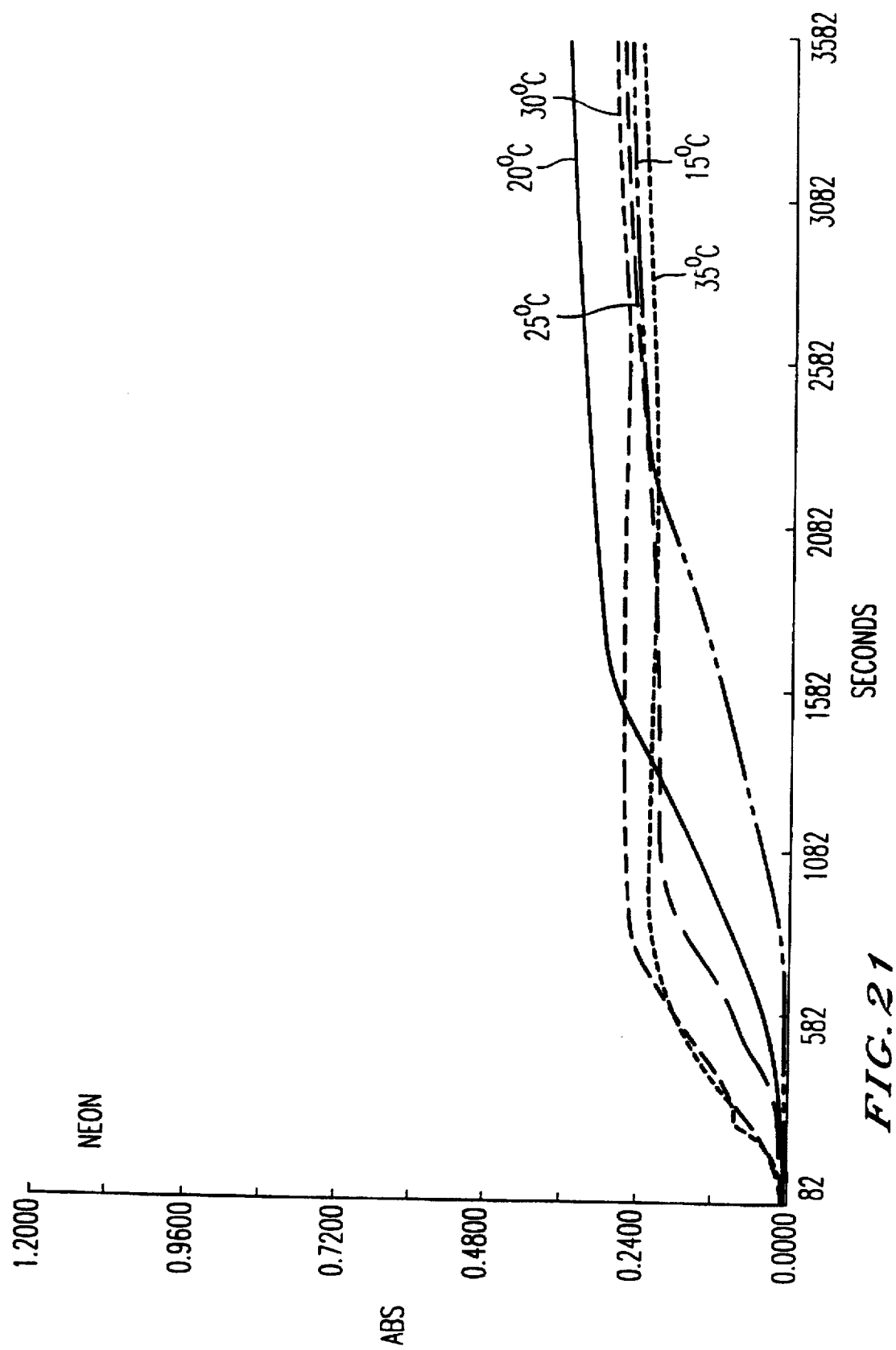
FIG. 21 illustrates the inhibition of the tyrosinase-L-tyrosine reaction by neon at various temperatures, and shows a transition between 20° C. and 25° C.

FIG. 21 illustrates the inhibition of tyrosinase activity by neon, with an activity transition occuring between 20° C. and 25° C.

Figure 22:
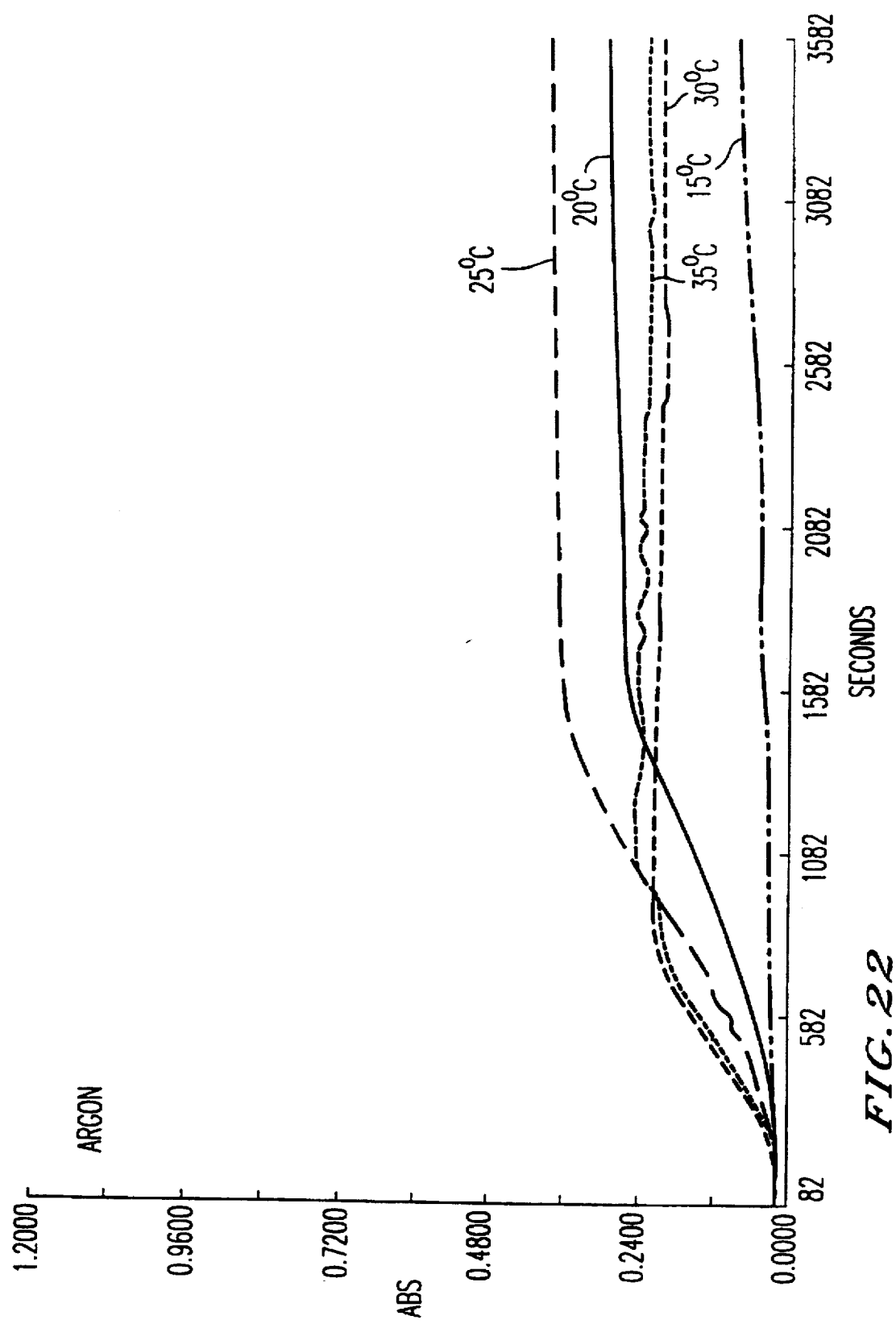
FIG. 22 illustrates the inhibition of the tyrosinase-L-tyrosine reaction by argon at various temperatures.

FIG. 22 illustrates the inhibition of tyrosinase activity by argon, showing better inhibition by argon at 20° C. than neon, but less inhibition at 25° C. than neon. These differences are considered to be directly attributable to solubility/oxygen diffusabilities.

Figure 23:
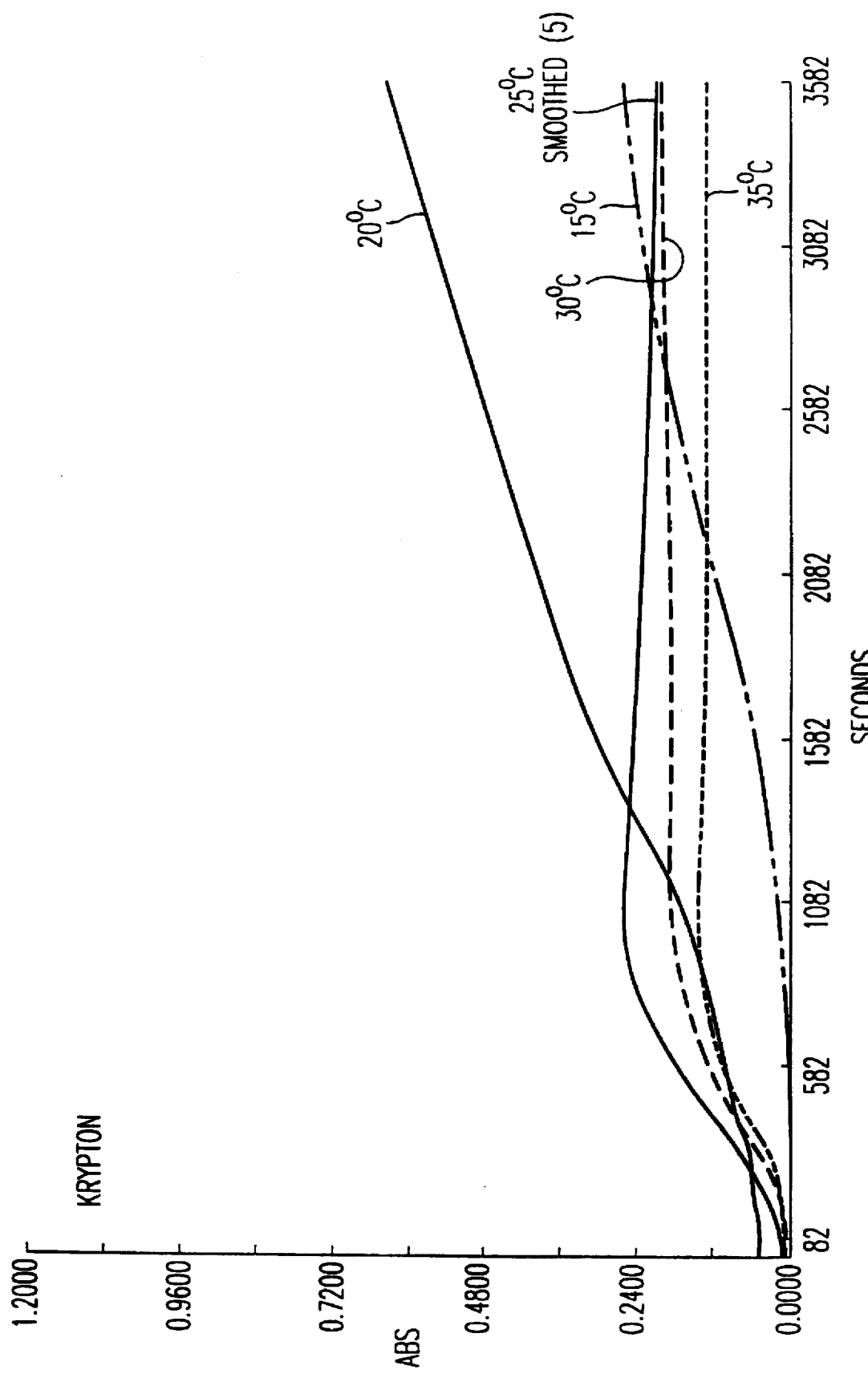
FIG. 23 illustrates the inhibition of the tyrosinase-L-tyrosine reaction by krypton at various temperatures.
Figure 24:
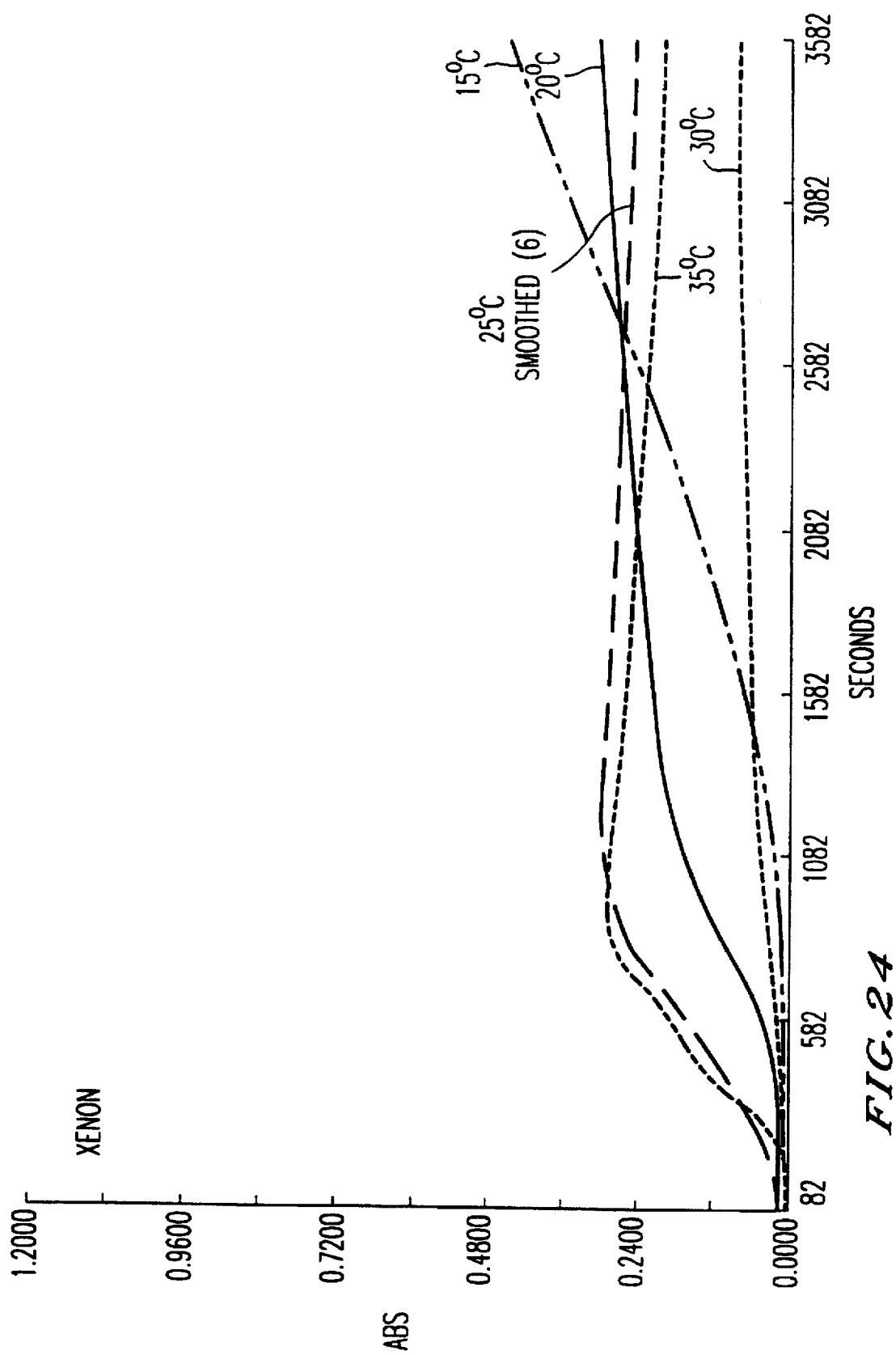
FIG. 24 illustrates the inhibition of the tyrosinase-L-tyrosine reaction by xenon at various temperatures.

FIG. 23 illustrates the inhibition of tyrosinase activity by krypton with an activity transition occuring between 20 ° C. and 25° C. This provides strong evidence for a direct interaction between the gas and the enzyme active site, FIG. 24 illustrates the existence of at least two activity transitions for xenon in the inhibition of tyrosinase activity.

A first activity transition is between 25° C. and 30° C., and a second is between 30° C. and 35° C. A third activity transition may exist between 20° C. and 25° C. These trnasitions provide strong evidence for a direct interaction between the gas and the enzyme active site.

Figure 25:
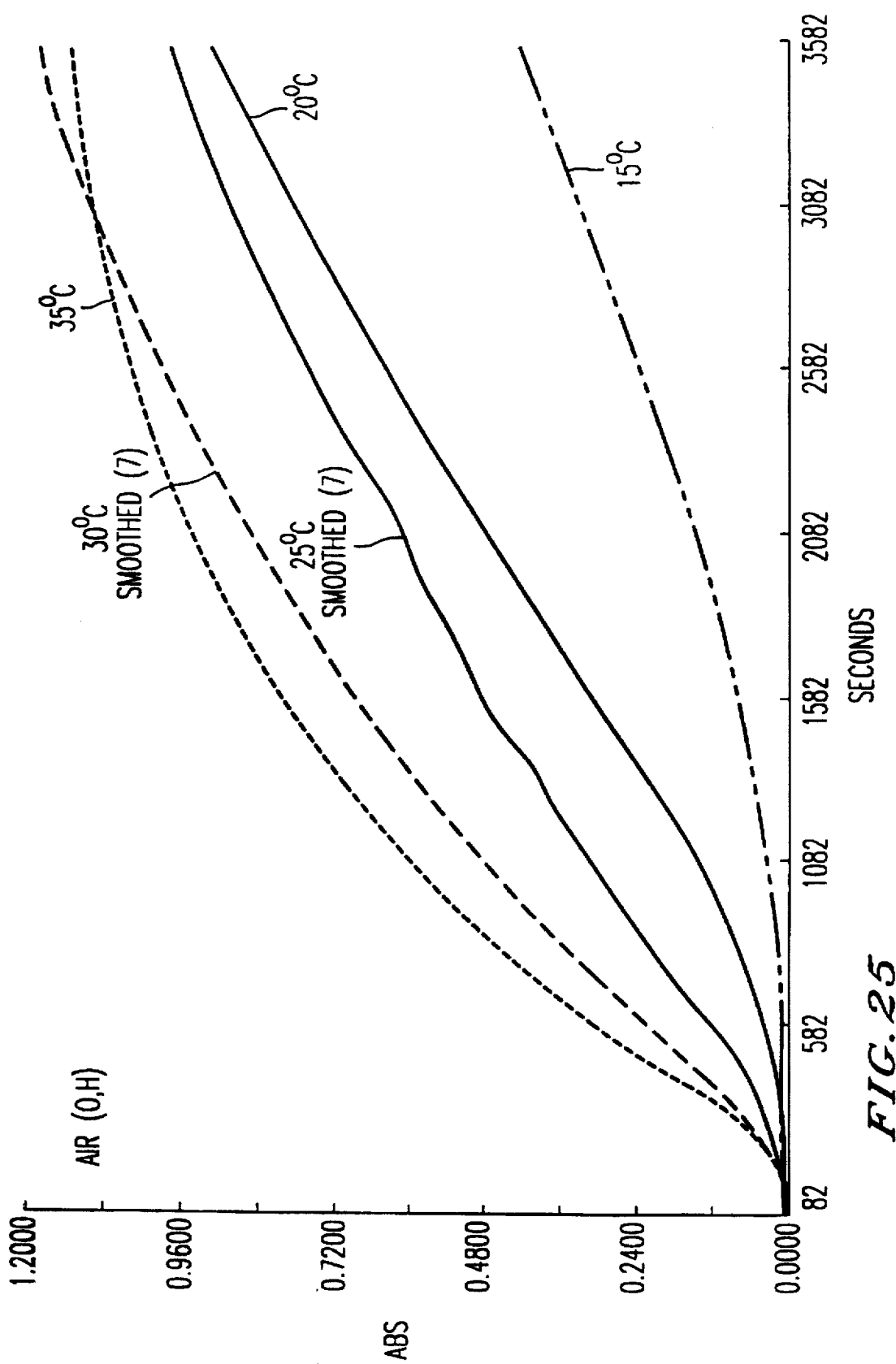
FIG. 25 illustrates the inhibition of the tyrosinase-L-tyrosine reaction purely by a solubility mechanism involving the displacement of oxygen from solution.

FIG. 25 illustrates the inhibition of tyrosinase purely by a solubility mechanism involving the displacement of oxygen from solution. Air shows the expected dissolution—driven rate pattern, while oxygen saturates at 30° C.

Figure 26:
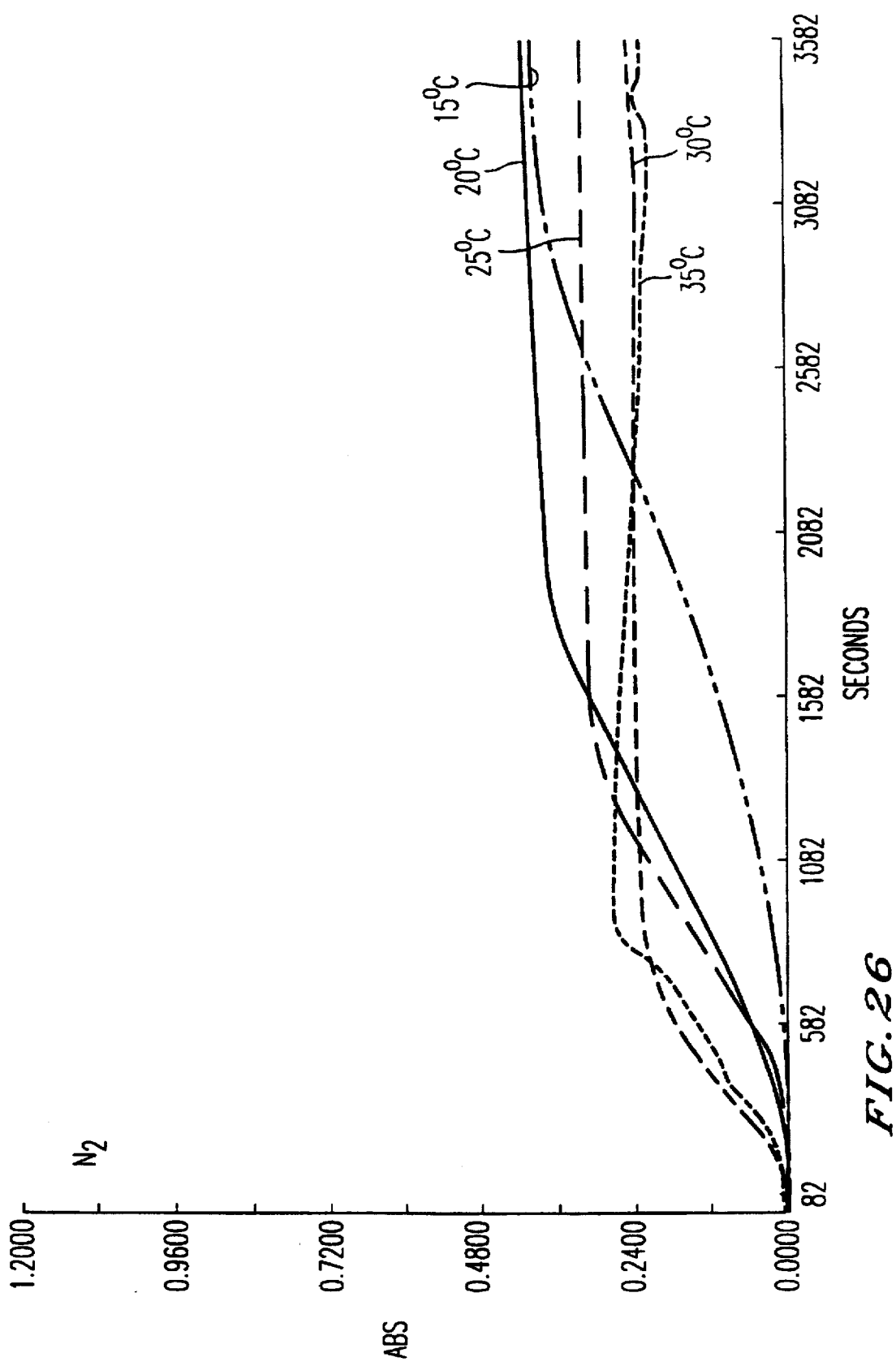
FIG. 26 illustrates the inhibition of tyrosinase activity by nitrogen.

FIG. 26 illustrates the inhibition of tyrosinase activity by nitrogen. Nitrogen can only inhibit enzymes by a solubility mechanism involving the displacement of oxygen from solution, but is effective in inhibiting tyrosinase activity. A transitional maxima is observed after 20° C. The difference between the nitrogen curves and noble gas curves represents potential active site inhibition. In most cases, these differences are significant for each gas at at least one temperature.

Figure 27:
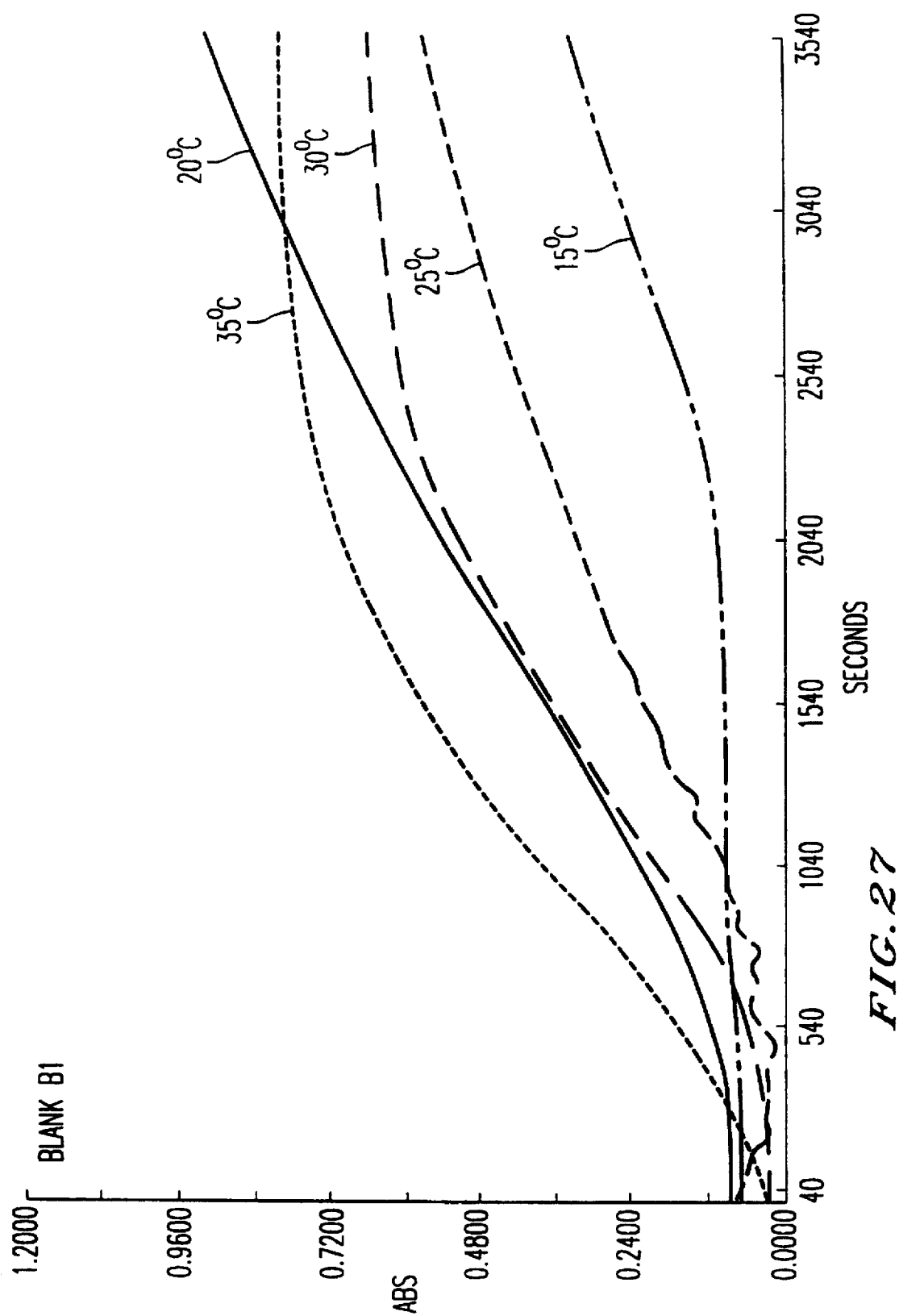
FIG. 27 illustrates the large difference in xenon activity between 20° and 25° C.

FIG. 27 illustrates the large difference in xenon activity between 20° C. and 25° C. This corresponds with an enzyme active site optical temperature.

Figure 28:
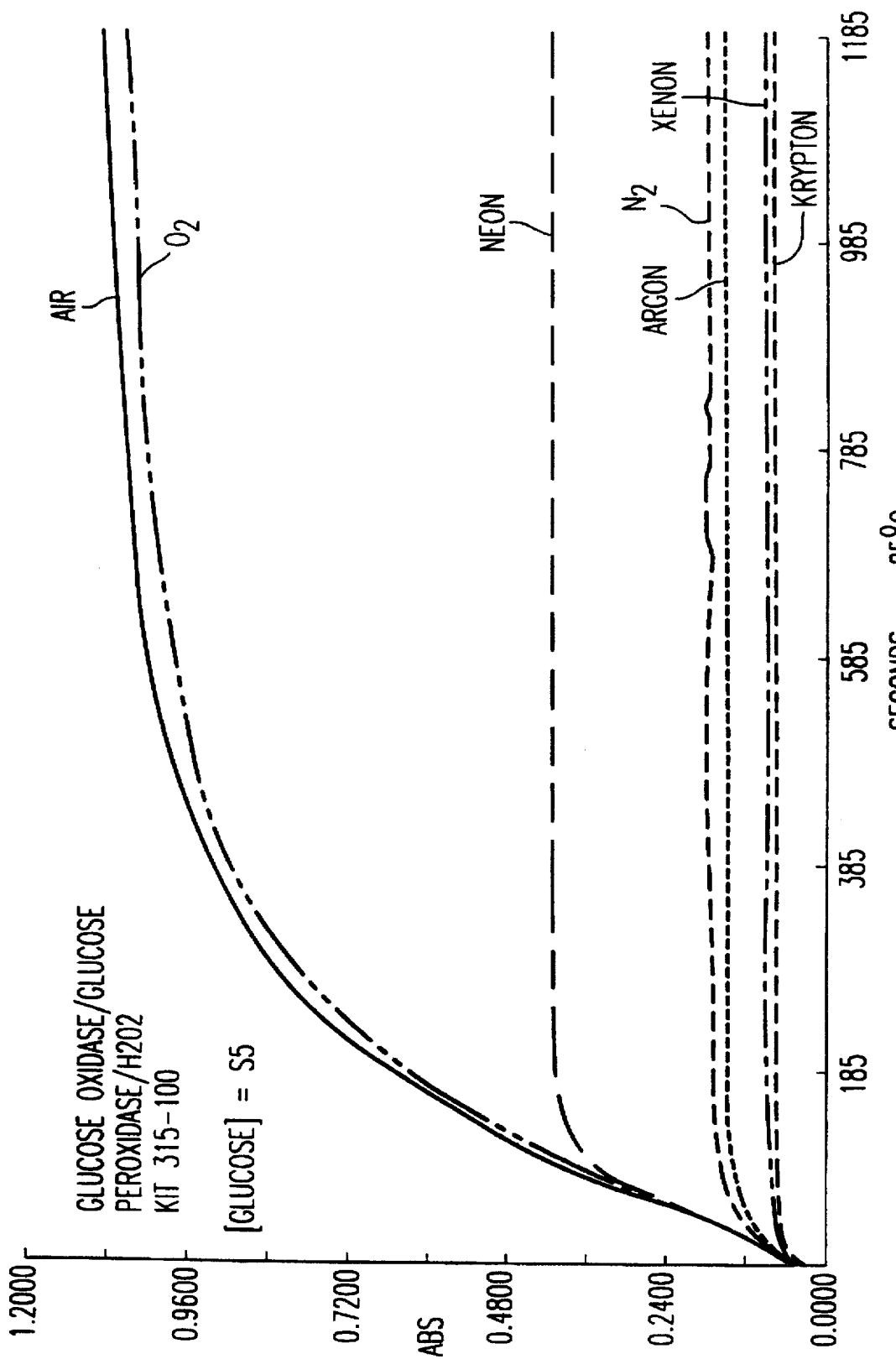
FIG. 28 illustrates the inhibition of glucose oxidase by krypton, xenon, argon, nitrogen and neon.

FIG. 28 illustrates the inhibition of glucose oxidase by krypton, xenon, argon, nitrogen and neon.

Figure 29:
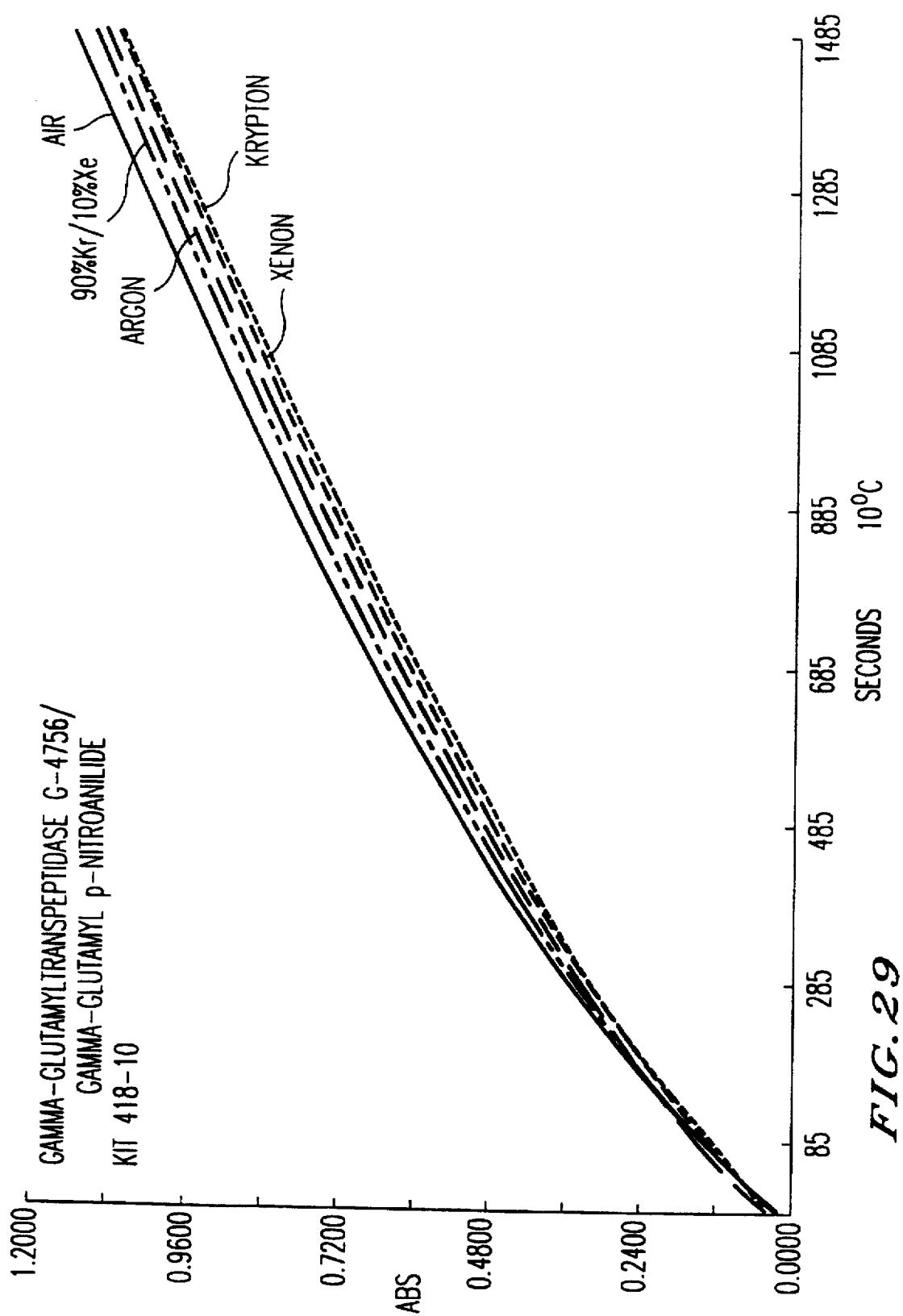
FIG. 29 illustrates the inhibition of α-glutamyltranspeptidase by krypton, xenon, argon and a mixture of krypton and xenon.

FIG. 29 illustrates the inhibition of α-glutamyltranspeptidase by krypton, xenon, argon and a mixture of krypton and xenon.

Figure 30:
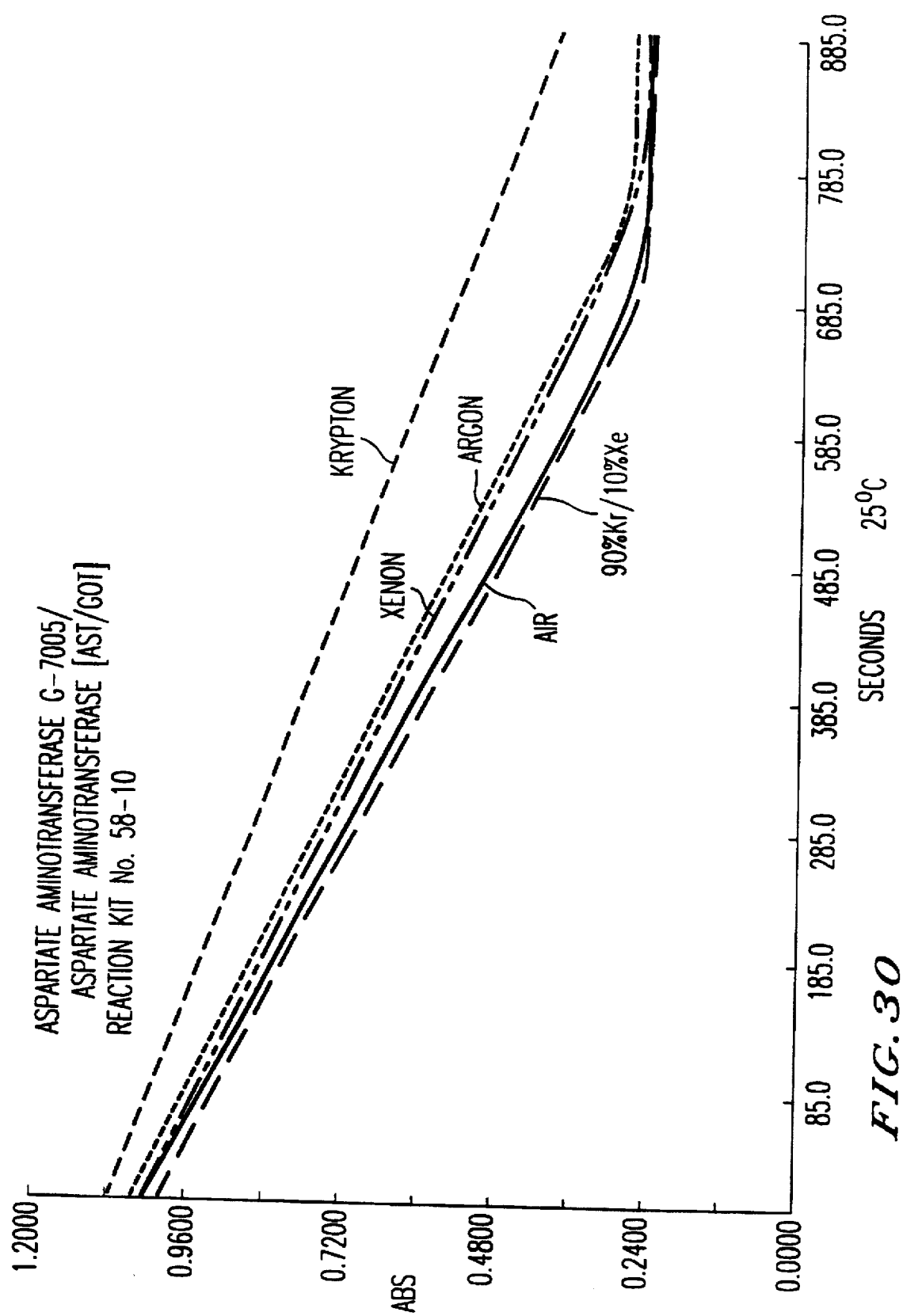
FIG. 30 illustrates the inhibition of aspartate aminotransferase by krypton, xenon, argon and a mixture of krypton and xenon.

FIG. 30 illustrates the inhibition of aspartate aminotransferase by krypton, xenon, argon and a mixture of krypton and xenon.

Figure 31:
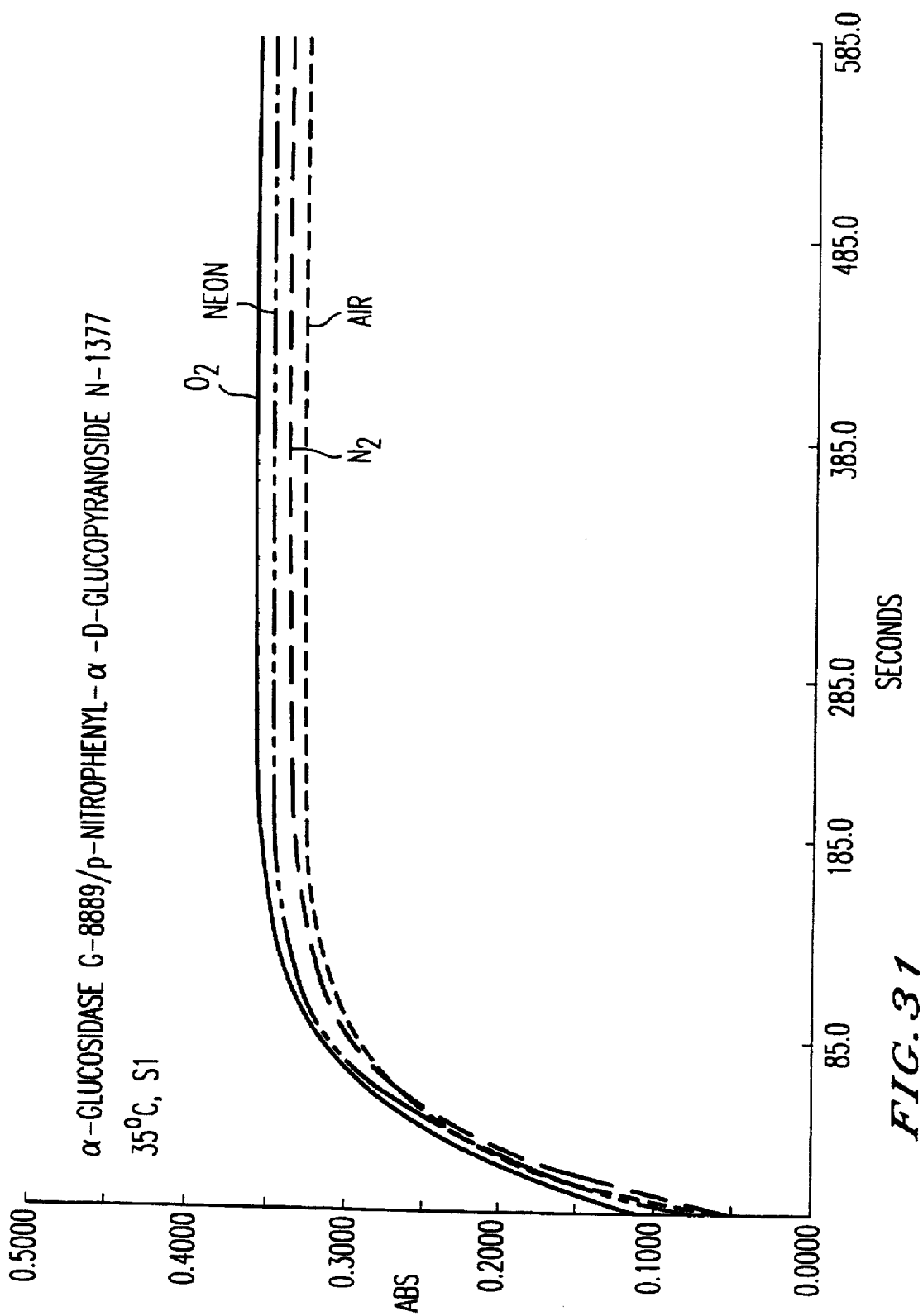
FIG. 31 illustrates the enhancement of α-D-glucosidase by nitrogen, neon and oxygen.

FIG. 31 illustrates the enhancement of α-D-glucosidades by $SF_6$, argon, nitrogen, neon and oxygen.

Figure 32:
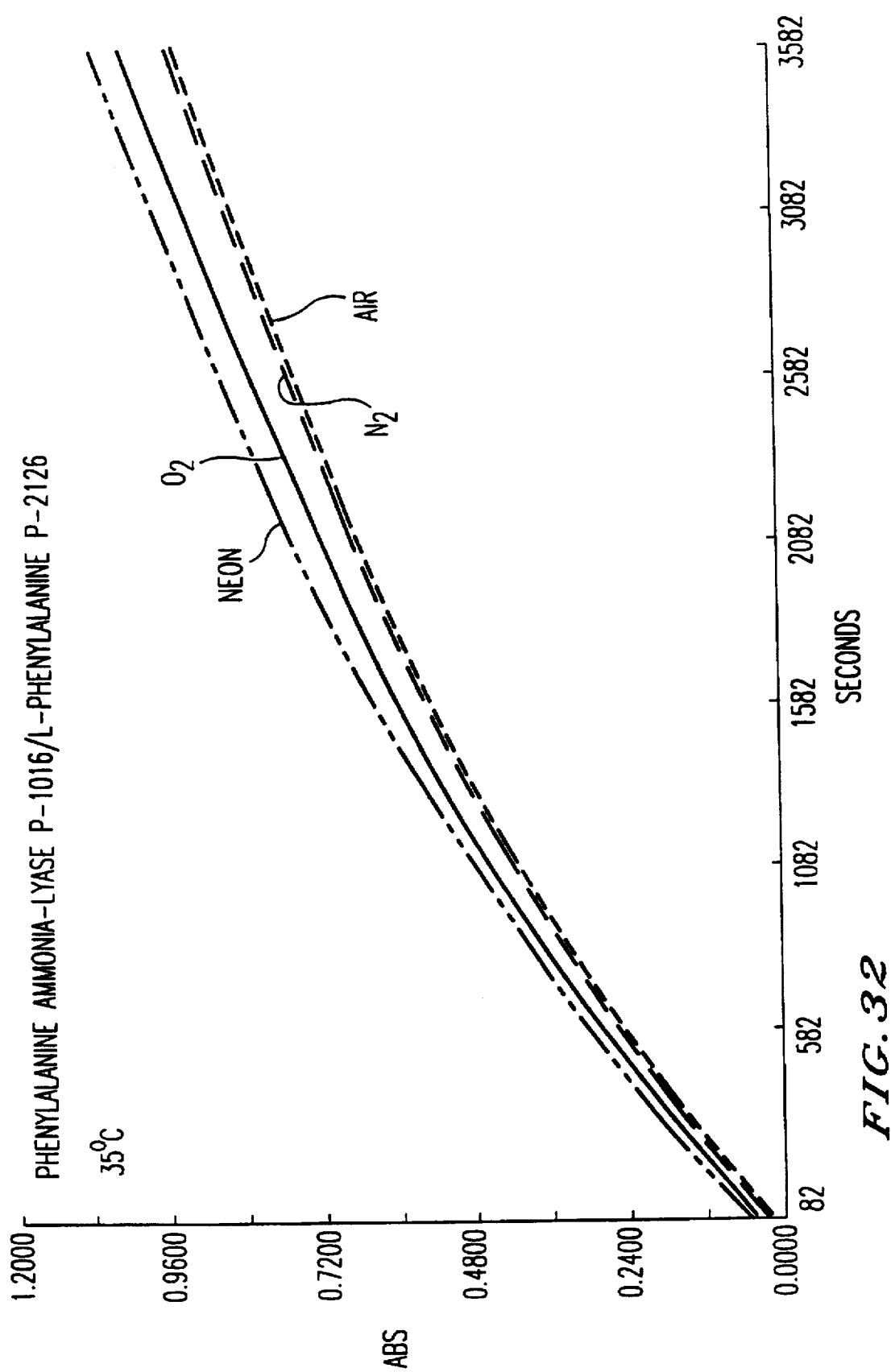
FIG. 32 illustrates the enhancement of phenylalanine ammonia-lyase by neon, oxygen and nitrogen.

FIG. 32 illustrates the enhancement of phenylalanine ammonia-lyase by neon, oxygen and nitrogen.

Figure 33:
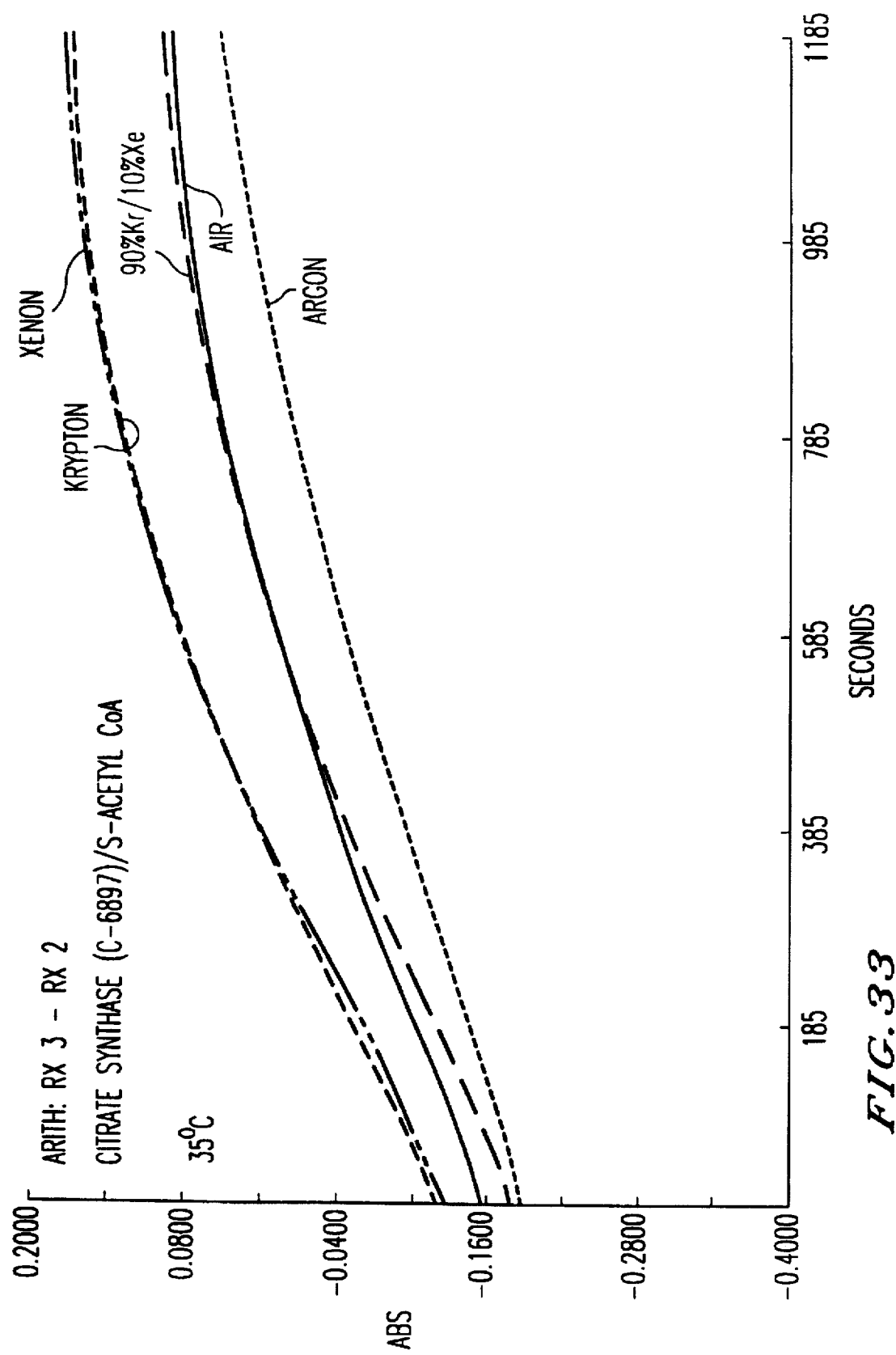
FIG. 33 illustrates the enhancement of citrate synthase by xenon and krypton and the inhibition thereof by argon.
Figure 34:
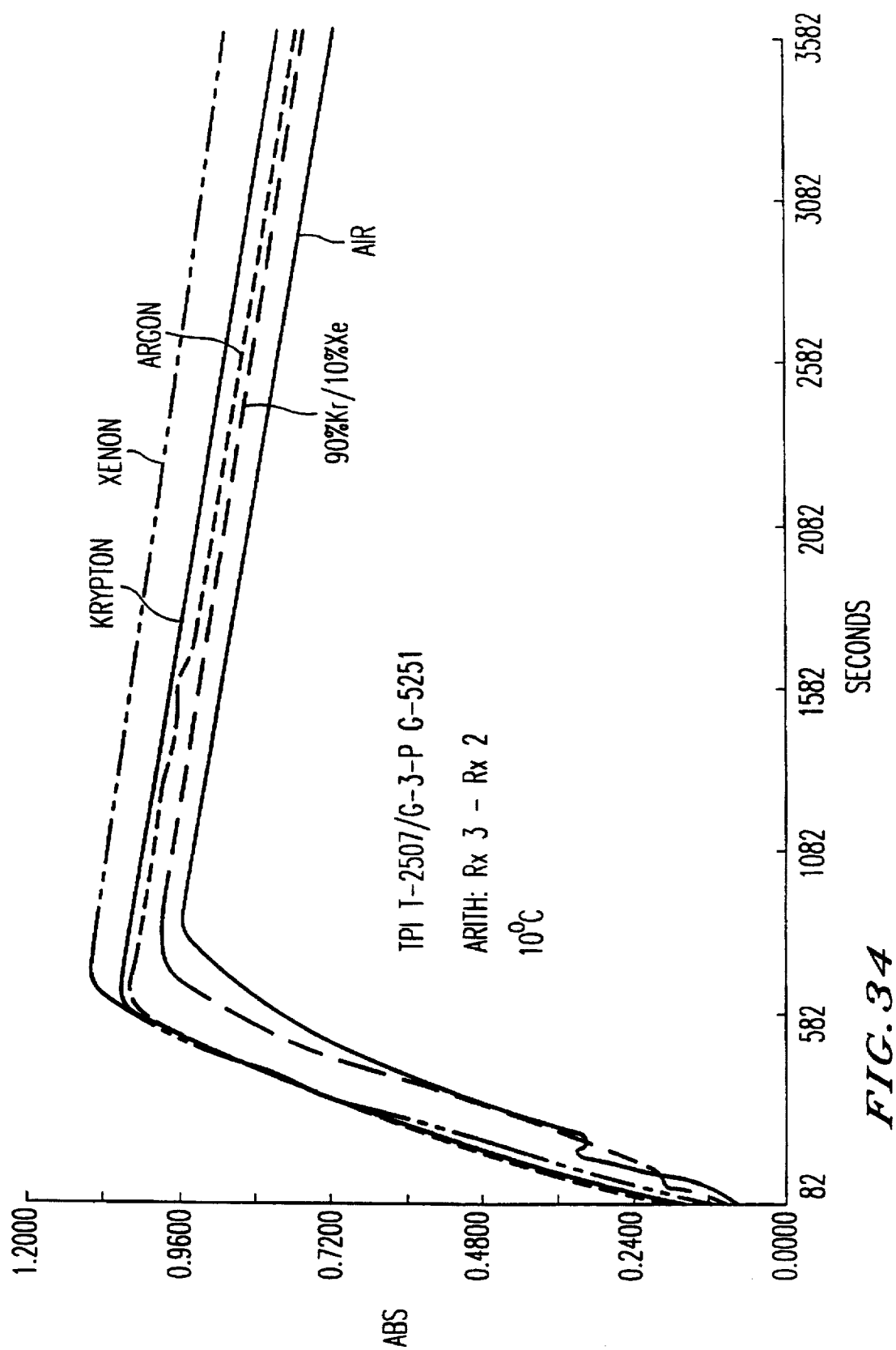
FIG. 34 illustrates the enhancement of phosphoglucose isomerase by xenon, krypton, argon and a mixture of krypton and xenon at 10° C.

FIG. 33 illustrates the enhancement of citrate synthase by xenon and krypton and the inhibition thereof by argon. FIG. 34 illustrates the enhancement of phosphoglucose isomerase by xenon, krypton, argon and a mixture of krypton and xenon at 10° C.

Figure 35:
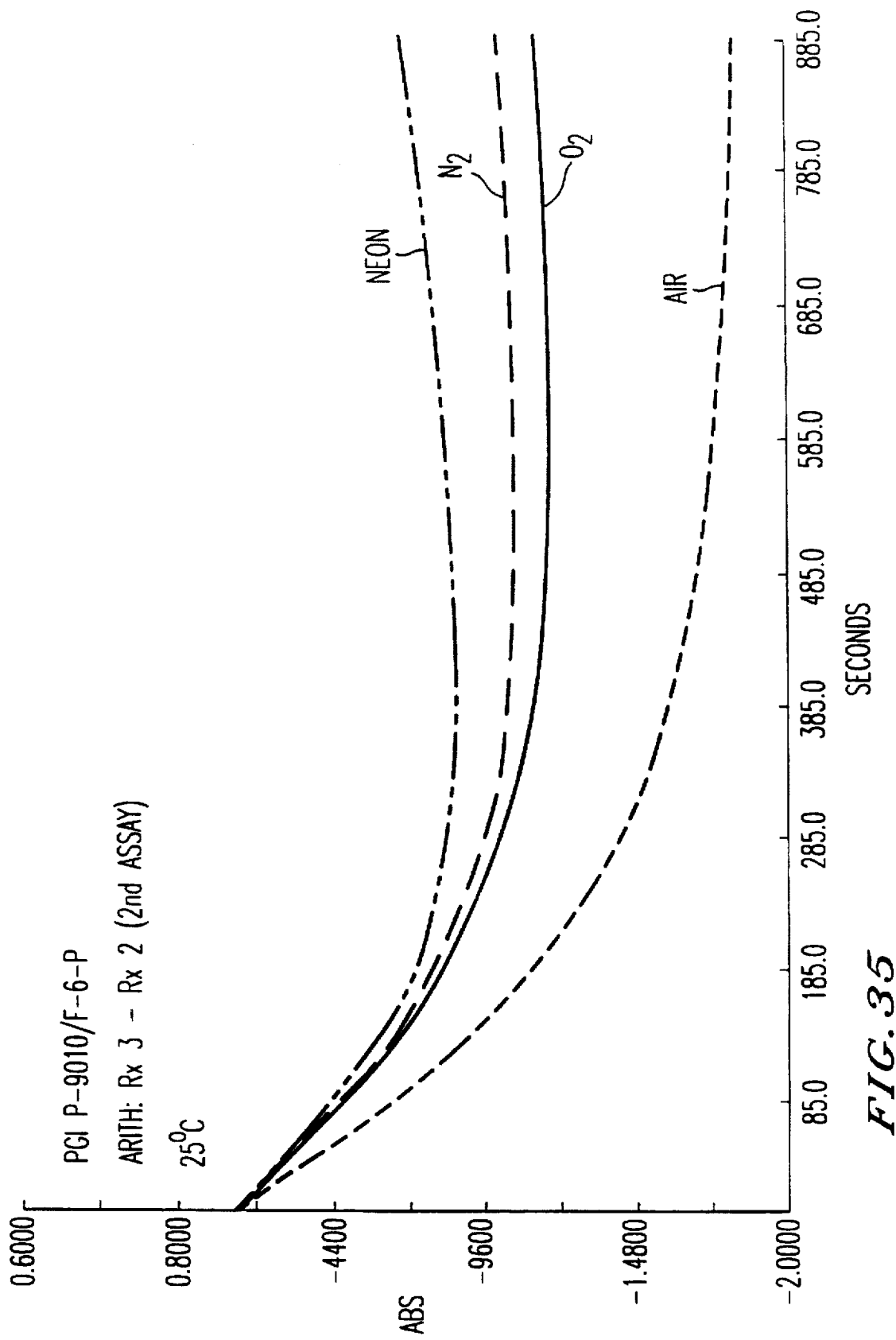
FIG. 35 illustrates the enhancement of phosphoglucose isomerase by neon and nitrogen, and the inhibition thereof by oxygen at 25° C.

FIG. 35 illustrates the enhancement of phosphoglucose isomerase by neon and nitrogen, and the inhibition thereof by oxygen at 25° C.

Figure 36:
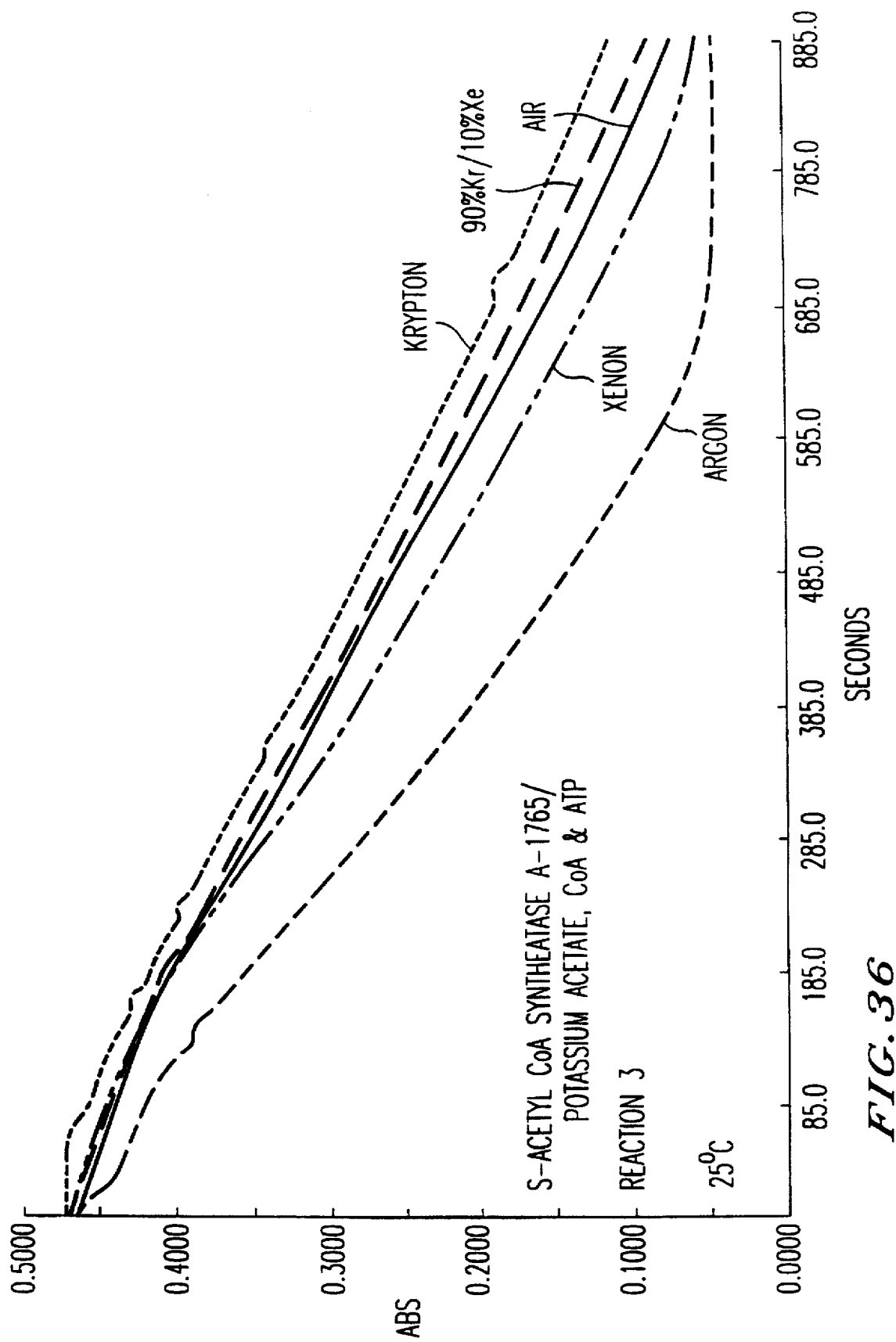
FIG. 36 illustrates the enhancement of S-acetyl CoA synthetase by krypton and a mixture of krypton and xenon at 25° C.

FIG. 36 illustrates the enhancement of S-acetyl CoA synthetase by krypton and a mixture of krypton and xenon at 25° C.

Figure 37:
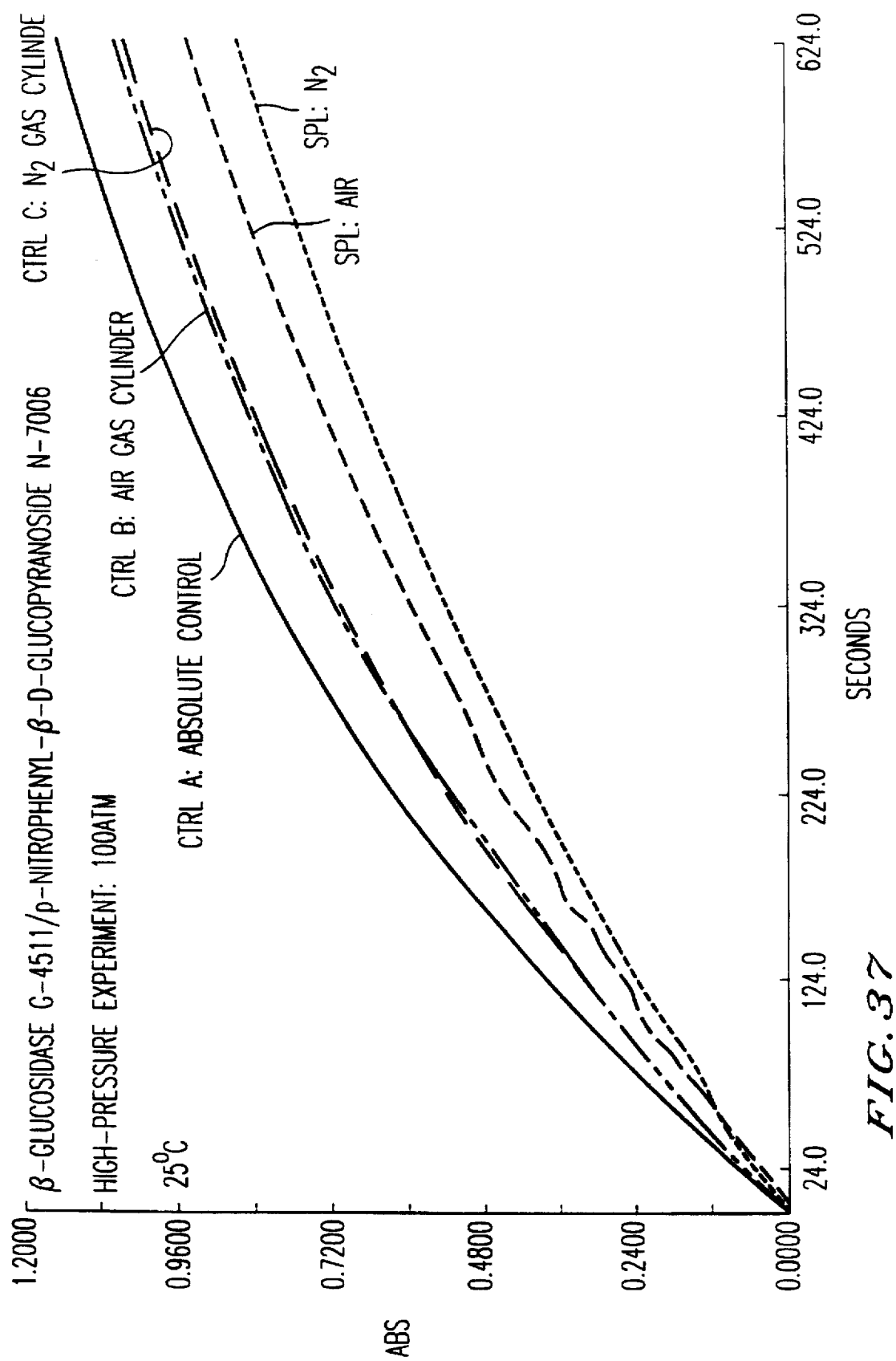
FIG. 37 illustrates the inhibitory effect of air and nitrogen upon β-glucosidase at 100 atm. pressure at 25° C.

FIG. 37 illustrates the inhibitory effect of air and nitrogen upon β-glucosidase at 100 atm. pressure. This effect is simply due to enzyme damage due to high pressure.

Figure 38:
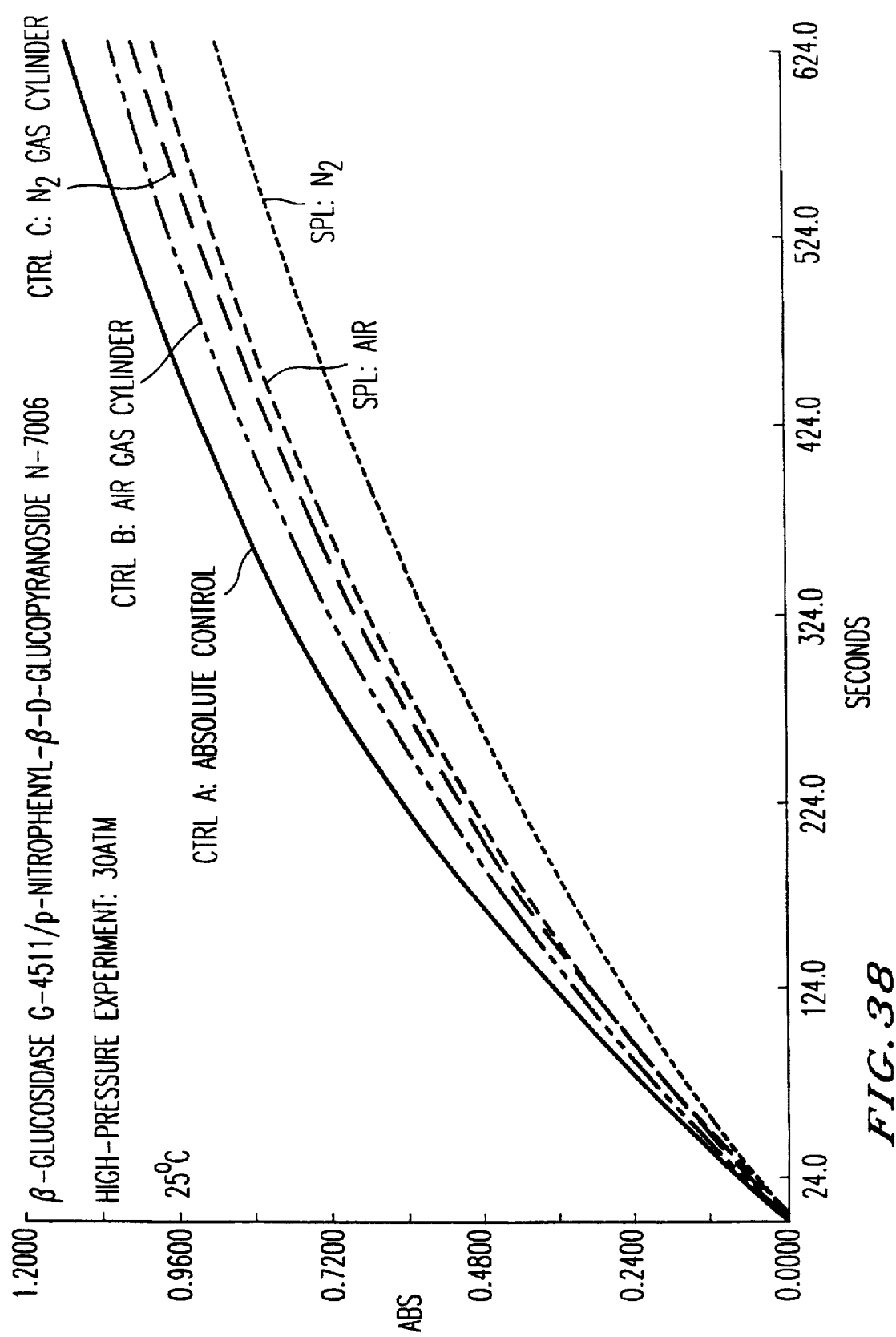
FIG. 38 illustrates the inhibitory effect of air and nitrogen upon β-glucosidase at 30 atm. pressure.

FIG. 38 illustrates the inhibitory effect of air and nitrogen upon β-glucosidase at 30 atm. pressure. This effect is similarly due enzyme damage from high pressure.

Figure 39:
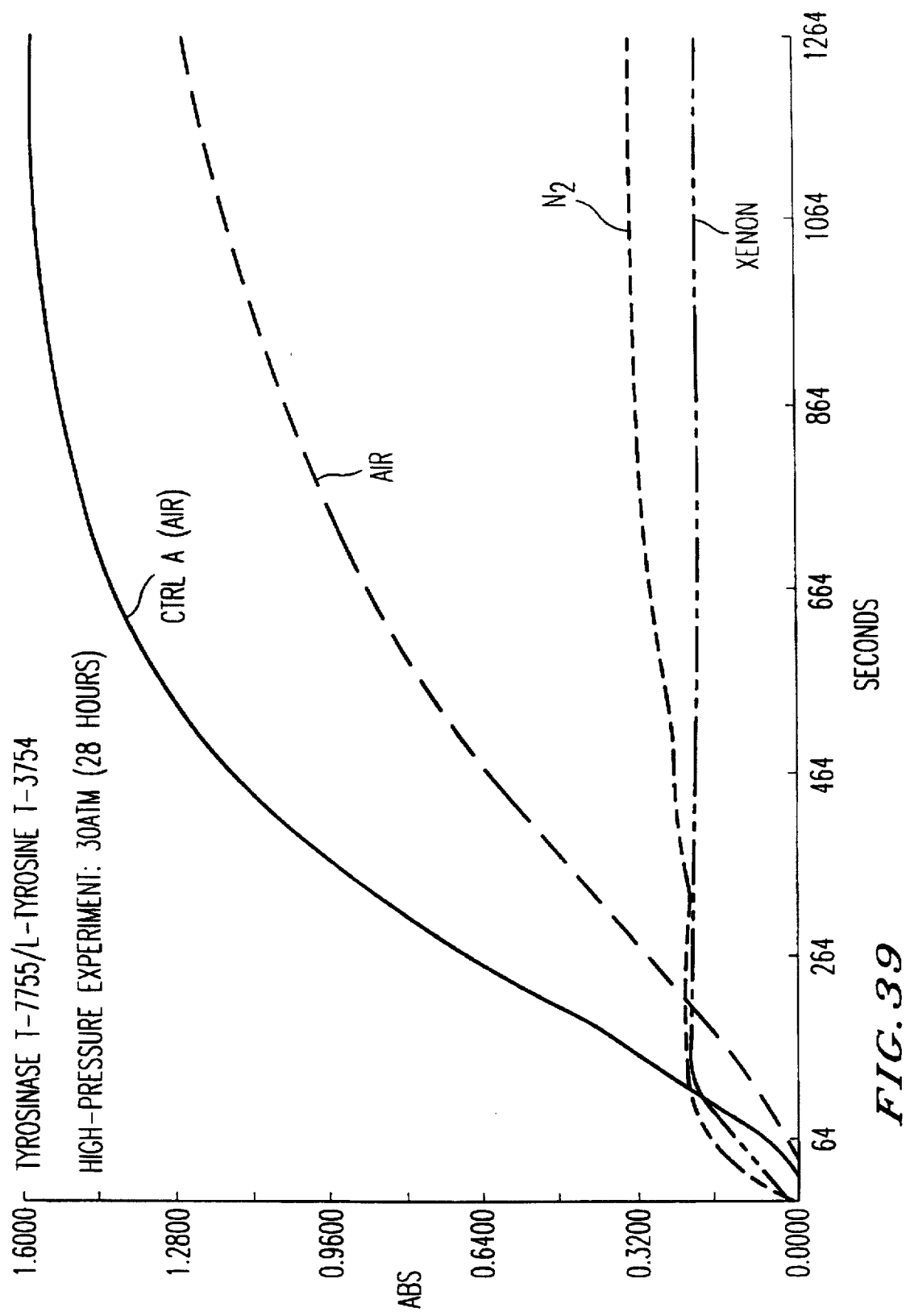
FIG. 39 illustrates the inhibitory effect of air, xenon and nitrogen upon tyrosinase at 30 atm. pressure.

FIG. 39 illustrates the inhibitory effect of air, xenon and nitrogen on tyrosinase activity at 30 atm. pressure. The effect is due to enzyme damage from high pressure.

Figure 40:
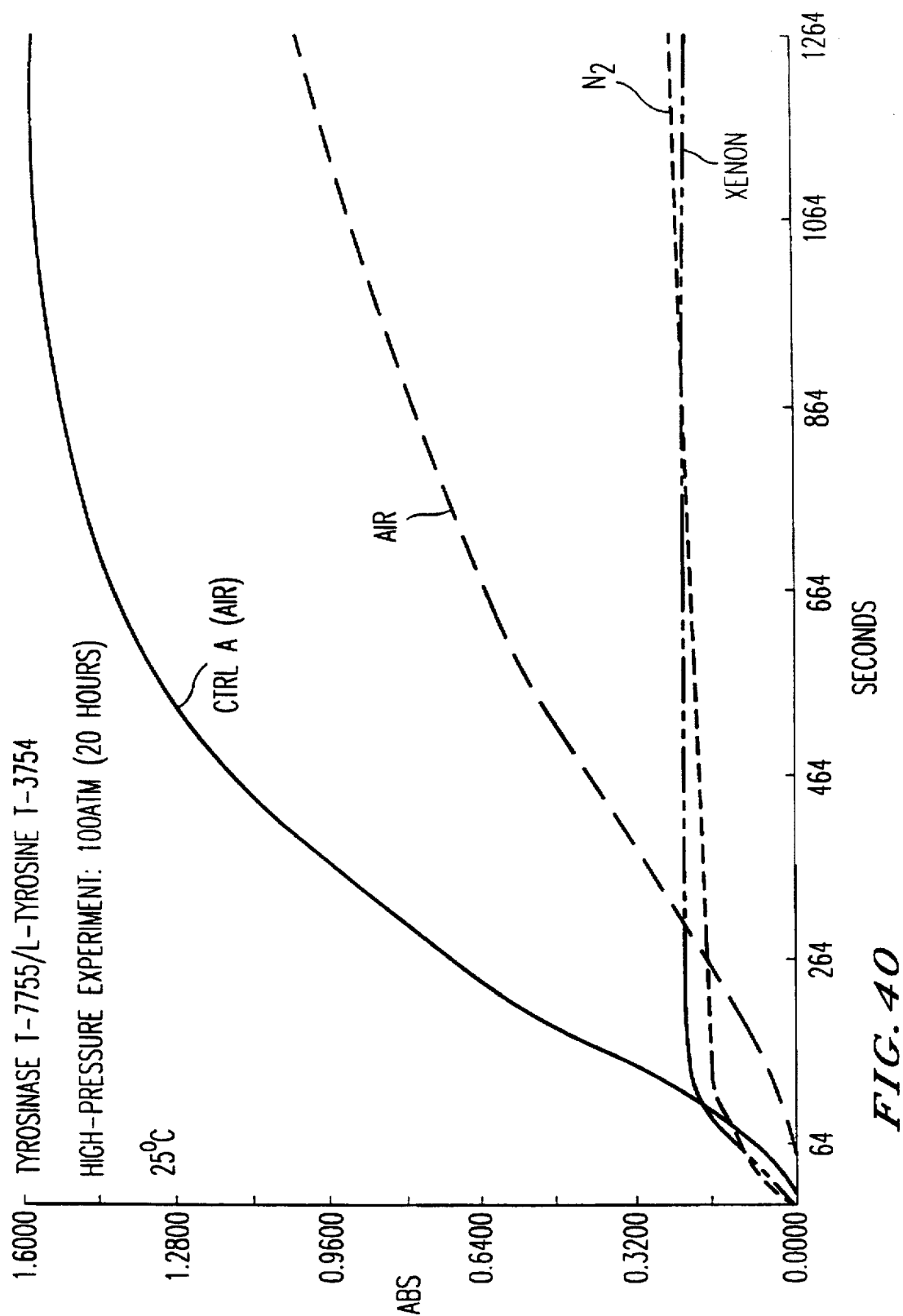
FIG. 40 illustrates the inhibitory effect of air, xenon and nitrogen upon tyrosinase at 100 atm. pressure.

FIG. 40 illustrates the inhibitory effect of air, xenon and nitrogen on tyrosinase at 100 atm. pressure. This effect is due to enzyme damage from high pressure.

Figure 41:
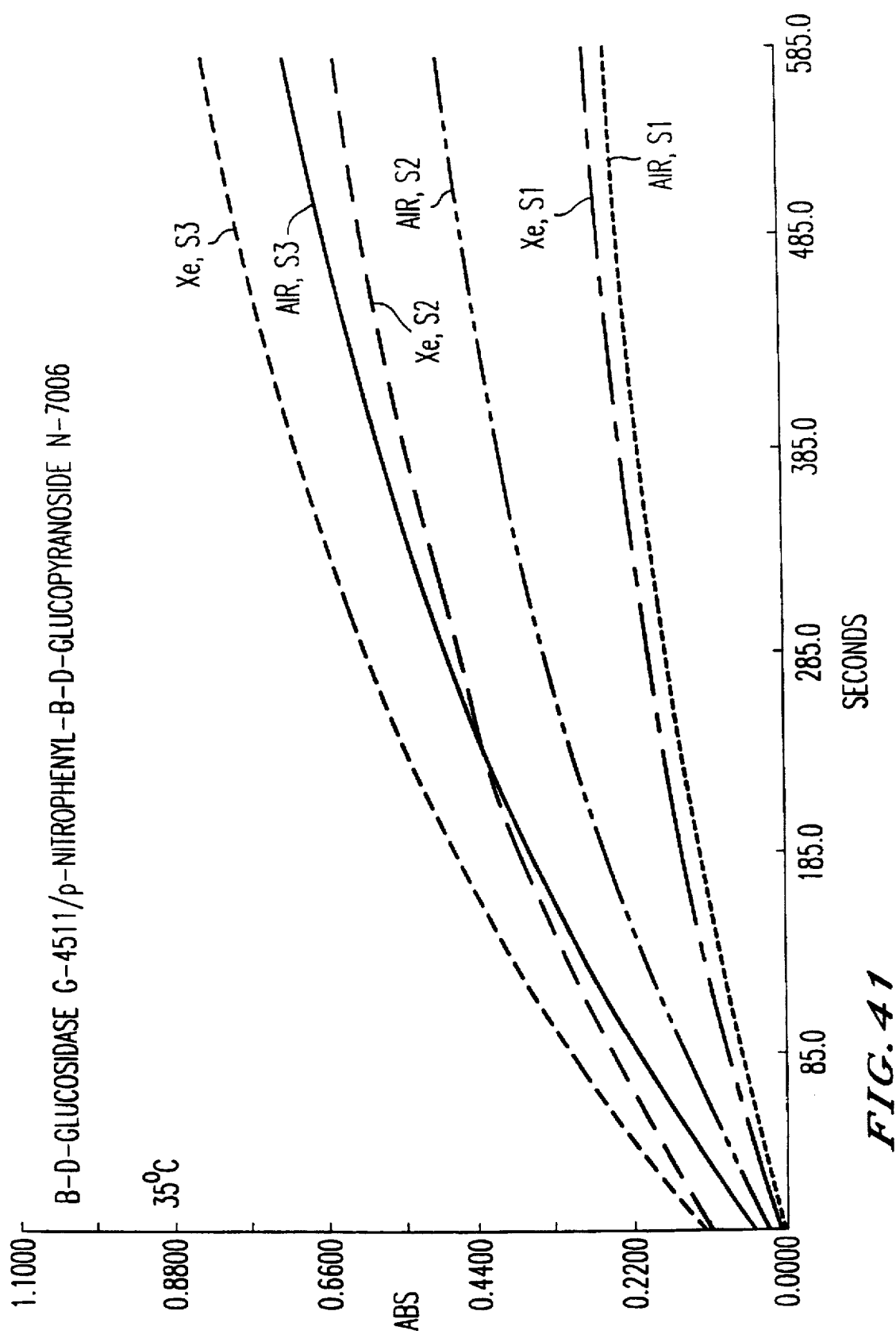
FIG. 41 illustrates that enzyme-substrate concentrations influence the results of noble gas enhancement/inhibition.

FIG. 41 illustrates that enzyme-substrate concentrations influence the results of noble gas enhancement or inhibition, as exemplified with β-D-glucosidase activity. S1, S2 and S3 represent three different and increasing substrate concentrations. This result is advantageous as it means that existing biotechnological processes can be modified to lower the cost of enzyme and/or substrate or even to facilitate reactions not presently possible.

Figure 42:
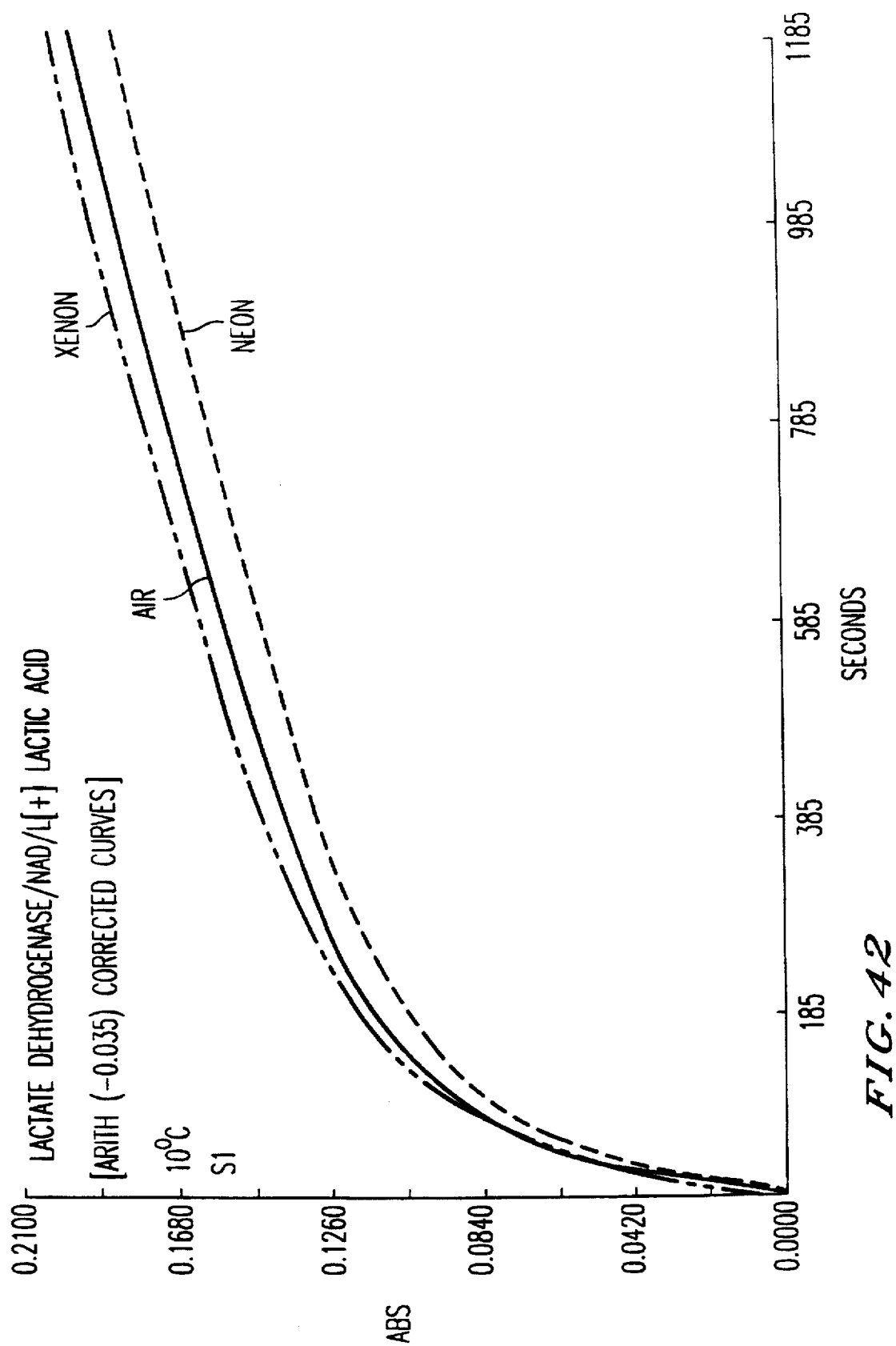
FIG. 42 illustrates the differing effects of xenon and neon, in respectively enhancing, then inhibiting lactate dehydrogenase at 10° C., for example.

FIG. 42 illustrates the differing effects of xenon and neon in, respectively, enhancing, then inhibiting lactate dehydrogenase at 10° C., for example. This is advantageous as it means that a given enzyme may be either enhanced or inhibited depending upon the gas-selected.

Figure 43:
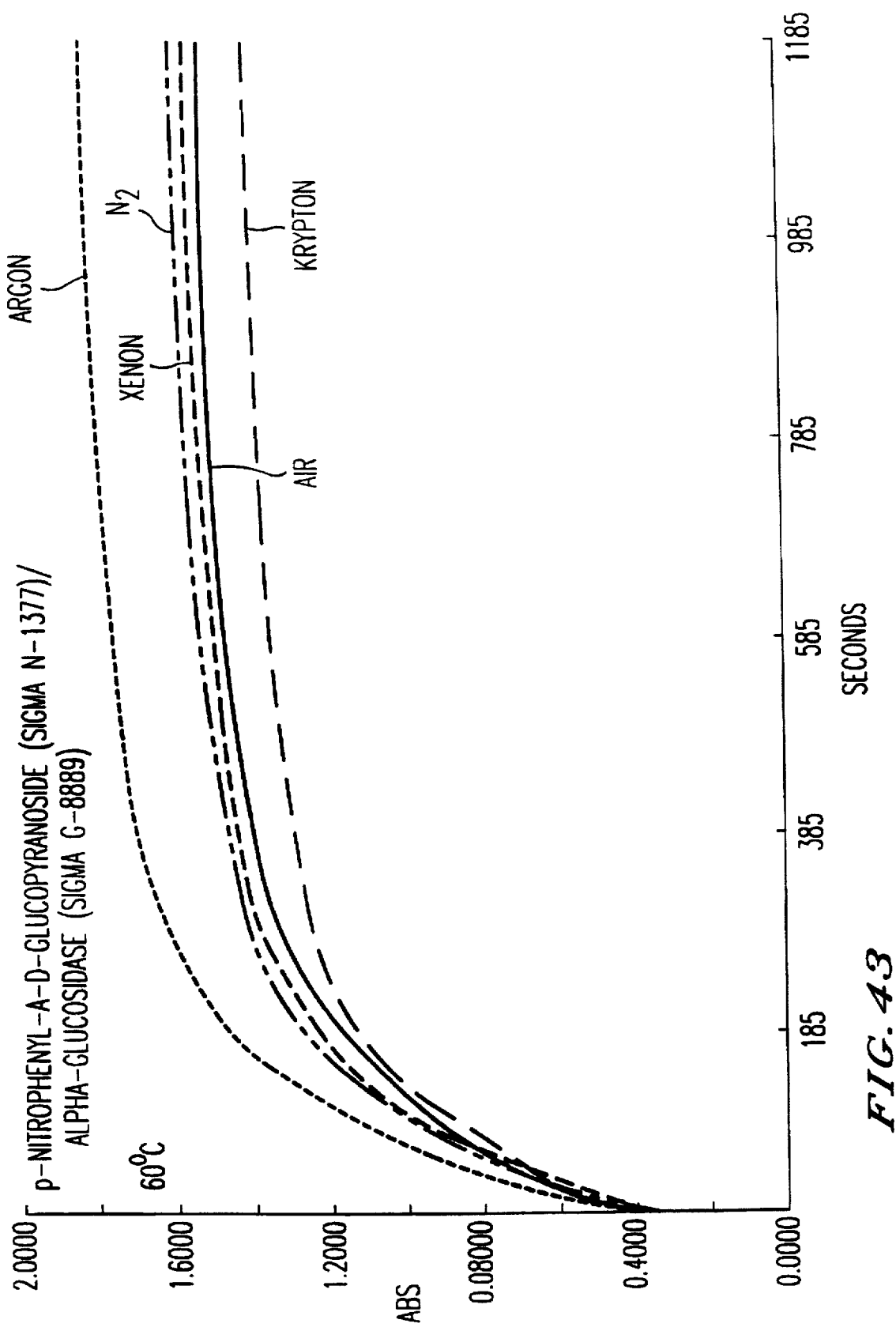
FIG. 43 illustrates that even at 60° C., noble gases exhibit enhancing or inhibitory effects on enzymes.

FIG. 43 illustrates that even at high temperatures, the effect of the present invention is observed. Notably, at 60° C., α-glucosidase activity is enhanced by argon, nitrogen and xenon and inhibited by krypton. Clearly, for this enzyme, argon is a potent enhancer at 60° C.

Figure 44:
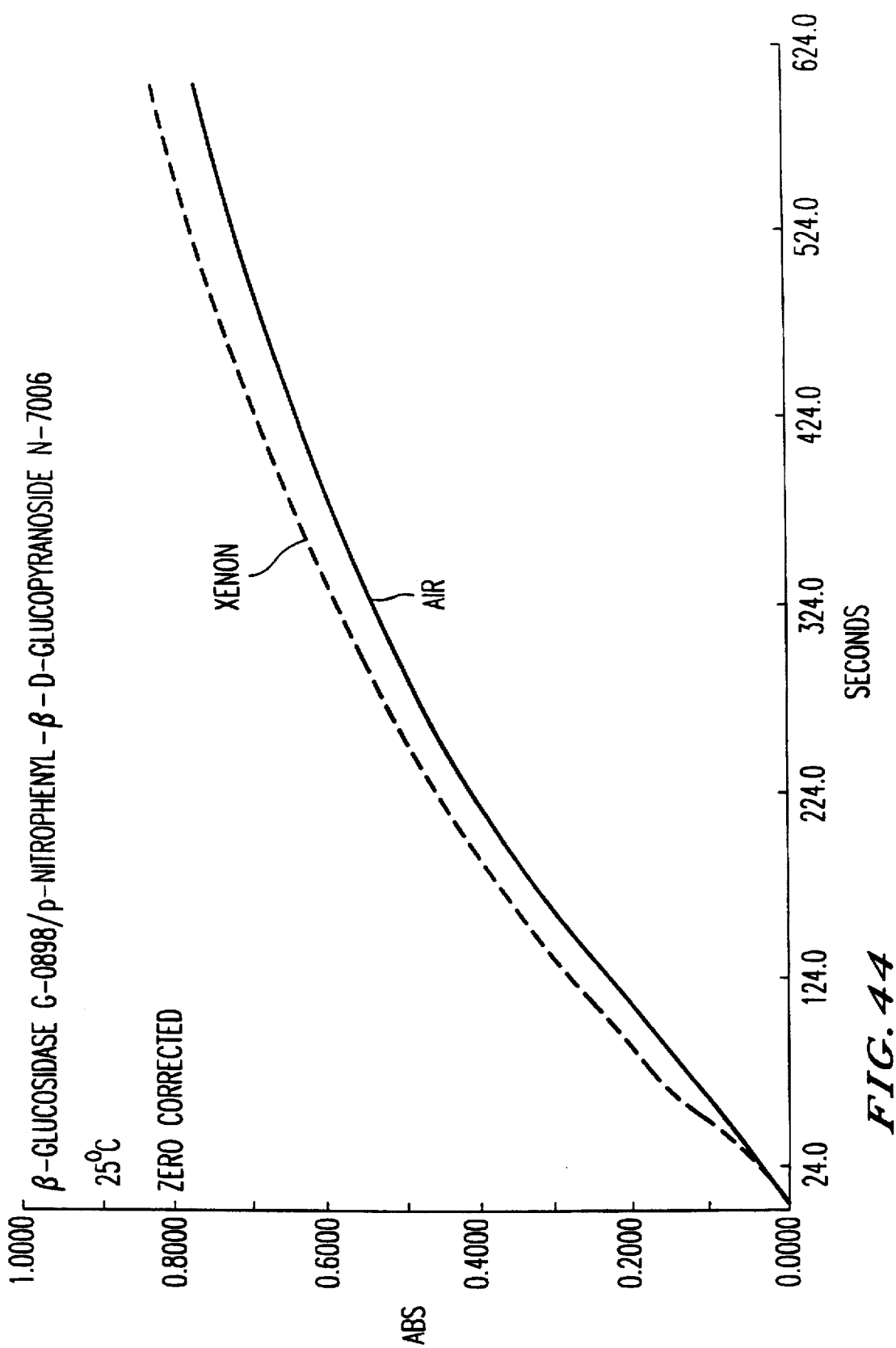
FIG. 44 illustrates the effect of xenon in enhancing β-glucosidase in immobilized form.

FIG. 44 illustrates the effect of xenon at 25° C. in enhancing the enzymatic activity of β-glucosidase in immobilized form.

As noted above, enzymatic activities may be regulated in accordance with the present invention over a wide temperature range ranging from as low as the temperature of liquid nitrogen (about −200° C.) to about 120° C. Moreover, the pressure of the gases or gas mixtures used may be as low as an ultra-high vacuum of about $10^{-8}$ atmospheres to up to about 100 atmospheres. However, it may be desirable to use even lower or even higher pressures. Generally, however, gas pressures of about $10^{-3}$ to about 3 atmospheres are used, with gas pressures of about $10^{-2}$ to about 2 atmospheres most commonly used.

As noted above, the present invention is effective in regulating enzymatic activity regardless of the enzyme selected and the form of the enzyme. The following example is provided to illustrate the effectiveness of the present invention in regulating the enzymatic activity of immobilized enzymes.

Protocol: Immobilized Enzymes

Theory: Same gases effects on either free or immobilized enzymes.

Gases:
  1. Air
  2. Xenon

Enzyme
  β-D-Glucosidase (SIGMA) No. G-0898)
  β-D-Glucoside glucohydrolase EC 3.2.1.21)
  From Caldocellum saccharolyticum: Recombinant (pfs)
  Expressed in *E. coli*
  Lyophilized powder
  Thermostable enzyme with half-life of 38 hr at 70° C.

Unit Definition
  One unit will liberate 1.0 µmole of glucose from salicin per min at pH 5.0 at 37° C.
  Activity: 46 U/g solid
  10.87 g solid→500 Units
  Stored dessicated at 0°–5° C.
  Lot#50H0251

Substrate
  p-Nitrophenyl-β-D-Glucopyranoside (SIGMA No. N-7006)
  Crystalline
  Contains 2.4% solvent
  Anhydrous Mol. Wt. 301.3
  Stored dessicated below 0° C.
  Lot#129F-5057

Solution Preparation
prep: May 21, 1991
  Soln A: Sodium phosphate buffer pH 6.6 at 25° C. 1 T. Deionized water $141.96 \times 0.2 \times 187.5 \times 1/1000 = 5.3$ g $Na_2HPO_4$ $119.96 \times 0.2 \times 312.5 \times 1/1000 = 7.5$ g $NaH_2PO_4$ prep: May 21, 1991
  Soln B: 100 µg/mL β-0-Glucopyranoside solution in Na Phos. buffer 25 mg N-7006 diluted to 250 ml Na Phos. buffer pH 6.6 at 25° C.
prep: May 21, 1991

Soln C1: β-D-Glucosidase solution in Na Phos. buffer pH 6.6 (25° C.) (2.18 Units/ml)

1g G-0898 solubilized in 21 mL Na Phos. buffer pH 6.6 at 25° C.

(For insoluble enzymes lyophilized powders, SIGMA recommends to suspend the required amount to 5–10 mg solid/ml $H_2O$ and to allow brief hydration).

We allowed a brief hydration (until solution appears)

400 nm
80 Pts→
16 s int
$y_{min}=0.0$
$y_{max}=3.0$

Blank: 2 ml Soln A+0.5 ml Soln C1
Sample: 2 ml Soln B+0.5 ml Soln C1
Files: G0898G1 . . . 4.SP

* TRIAL 2: May 22, 1991
Cell Transporter:
  2 replicates
  Run:
    Cell 1: Air
    Cell 2: Air (replicate)
    Cell 3: Xe
    Cell 4: Xe (replicate)
PARAM:
  slit 1
  speed 1500
  Asave Y
  Aprint N
CPRG:
  β-Glucosidase: 25° C.
  400 nm
  120 Pts→
  16 s int
  $y_{min}=0.0$
  $y_{max}=1.0$ Blank: 2 ml Soln A+0.5 ml Soln C2
Sample: 2 ml Soln B+0.5 ml Soln C2
Files: 2G0898G1 . . . 4.SP In order to further exemplify the present invention and the effects obtained thereby, kinetic analyses were conducted.

Kinetic Analyses

Absorbance curve data as previously exemplified reveal differences in enzymatic activity under different gas atmospheres both in terms of yield and in terms of rate. Yield can be calculated after equilibrium is reached by comparative curve differencing, and through formal linearization and calculation—which are also necessary for rate calculations. Rate differences are calculated using commercially available computer programs (ENZFITTER, GRAFIT, ENZPACK, PEAKFIT) which transform the initial uv/vis absorbance data curve (in these examples, a power curve) into straight lines (linear regression of power curve). These lines may be expressed as a mathematical equation in which the slope is approximately the rate, and the limit Y-intercept is approximately the yield. These data may be further treated to derive Michaelis-Menten or other standard biochemical relationships (expressed graphically or mathematically), from which the rate and yield may be exactly derived. The examples and figures described below represent these steps in exemplary form.

Figure 45:
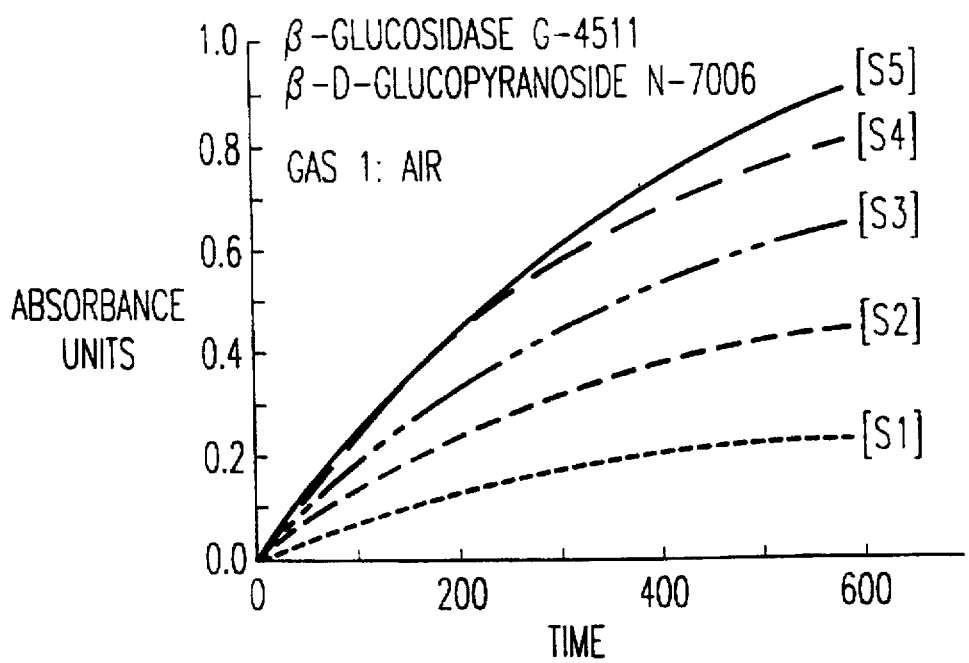
FIG. 45 illustrates uv/vis absorbance power curves for β-glucosidase under air at five different substrate concentrations.

FIG. 45 illustrates uv/vis absorbance power curves for β-glucosidase under air at five different substrate concentrations.

Table 1 illustrates Michaelis-Menten enzyme kinetics calculations of Vmax and Km, and the rates for each reaction. Vmax is the limiting rate, Km is the Michaelis-Menten constant.

Figure 46:
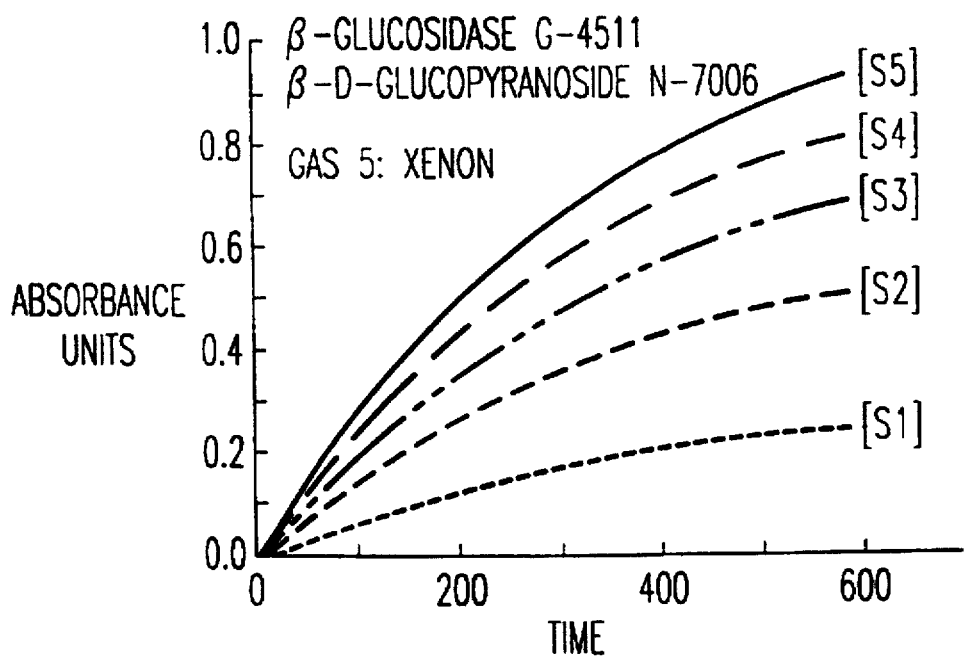
FIG. 46 illustrates uv/vis absorbance power curves for β-glucosidase under xenon at five different substrate concentrations.

FIG. 46 and Table 2 illustrate the same as FIG. 45 and Table 1, however, for xenon reactions. It is readily apparent that the Vmax and Km for xenon are larger.

Figure 47:
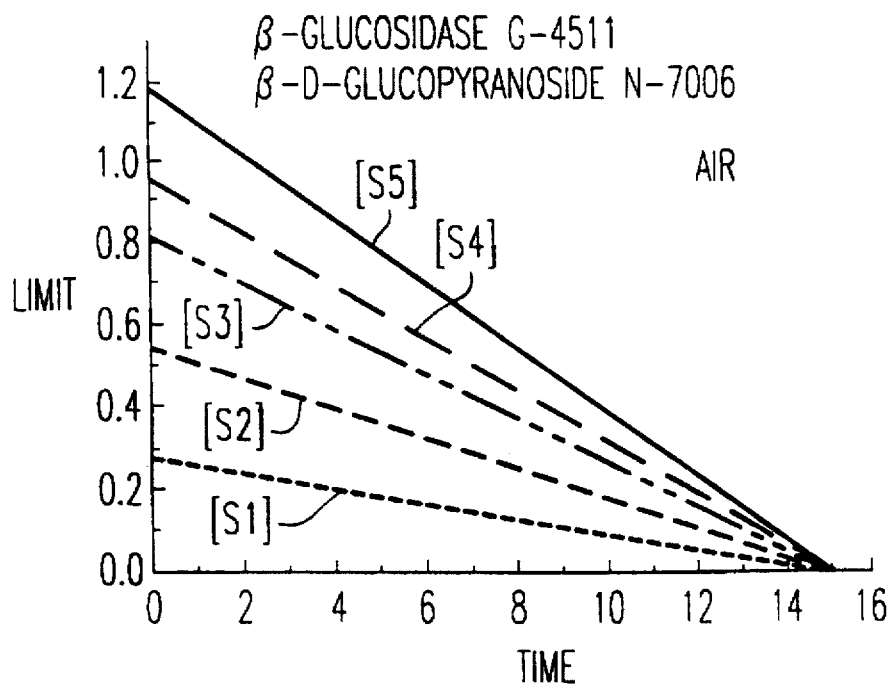
FIG. 47 illustrates the first-order power curve regression rate linear transformations for the β-glucosidase-air gassed reactions.
Figure 48:
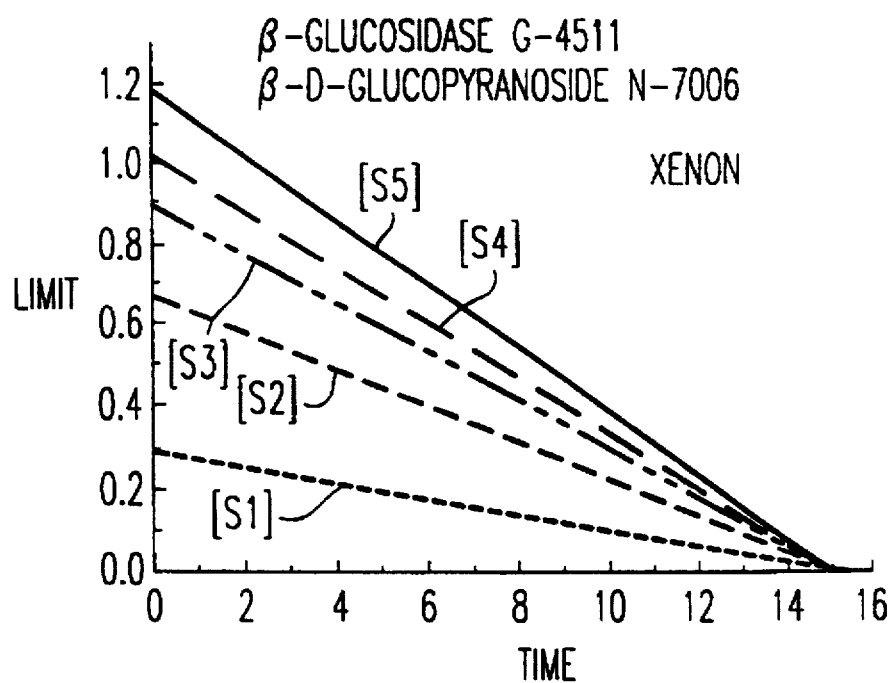
FIG. 48 illustrates the first-order power curve regression rate linear transformations for the β-glucosidase-xenon gassed reactions.

FIG. 47, Table 3, FIG. 48 and Table 4 illustrate the first-order power curve regression rate linear transformations for the above air and xenon gassed reactions, showing an approximation to the Michaelis-Menten data, wherein the Xe/Air rate relationship is in the same ratio as above.

Figure 49:
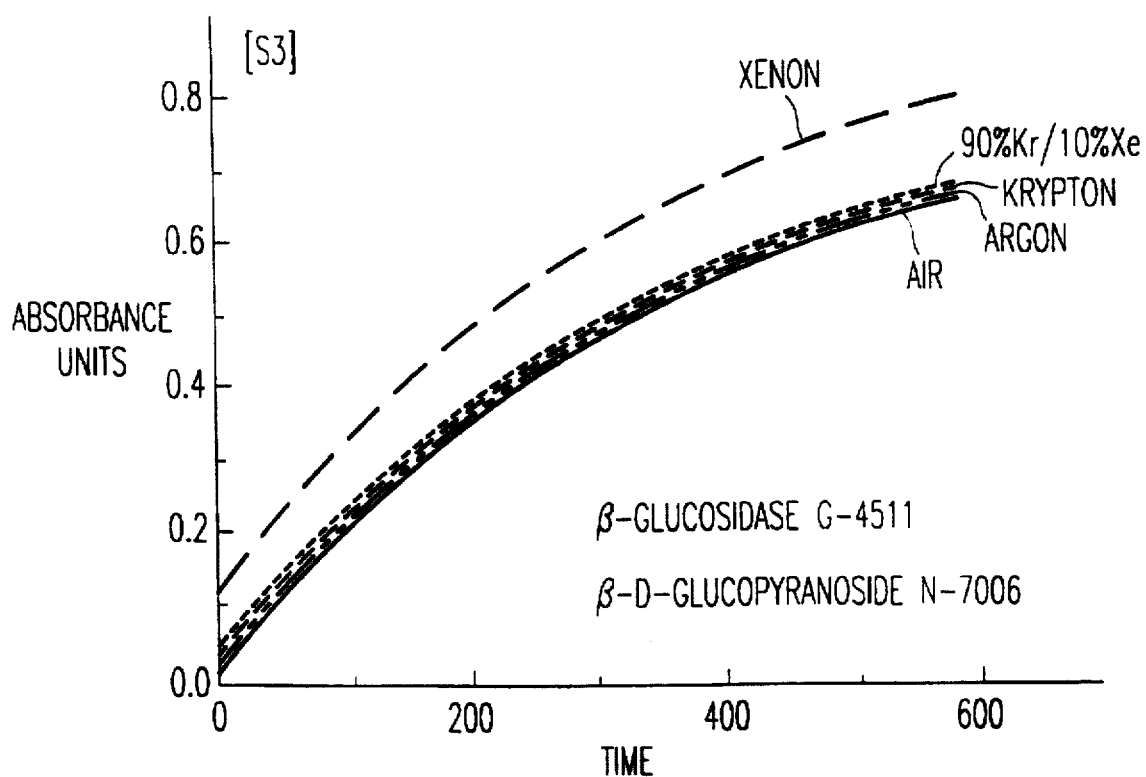
FIGS. 49 and 50 illustrate the same first-order rate approximation regression linearizations for all gases studied in this run.
Figure 50:
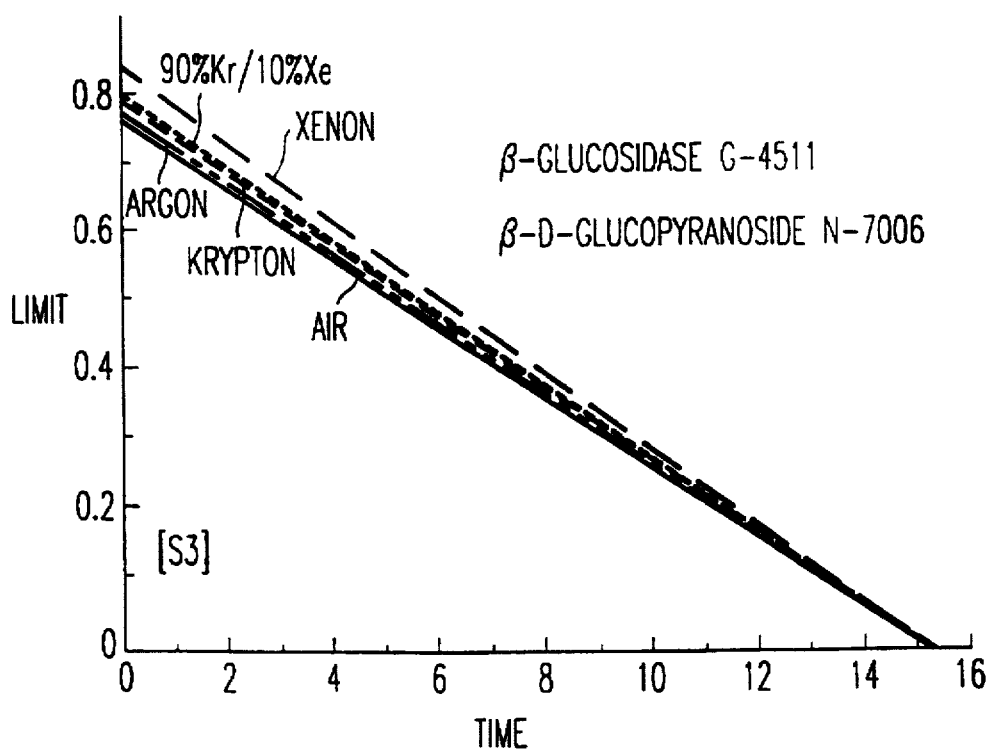

FIG. 49, FIG. 50 and Table 5 illustrate the same first-order rate approximation regression linearizations for all gases studied in this run. In this case, only the xenon showed a significant enhancement, at the power curve analysis, but linearization clearly shows that other gases were enhancing the reaction.

Figure 51:
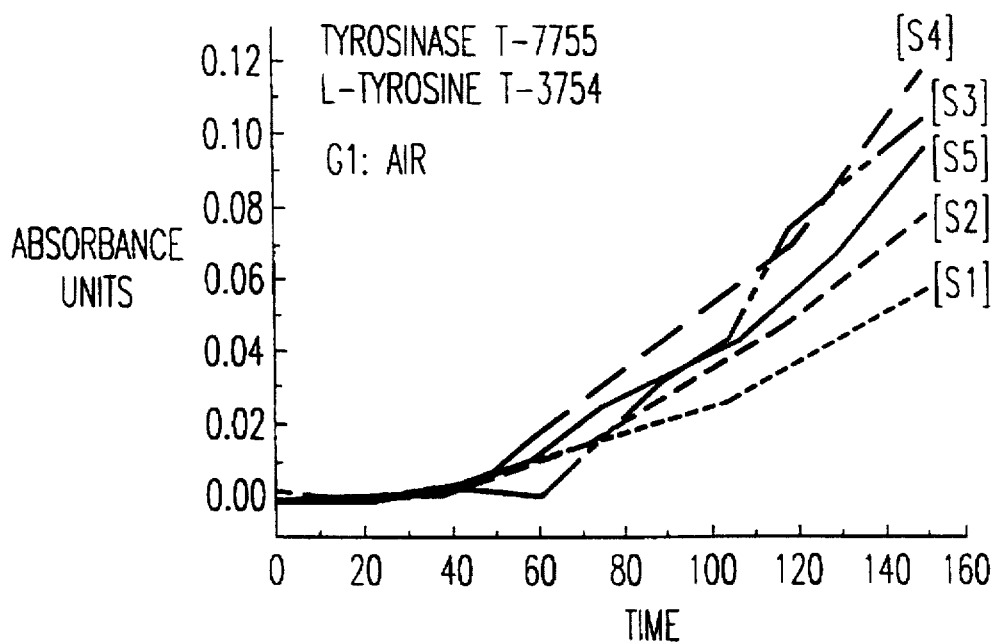
FIGS. 51 and 52 illustrate data from the first 160 seconds of a single tyrosinase experiment expressed as power curves for air, then xenon gassing.
Figure 52:
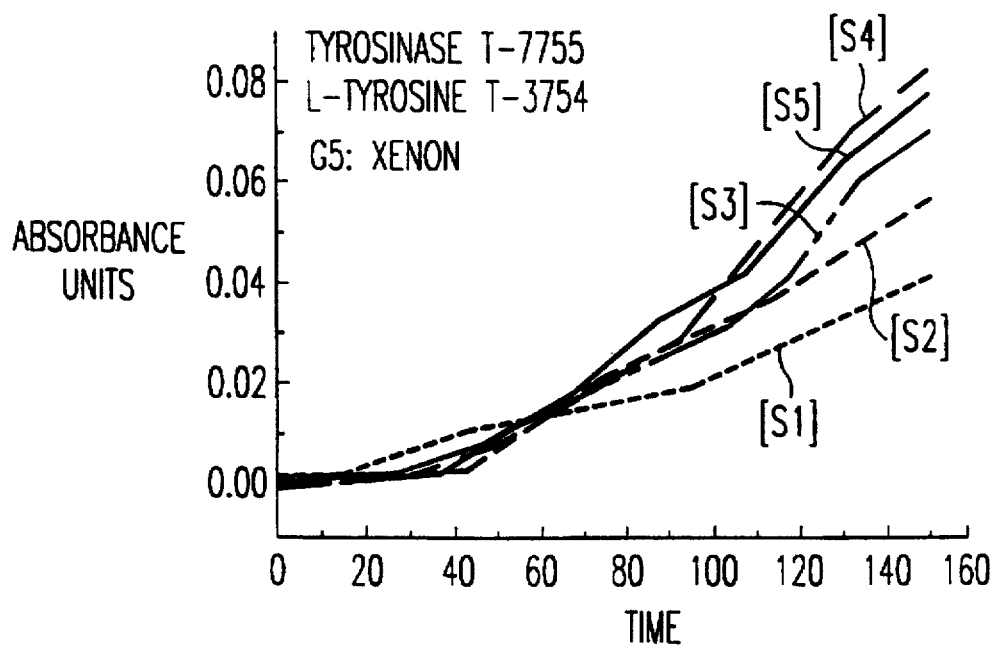

FIG. 51, Table 6, FIG. 52 and Table 7 illustrate data from the first 160 seconds of a single tyrosinase experiment expressed as power curves for air, then for xenon gassing. The linearized rate regression shows that, and the Michaelis-Menten calculations shown confirms that, xenon is strongly inhibiting tyrosinase activity.

TABLE 1

Gas 1: Air
Enzyme Kinetics
Simple weighting
Reduced Chi squared = 0.0000

| Variable | Value | Std. Err. |
|---|---|---|
| V max | 0.0025 | 0.0002 |
| Km | −3.1783 | 2.6341 |

| | X [S] | Y Rates G1 | Calculated |
|---|---|---|---|
| 1 | 20.0000 | 0.0029 | 0.0029 |
| 2 | 40.0000 | 0.0028 | 0.0027 |
| 3 | 60.0000 | 0.0025 | 0.0026 |
| 4 | 80.0000 | 0.0030 | 0.0026 |
| 5 | 100.0000 | 0.0022 | 0.0026 |

The remaining data sets are graphically represented in the Figures as indicated above.

TABLE 2

Gas 5: Xenon
Enzyme Kinetics
Simple weighting
Reduced Chi squared = 0.0000

| Variable | Value | Std. Err. |
|---|---|---|
| V max | 0.0028 | 0.0001 |
| Km | −2.4539 | 1.3570 |

| | X [S] | Y Rates G5 | Calculated |
|---|---|---|---|
| 1 | 20.0000 | 0.0032 | 0.0032 |
| 2 | 40.0000 | 0.0029 | 0.0029 |
| 3 | 60.0000 | 0.0027 | 0.0029 |
| 4 | 80.0000 | 0.0030 | 0.0029 |
| 5 | 100.0000 | 0.0029 | 0.0028 |

TABLE 3

[S] = 60 micrograms/ml
1st order rate equation
Simple weighting
Reduced Chi squared = 0.0002

| Variable | Value | Std. Err. |
|---|---|---|
| Limit | 0.8021 | 0.0146 |
| Rate constant | 0.0032 | 0.0001 |

| | X<br>Time | Y<br>Abs | Calculated |
|---|---|---|---|
| 1 | 0.0000 | 0.0471 | 0.0000 |
| 2 | 15.0000 | 0.0777 | 0.0377 |
| 3 | 30.0000 | 0.1071 | 0.0737 |
| 4 | 45.0000 | 0.1346 | 0.1080 |
| 5 | 60.0000 | 0.1626 | 0.1406 |
| 6 | 75.0000 | 0.1890 | 0.1717 |
| 7 | 90.0000 | 0.2136 | 0.2014 |
| 8 | 105.0000 | 0.2386 | 0.2296 |
| 9 | 120.0000 | 0.2623 | 0.2566 |
| 10 | 135.0000 | 0.2849 | 0.2822 |
| 11 | 150.0000 | 0.3067 | 0.3067 |
| 12 | 165.0000 | 0.3287 | 0.3300 |
| 13 | 180.0000 | 0.3485 | 0.3522 |
| 14 | 195.0000 | 0.3691 | 0.3734 |
| 15 | 210.0000 | 0.3881 | 0.3935 |
| 16 | 225.0000 | 0.4066 | 0.4128 |
| 17 | 240.0000 | 0.4244 | 0.4311 |
| 18 | 255.0000 | 0.4414 | 0.4485 |
| 19 | 270.0000 | 0.4579 | 0.4652 |
| 20 | 285.0000 | 0.4741 | 0.4810 |
| 21 | 300.0000 | 0.4897 | 0.4961 |
| 22 | 315.0000 | 0.5044 | 0.5105 |
| 23 | 330.0000 | 0.5190 | 0.5242 |
| 24 | 345.0000 | 0.5325 | 0.5373 |
| 25 | 360.0000 | 0.5448 | 0.5498 |
| 26 | 375.0000 | 0.5569 | 0.5616 |
| 27 | 390.0000 | 0.5687 | 0.5730 |

TABLE 4

[S] = 60 micrograms/ml
1st order rate equation
Simple weighting
Reduced Chi squared = 0.0014

| Variable | Value | Std. Err. |
|---|---|---|
| Limit | 0.8382 | 0.0228 |
| Rate constant | 0.0045 | 0.0003 |

| | X<br>Time | Y<br>Abs [S3] | Calculated |
|---|---|---|---|
| 1 | 0.0000 | 0.1261 | 0.0000 |
| 2 | 15.0000 | 0.1590 | 0.0544 |
| 3 | 30.0000 | 0.1928 | 0.1053 |
| 4 | 45.0000 | 0.2217 | 0.1529 |
| 5 | 60.0000 | 0.2514 | 0.1974 |
| 6 | 75.0000 | 0.2811 | 0.2390 |
| 7 | 90.0000 | 0.3085 | 0.2779 |
| 8 | 105.0000 | 0.3349 | 0.3143 |
| 9 | 120.0000 | 0.3608 | 0.3483 |
| 10 | 135.0000 | 0.3831 | 0.3801 |
| 11 | 150.0000 | 0.4065 | 0.4099 |
| 12 | 165.0000 | 0.4300 | 0.4377 |
| 13 | 180.0000 | 0.4511 | 0.4637 |
| 14 | 195.0000 | 0.4719 | 0.4880 |
| 15 | 210.0000 | 0.4940 | 0.5108 |
| 16 | 225.0000 | 0.5112 | 0.5320 |
| 17 | 240.0000 | 0.5311 | 0.5519 |
| 18 | 255.0000 | 0.5503 | 0.5705 |
| 19 | 270.0000 | 0.5675 | 0.5879 |
| 20 | 285.0000 | 0.5842 | 0.6042 |

TABLE 4-continued

[S] = 60 micrograms/ml
1st order rate equation
Simple weighting
Reduced Chi squared = 0.0014

| Variable | Value | Std. Err. |
|---|---|---|
| 21 | 300.0000 | 0.6011 | 0.6194 |
| 22 | 315.0000 | 0.6165 | 0.6336 |
| 23 | 330.0000 | 0.6313 | 0.6469 |
| 24 | 345.0000 | 0.6460 | 0.6593 |
| 25 | 360.0000 | 0.6588 | 0.6709 |
| 26 | 375.0000 | 0.6711 | 0.6818 |
| 27 | 390.0000 | 0.6834 | 0.6919 |

TABLE 5

Gas 1: Air
1st order rate equation
Simple weighting
Reduced Chi squared = 0.0002

| Variable | Value | Std. Err. |
|---|---|---|
| Limit | 0.8021 | 0.0146 |
| Rate constant | 0.0032 | 0.0001 |

| | X<br>Time | Y<br>Abs G1 | Calculated |
|---|---|---|---|
| 1 | 0.0000 | 0.0471 | 0.0000 |
| 2 | 15.0000 | 0.0777 | 0.0377 |
| 3 | 30.0000 | 0.1071 | 0.0737 |
| 4 | 45.0000 | 0.1346 | 0.1080 |
| 5 | 60.0000 | 0.1626 | 0.1406 |
| 6 | 75.0000 | 0.1890 | 0.1717 |
| 7 | 90.0000 | 0.2136 | 0.2014 |
| 8 | 105.0000 | 0.2386 | 0.2296 |
| 9 | 120.0000 | 0.2623 | 0.2566 |
| 10 | 135.0000 | 0.2849 | 0.2822 |
| 11 | 150.0000 | 0.3067 | 0.3067 |
| 12 | 165.0000 | 0.3287 | 0.3300 |
| 13 | 180.0000 | 0.3485 | 0.3522 |
| 14 | 195.0000 | 0.3691 | 0.3734 |
| 15 | 210.0000 | 0.3881 | 0.3935 |
| 16 | 225.0000 | 0.4066 | 0.4128 |
| 17 | 240.0000 | 0.4244 | 0.4311 |
| 18 | 255.0000 | 0.4414 | 0.4485 |
| 19 | 270.0000 | 0.4579 | 0.4652 |
| 20 | 285.0000 | 0.4741 | 0.4810 |
| 21 | 300.0000 | 0.4897 | 0.4961 |
| 22 | 315.0000 | 0.5044 | 0.5105 |
| 23 | 330.0000 | 0.5190 | 0.5242 |
| 24 | 345.0000 | 0.5325 | 0.5373 |
| 25 | 360.0000 | 0.5448 | 0.5498 |
| 26 | 375.0000 | 0.5569 | 0.5616 |
| 27 | 390.0000 | 0.5687 | 0.5730 |

TABLE 6

Gas 1: Air
Enzyme Kinetics
Simple weighting
Reduced Chi squared = 0.0000

| Variable | Value | Std. Err. |
|---|---|---|
| V max | 0.0003 | 0.0003 |
| Km | −17.0661 | 3.5059 |

| X [S] | Y Gas 1: Air | Calculated |
|---|---|---|
| 1 | 10.0000 | 0.0018 | −0.0004 |
| 2 | 20.0000 | 0.0019 | 0.0021 |
| 3 | 30.0000 | 0.0011 | 0.0007 |
| 4 | 40.0000 | 0.0018 | 0.0005 |
| 5 | 50.0000 | 0.0018 | 0.0005 |

TABLE 7

Gas 5: Xenon
Enzyme Kinetics
Simple weighting
Reduced Chi squared = 0.0000

| Variable | Value | Std. Err. |
|---|---|---|
| V max | 0.0001 | 0.0003 |
| Km | −27.9623 | 6.3527 |

| X [S] | Y Gas 5: Xenon | Calculated |
|---|---|---|
| 1 | 10.0000 | 0.0007 | −0.0001 |
| 2 | 20.0000 | 0.0019 | −0.0003 |
| 3 | 30.0000 | 0.0019 | 0.0017 |
| 4 | 40.0000 | 0.0019 | 0.0004 |
| 5 | 50.0000 | 0.0004 | 0.0003 |

Thus, the present invention provides a method of regulating enzymatic activity of any enzyme and in any form. Further, this regulation may be effected over the broad temperature and pressure ranges indicated.

As noted previously, the regulated enzyme or enzymes of the present invention may be in an aqueous or organic solution, in immobilized form, in a dispersion or in any type of organic matrix, such as a gel, for example. Such solutions, immobilized forms, dispersions or organic matrices are known to those skilled in the art.

Additionally, in accordance with the present invention, a mixture of enzymes may be regulated by inhibiting one or more enzymes therein or by enhancing one or more enzymes therein. Alternatively, it is possible to effect regulation by both inhibiting one or more enzymes in the mixture and enhancing one or more other enzymes therein.

Further, it is well within the skill of the artisan to utilize the present disclosure and guidelines set forth hereinabove to determine the optical levels of pH, temperature, pressure, [E] and [S] for any particular enzyme system or mixed enzyme system of interest.

For example, for any particular enzyme system or mixed enzyme system of interest, optical conditions of pH, pressure, temperature, [E] and [S] may be ascertained when purchasing the enzyme or enzymes, and by using well known reference manuals. See, for example, the catalogues of the Sigma Chemical Company for 1990 and 1991, and *Enzymes* by Dixon and Webb, Third Edition (Wiley, 1979).

From this knowledge, the artisan can then ascertain, using the present disclosure, the optimal mixture of gases, temperature and pressure in order to obtain the desired effects in accordance with the present invention.

Having described the present invention, it will now be apparent to one of ordinary skill in the art that many changes and modifications can be made to the above embodiments without departing from the spirit and the scope of the present invention.

What is claimed as new and desired to be secured by Letters Patent of the United States is:

1. A method for using an enzyme to act on a substrate therefor in a liquid medium, which enzyme activity is regulated by causing an atmosphere surrounding said liquid medium to undergo a transition from being an enzyme activity inhibitor to an enzyme activity enhancer or vice versa, relative to when air is used as said atmosphere, by a change in temperature, which method comprises contacting at least one enzyme selected from the group consisting of oxidoreductases, lyases, isomerases and ligases, with the substrate therefor in said liquid medium, and during at least part of said contacting, contacting said at least one enzyme with an amount to so regulate said enzyme activity of said atmosphere, which consists essentially of argon, neon, xenon, krypton or a mixture thereof, at a temperature effective to cause said transition, and at a pressure of up to about 3 atmospheres.

2. The method of claim 1, wherein said one or more enzymes are regulated by causing said atmosphere to undergo a transition from being an enzyme activity inhibitor to an enzyme activity enhancer.

3. The method of claim 1, wherein in a mixture enzymes, the enzymatic activity of one or more enzymes therein is regulated by causing said atmosphere to undergo a transition from being an enzyme activity inhibitor to an enzyme activity enhancer.

4. The method of claim 1, wherein said one or more enzymes are regulated by causing said atmosphere to undergo a transition from being an enzyme activity enhancer to an enzyme activity inhibitor.

5. The method of claim 1, wherein said one or more enzymes are in solution, in immobilized form, in a dispersion or in an organic matrix.

6. The method of claim 1, wherein said regulation is effected at a temperature of from about 20° C. to about 60° C.

7. The method of claim 1, wherein said regulation is effected at a gas pressure of from about $10^{-3}$ atmospheres to about 2 atmospheres.

8. The method of claim 7, wherein said regulation is effected at a gas pressure of from about $10^{-2}$ atmospheres to about 2 atmospheres.

9. The method of claim 1, wherein said one or more enzymes are oxidoreductases.

10. The method of claim 1, wherein said one or more enzymes are lyases.

11. The method of claim 1, wherein said one or more enzymes are transferases.

12. The method of claim 1, wherein said one or more enzymes are isomerases.

13. The method of claim 1, wherein said one or more enzymes are ligases.

* * * * *